(12) United States Patent
Shetty et al.

(10) Patent No.: US 10,810,283 B2
(45) Date of Patent: Oct. 20, 2020

(54) SYSTEMS AND METHODS FOR MONITORING RESPIRATORY FUNCTION

(71) Applicant: Knox Medical Diagnostics Inc., San Francisco, CA (US)

(72) Inventors: Charvi Shetty, San Francisco, CA (US); Vinidhra Mani, San Francisco, CA (US); Inderjit Jutla, San Francisco, CA (US)

(73) Assignee: KNOX MEDICAL DIAGNOSTICS INC., San Francisco, CA (US)

( * ) Notice: Subject to any disclaimer, the term of this patent is extended or adjusted under 35 U.S.C. 154(b) by 665 days.

(21) Appl. No.: 15/032,032

(22) PCT Filed: Oct. 31, 2014

(86) PCT No.: PCT/US2014/063592
§ 371 (c)(1),
(2) Date: Apr. 25, 2016

(87) PCT Pub. No.: WO2015/066562
PCT Pub. Date: May 7, 2015

(65) Prior Publication Data
US 2017/0270260 A1 Sep. 21, 2017

Related U.S. Application Data

(60) Provisional application No. 61/898,402, filed on Oct. 31, 2013, provisional application No. 61/931,527, filed on Jan. 24, 2014.

(51) Int. Cl.
*A61B 5/08* (2006.01)
*G06F 19/00* (2018.01)
(Continued)

(52) U.S. Cl.
CPC ........ *G06F 19/3418* (2013.01); *A61B 5/0024* (2013.01); *A61B 5/082* (2013.01);
(Continued)

(58) Field of Classification Search
CPC .. G06F 19/3418; G06F 19/00; G06F 19/3462; G16H 10/60; A61M 15/0086;
(Continued)

(56) References Cited

U.S. PATENT DOCUMENTS 5,060,655 A * 10/1991 Rudolph ................ A61B 5/087
600/529
5,134,890 A * 8/1992 Abrams ................ A61B 5/087
600/538
(Continued)

OTHER PUBLICATIONS

Chen et al. (2013), "Applications and Technology of Electronic Nose for Clinical Diagnosis", Open Journal of Applied Biosensor, 2: 39-50.
(Continued)

*Primary Examiner* — Navin Natnithithadha
*Assistant Examiner* — Andrey Shostak
(74) *Attorney, Agent, or Firm* — Foley & Lardner LLP

(57) ABSTRACT

A portable, handheld measurement device for monitoring lung function is provided. The measurement device includes one or more components designed to directly or indirectly detect air flow properties such as the direction, flow rate, and/or volume of air flow within a lumen of the device. In some embodiments, the air flow properties are determined from changes in pressure within the lumen. The measurement device may form part of a system that includes a remote computing device and a computer server. In some such embodiments, at least one of the computers present within the system calculates spirometry measurements from the air flow detected within the measurement device. Such
(Continued)

measurements may be stored, displayed, and/or shared with others. Various methods performed by the devices and systems are also disclosed.

13 Claims, 33 Drawing Sheets

(51) Int. Cl.
| | |
|---|---|
| *G16H 10/60* | (2018.01) |
| *A61B 5/00* | (2006.01) |
| *A61B 5/087* | (2006.01) |
| *A61B 5/097* | (2006.01) |
| *A61M 15/00* | (2006.01) |
| *A61M 16/00* | (2006.01) |
| *A61M 16/08* | (2006.01) |
| *A61M 16/10* | (2006.01) |

(52) U.S. Cl.
CPC .............. *A61B 5/087* (2013.01); *A61B 5/097* (2013.01); *A61B 5/6898* (2013.01); *A61B 5/7282* (2013.01); *A61B 5/743* (2013.01); *A61B 5/7435* (2013.01); *A61M 15/0086* (2013.01); *G06F 19/3462* (2013.01); *G16H 10/60* (2018.01); *A61B 2560/0223* (2013.01); *A61B 2562/0247* (2013.01); *A61M 16/0841* (2014.02); *A61M 16/1055* (2013.01); *A61M 2016/0021* (2013.01); *A61M 2016/0036* (2013.01); *A61M 2230/40* (2013.01)

(58) Field of Classification Search
CPC .......... A61M 16/1055; A61M 16/0841; A61M 2016/0021; A61M 2016/0036; A61M 2230/40; A61B 2562/0247; A61B 2560/0223; A61B 5/743; A61B 5/7435; A61B 5/6898; A61B 5/0024; A61B 5/097; A61B 5/7282; A61B 5/087; A61B 5/082

See application file for complete search history.

(56) References Cited

U.S. PATENT DOCUMENTS

| | | | | |
|---|---|---|---|---|
| 5,357,972 | A * | 10/1994 | Norlien | A61B 5/087 |
| | | | | 600/538 |
| 5,724,986 | A | 3/1998 | Jones et al. | |
| 6,435,183 | B1 | 8/2002 | Farman | |
| 6,612,306 | B1 | 9/2003 | Mault | |
| 7,282,032 | B2 | 10/2007 | Miller | |
| 8,398,561 | B2 | 3/2013 | Quinn | |
| 8,545,415 | B2 | 10/2013 | West | |
| 2010/0282245 | A1 | 11/2010 | Star et al. | |
| 2011/0092840 | A1* | 4/2011 | Forbes | A61B 5/0876 |
| | | | | 600/538 |
| 2012/0029376 | A1 | 2/2012 | Meng et al. | |
| 2012/0130265 | A1 | 5/2012 | Cha et al. | |
| 2012/0136271 | A1* | 5/2012 | Shavit | A61B 5/087 |
| | | | | 600/538 |
| 2013/0172773 | A1 | 7/2013 | Halwani et al. | |
| 2013/0317379 | A1 | 11/2013 | Brimer et al. | |
| 2014/0066731 | A1 | 3/2014 | Sadasivam | |
| 2014/0206949 | A1 | 7/2014 | Lucas | |
| 2015/0119743 | A1* | 4/2015 | Maksym | A61B 5/085 |
| | | | | 600/533 |
| 2015/0126889 | A1 | 5/2015 | Frey et al. | |
| 2015/0136129 | A1* | 5/2015 | Mahadevan | A61M 16/0069 |
| | | | | 128/203.14 |
| 2015/0164373 | A1* | 6/2015 | Davis | A61B 5/082 |
| | | | | 600/532 |

OTHER PUBLICATIONS

Hunter G W et al. (2011), "Smart sensor systems for human health breath monitoring applications", 2011 J. of Breath Res., 5: 1-11.
International Search Report and Written Opinion for International Application No. PCT/US2014/063592 dated Jun. 12, 2015.
Li et al. (2011), "Reduced Graphene Oxide Electrically Contacted Graphene Sensor for Highly Sensitive Nitric Oxide Detection", 2011 ACS Nano.
Roham M et al. (2007), "Diamond microelectrodes and CMOS microelectronics for wireless transmission of fast-scan cyclic voltammetry", Conf Proc IEEE Eng Med Biol Soc., 2007: 6044-7.
Zhang J et al. (2013), "Cardiorespiratory biomarker responses in healthy young adults to drastic air quality changes surrounding the 2008 Beijing Olympics", 2013 Health Effects Institute Research Report, No. 174: 5-154.

* cited by examiner

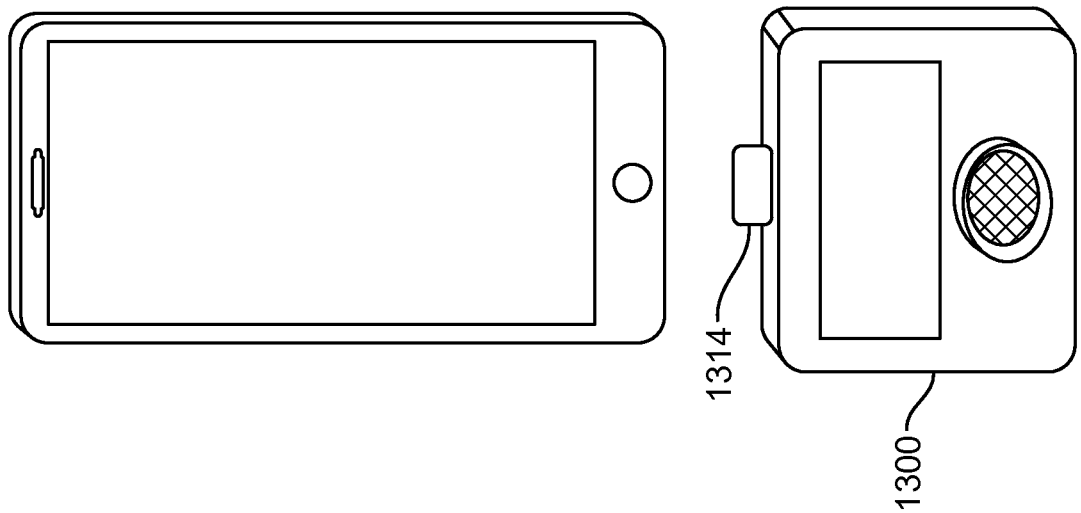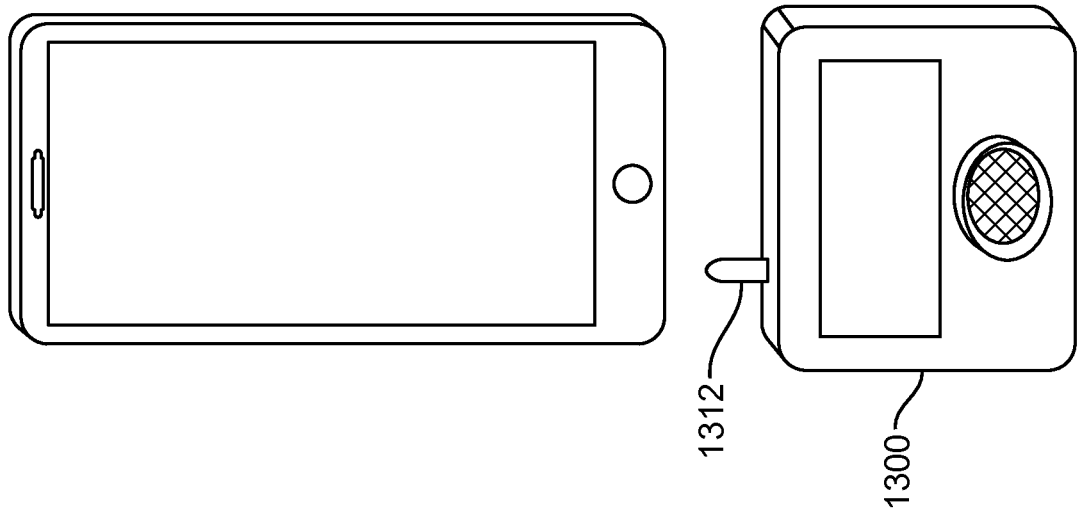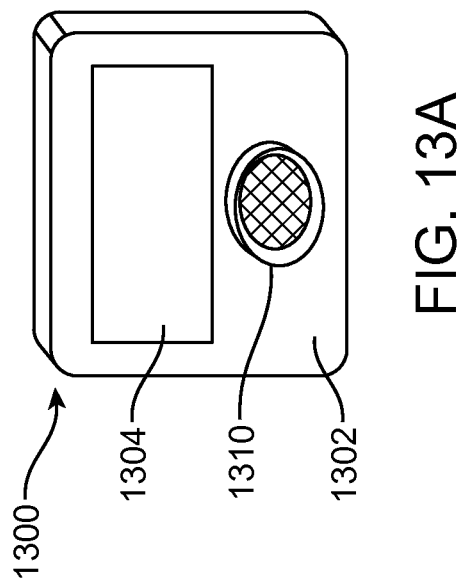

SYSTEMS AND METHODS FOR MONITORING RESPIRATORY FUNCTION

CROSS-REFERENCE TO RELATED APPLICATIONS

The present application is a U.S. national stage application under 35 U.S.C. § 371 of International Application No. PCT/US2014/063592, filed Oct. 31, 2014, which in turn claims the benefit of U.S. Provisional Patent Application No. 61/898,402, filed Oct. 31, 2013, and U.S. Provisional Patent Application No. 61/931,527, filed Jan. 24, 2014, the content of each of which is incorporated herein by reference in its entirety.

FIELD

The present disclosure relates generally to the fields of pulmonary health and medicine and specifically to portable devices, systems, and related methods for measuring and monitoring the health of the lungs and airways.

BACKGROUND

Asthma describes a chronic disorder in which the airways of an individual's lungs narrow in response to certain stimuli. The narrowing may occur from inflammation of the airways, excessive mucus secretion into the airways, and/or contractions of the muscles surrounding the airways. Asthmatic patients are susceptible to acute attacks, which may present symptoms such as coughing, wheezing, shortness of breath, and chest tightening. During severe attacks, a person's oxygen supply may become severely limited such that emergency assistance is required. With appropriate treatment, a person typically recovers completely from an acute attack. Asthma is a heterogeneous disorder, meaning the causes or triggers of symptoms vary among patients. Some of the more common triggers include: inhaled allergens, for example, animal dander, dust mites, and pollens; chemicals and irritants such as cigarette smoke, air pollutants, cleaning products, and perfumes; cold air; exercise; respiratory infections; stress; and anxiety. By some estimates, over 34 million people living in the United States have been diagnosed with asthma at some point in their lives, and the number continues to grow. Asthma is one of the most common chronic diseases among children, with some estimating that more than 7 million children in the U.S. have asthma. The impact on their lives can be significant. Asthma is one of the most common causes for childhood hospital admissions and one of the leading causes of school absenteeism. In the U.S., childhood asthma results in 14 million missed school days annually. The financial impact of asthma is also significant with asthma responsible for 11.5 million medical visits in the U.S. each year and $56 billion annually in health care costs due to emergency room visits, hospitalizations, prolonged medication regimens, and the like.

While there is no known cure for asthma, it generally can be managed and controlled. Current treatments often include daily or twice-daily administration of anti-inflammatory and/or bronchodilator drugs. These drugs are often administered via inhalation with the use of a metered-dose inhaler. For certain populations, particularly children, it is advised that inhalers be used in conjunction with spacers. Spacers require less coordination to use than an inhaler alone, and they increase the amount of drug successfully delivered to the lungs.

In addition, at the onset of an asthma attack, patients are often advised to administer a dose of a short-acting beta-adrenergic or other fast-acting drug via an inhaler or inhaler-spacer combination. For severe attacks, a patient may be advised to use a fast-acting inhaler multiple times, for example, up to three times, with rest between each use. When administered appropriately at the onset of the attack, the fast-acting drug will often be sufficient to cause the symptoms to subside. Overuse of the fast-acting inhaler may cause dangerous side effects such as cardiac arrhythmias, immunosuppression, elevated blood pressure, caustic damage and/or tissue scarring. Moreover, excessive use of the fast-acting inhaler often indicates the need for a more aggressive therapy, such as an orally-administered corticosteroid; when such a need is not recognized due to continued over-reliance on the fast-acting inhaler, the risk of asthma-related death increases.

Thus, frequent monitoring of both symptoms and inhaler use is extremely important; monitoring may identify and prevent over-use of fast-acting inhalers as well as lead to better day-to-day asthma management, thereby reducing the frequency and/or severity of asthma attacks. Similarly, it is important to monitor symptoms and inhaler use with other conditions of the lungs and airways, such as, for example, chronic obstructive pulmonary disease (COPD), emphysema, cystic fibrosis, and chronic bronchitis. Some people, including for example, athletes and vulnerable segments of the population, such as the elderly, the infirmed, and young children, may also find it beneficial to monitor lung function for fitness and wellness purposes or when in areas with elevated ground ozone levels, smog, or other air pollutants.

Despite the need, current options for monitoring asthma, other pulmonary conditions, and lung function are limited. For example, asthma patients often lack exact data on the frequency or duration of their asthma attacks and the frequency of their medication administration. Within the clinical setting, spirometry is the current gold standard for characterizing the severity of a patient's asthma. Spirometers are generally configured for clinical use and, therefore, are not useful for everyday monitoring except in extreme cases. A simple peak flow meter may be used in the home; however, the data provided from a peak flow meter is limited and the sensitivity of such devices is low. Moreover, while many asthmatics carry their inhaler with them outside the house, few carry a peak flow meter with them; thus, it is often not present during an attack to help determine the severity of the attack. For reasons such as these, asthma and other respiratory conditions continue to be relatively poorly monitored and poorly controlled disorders.

SUMMARY

There is a significant need for improved systems and related methods for monitoring respiratory health, and more generally, for monitoring lung function. For example, there is a significant need for improved asthma monitoring systems and techniques. In particular, there is a need for portable, handheld lung function monitoring systems. A need exists for devices, systems, and methods that allow individuals to monitor their own symptoms and overall lung function regularly, for example, daily, by users such as athletes. A need exists for devices, systems, and methods that allow individuals to monitor the effects of air pollution and other irritants on their lung function. A need also exists for devices, systems, and methods that allow patients with chronic respiratory conditions to conveniently track the occurrence of acute attacks of symptoms, the severity of acute attacks, and the frequency of inhaler usage. A need also exists for wireless electronic reporting of such data to a healthcare provider who can use the data to better advise the patient on recommended treatments and practices. Moreover, a need exists for a system that can predict the onset of a patient's acute symptoms and/or help the patient identify the onset of acute symptoms sooner. A need also exists for a system that can alert an individual when measures of lung and/or airway function are deviating from normal so that the individual may begin taking corrective measures. A need also exists for a system that can identify when dangerous levels of acute symptoms have been reached, and optionally, call an emergency contact or emergency services automatically. A need also exists for a system that can help a patient identify specific triggers of his or her acute symptoms. A need exists for systems and methods that lead to more personalized treatments, greater disease management, fewer hospital and emergency room visits, and reduced health care costs. Various embodiments disclosed herein may fulfill one or more of these needs.

One aspect of the present disclosure is directed to a portable, handheld measurement device for monitoring lung function. In certain embodiments, the measurement device includes a housing. The housing includes an aperture into which an individual can exhale or inhale. Air entering through the opening flows into an interior of the housing where one or more sensors are positioned. In some embodiments, the one or more sensors include one or more pressure sensors or other sensors designed to detect air flow properties such as the direction, flow rate, and/or volume of air flow. In some embodiments, the one or more sensors additionally include one or more volatile chemical sensors. In various embodiments, an amplification circuit is electrically coupled to the one or more sensors in the measurement device. The amplification circuit may include an amplifier, such as an operational amplifier or other differential amplifier to increase the power of the sensor signal. The amplification circuit of some embodiments may additionally include an analog-to-digital converter (ADC) and/or one or more filters. Thus, the amplification circuit may enable processing (i.e., isolation, amplification, and/or digitization) of the sensor signals.

In certain embodiments, the measurement device includes a processor electrically coupled to the amplification circuit. The processor of various embodiments is configured to format, process, and/or store processed signals received from the one or more sensors and amplification circuit. In some such embodiments, the processor of the measurement device is configured to calculate meaningful lung function measurements from pressure or airflow signals. The calculated lung function measurements may include breathing rate, Peak Expiratory Flow rate (PEFR), Forced Expiratory Flow (FEF) rate within specific intervals or fractions, for example FEF25-75%, Forced Expiratory Volume within a given time interval such as the first second (FEV1), Forced Vital Capacity (FVC), tidal volume, or other lung function measurements typically obtained in a clinical setting.

In other embodiments, the processor of the measurement device is configured to save the processed sensor signals as binary data or in a text file or other transmittable file. The processed sensor signals may still be in the form of pressure data, or the processor of the measurement device may have applied one or more equations to the raw sensor signal data such that the processed sensor signal data is in the form of flow and/or flow rate data. In some embodiments, the processor of the measurement device optionally adds corresponding location data and/or a time stamp to the processed sensor signals. In such embodiments, information indicative of the time and place of each recording is stored with each respective sensor signal recording. In some such embodiments, the processor of the device generates the time stamp. Additionally or alternatively, the measurement device may include a GPS detection unit to generate the location data. The transmittable data of some embodiments is transmitted to a remote computing device in wired or wireless communication with the measurement device, and the remote computing device performs data analysis, calculating, for example, various spirometry measurements.

In certain embodiments, the measurement device also includes an attachment feature for attaching the housing to another apparatus such as, for example, a smartphone or other remote computing device, a spacer, or an inhaler. The attachment feature may be shaped for coupling to one or more such apparatuses. For example, in some embodiments, the device may have an opening sized, positioned, and configured to couple to an inhaler and/or a spacer, or it may have a plug sized, positioned, and configured to fit within a headphone jack, an electrical charging port, and/or a data port (e.g., a USB or micro-USB port) of a smartphone, tablet, laptop, personal computer, or other remote computing device. In other embodiments, the device may have multiple attachment features to allow for coupling with a plurality of different apparatuses. In some embodiments, one or more of the attachment features are removable and interchangeable, allowing the device to couple interchangeably to various apparatuses.

A further aspect of the present disclosure relates to a handheld device for monitoring and treating respiratory conditions such as, for example, COPD or asthma. In some embodiments, the device includes a housing that has an open proximal end and a distal end having an attachment feature. The attachment feature is configured to couple the housing, directly or indirectly, to an aerosol medicine dispensing canister. The housing defines a lumen extending between the proximal end and the distal end. The device further includes: a pressure sensor coupled to the housing and configured to detect a pressure differential within the lumen, and optionally, a volatile chemical sensor disposed within the housing and configured to detect levels of a volatile chemical within the lumen. In some embodiments, the volatile chemical is a biomarker, such as, for example, nitric oxide, and the volatile chemical sensor is a biomarker sensor, such as, for example, a nitric oxide sensor.

In some embodiments, the open proximal end of the device is shaped as a mouthpiece and sized to fit within the mouth of a patient. In some embodiments, the device additionally includes a mesh extending across a location of the lumen, wherein the pressure sensor detects the pressure differential on opposing sides of the mesh. In some embodiments, the pressure sensor includes a strain-based variable reluctance sensor. In some embodiments, the mesh is removable and replaceable. The pressure sensor may be removable with the mesh. In some embodiments in which a nitric oxide sensor is present, the nitric oxide sensor includes a Clark electrode and/or a reduced graphene oxide electrically contacted sensor.

In some embodiments, the device also includes a circuit connected to the pressure sensor and/or the chemical sensor. In such embodiments, the circuit at least includes an analog-to-digital converter, a power source, a microprocessor, and a wireless transmitter.

In some embodiments, the housing is formed, at least in part, of an inhaler mouthpiece. In other embodiments, the housing is formed, at least in part, of a spacer. In such embodiments, the housing may indirectly couple to the aerosol medicine dispensing canister. In some such embodiments, the attachment feature includes a slot configured to receive a proximal end of an inhaler mouthpiece. In other embodiments, the housing is a separate component that is attachable to an existing apparatus, such as, for example, an inhaler or spacer. For example, in some embodiments, the attachment feature of the housing attaches to an inhaler mouthpiece, and in some embodiments, the attachment feature of the housing attaches to a spacer mouthpiece.

Another aspect of the disclosure relates to a system for monitoring lung function, for example, in order to monitor: a respiratory condition such as COPD or asthma, cystic fibrosis, allergic inflammation, hyper-reactivity, and/or the effects of exercise or air pollution. In various embodiments, the system includes a handheld measurement device, such as any of the devices described herein, and a remote computing device. The remote computing device of some embodiments includes: an input/output (I/O) device, a processor, and memory. In some embodiments, the remote computing device also includes a display interface. In various embodiments, the remote computing device is a mobile computing device such as a smart-watch, smartphone, or tablet, a laptop computer, or a desktop computer. In some embodiments, the remote computing device is a specialized computing device attached, for example, to a keychain, lanyard, necklace, or a clip for attachment to clothing. In some embodiments, at least one I/O device is a wireless receiver and transmitter; in such embodiments, the remote computing device is configured for wireless communication with the handheld measurement device and/or a remote server. The means of wireless communication may include, but is not limited to, a mobile WiMAX network, LTE network, Wi-Fi® network, radiofrequency signals, Bluetooth® signals, and/or near field communication technology. In some embodiments, at least one I/O device provides for a wired connection between the handheld measurement device and the remote computing device and may include a TRS plug, USB, micro-USB, mini-USB, or other plug, port, or other connection.

In some embodiments of the system, the memory of the remote computing device stores instructions executable by the processor, which when executed by the processor, cause the remote computing device to perform a method. The computer-implemented method of some such embodiments includes: receiving a pressure differential signal, and optionally, a volatile chemical level signal from the handheld measurement device via the remote computing device's I/O device. The method further includes analyzing and storing the signals and/or transmitting the signals to a server for analysis and storage. The server may include, for example, a database server, an application server, and/or a web server. Data stored within the server may be retrievable by the remote computing device, and optionally, may be retrievable by other connected computing devices that are granted access. In some non-limiting embodiments, the signals are transmitted to the server over a cellular network or over Wi-Fi.

An additional aspect of the disclosure is directed to a method for monitoring lung function. In various embodiments, the method is performed by a computer processor and includes receiving and recording a differential pressure signal, and optionally, a volatile chemical level signal. In some embodiments of the method, the one or more recorded signals are monitored to identify significant deviations from an initial baseline signal, for example, an increase in the amplitude of the received signal of at least 0.5 L/s. In various embodiments, such a change in signal is indicative of a breath.

In some embodiments, the computer processor identifies whether a breath was an inhalation or expiration based at least in part on the differential pressure signal. For example, in some embodiments, if a change in the differential pressure signal is negative, the recorded breath is identified as an inhalation, and if a change in the pressure differential signal is positive, the recorded breath is identified as an exhalation. In other embodiments, depending on the configuration of the sensors, the opposite relationship may be true. In some embodiments, if an inhalation is identified, a drug dosage counter is incremented. In some embodiments, if an expiration is identified, air flow rate and volume metrics are calculated from the differential pressure signal, a volatile chemical level is determined from the volatile chemical level signal, if received, and data indicative of the air flow rate, volume metrics, and optionally, volatile chemical levels, are stored in a database. In some such embodiments, the volatile chemical is nitric oxide or other cardiorespiratory biomarker.

In some embodiments, the method additionally includes comparing the data to baseline values and/or a patient's historical data to identify trends and/or data of potential concern. In some embodiments, the method also includes transmitting or displaying an alert to a user. Additionally or alternatively, the method includes transmitting or displaying data indicative of the air flow rate, volume metrics, and optionally, volatile chemical levels to a user.

Such a method may be performed by a processor located within a handheld measurement device that is in wired connection with the differential pressure sensor and the optional volatile chemical sensor. Alternatively, such a method may be performed by a processor located within a remote computing device, such as a smartphone, smart wearable, tablet, or laptop, which is, at least occasionally, in wired or wireless communication with the handheld measurement device. In embodiments in which the remote computing device and handheld measurement device are only in periodic or occasional communication with each other, the handheld measurement device must include memory configured to store differential pressure signal data, and optionally, volatile chemical level signal data, between communication sessions. In some embodiments, data indicative of the location and/or the date and time of each pressure reading are also generated and stored by the memory of the handheld measurement device. In other embodiments, all or portions of the method described above are performed by a server, such as, for example, a web server, application server, and/or database server.

BRIEF DESCRIPTION OF THE DRAWINGS

FIGS. 13A-13C depict various additional embodiments of portable measurement devices for monitoring lung function.

FIGS. 22A-H depict various embodiments of graphical user interfaces displayed on a remote computing device of a patient in accordance with principles of the present disclosure.

FIGS. 23A-C depict various embodiments of graphical user interfaces displayed on a remote computing device of a physician in accordance with principles of the present disclosure.

DETAILED DESCRIPTION

Figure 1:
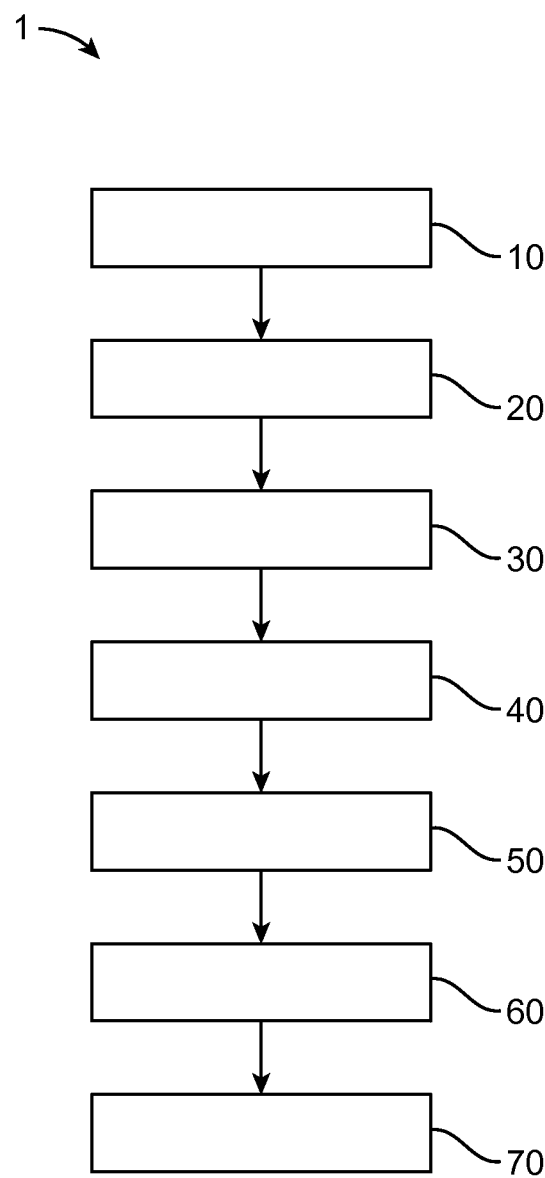
FIG. 1 depicts a functional block diagram of one embodiment of a handheld measurement device for monitoring lung function and treating respiratory conditions.

In the following detailed description, reference is made to the accompanying drawings, which form part of the present disclosure. The embodiments described in the drawings and description are intended to be exemplary and not limiting. As used herein, the term "exemplary" means "serving as an example or illustration" and should not necessarily be construed as preferred or advantageous over other embodiments. Other embodiments may be utilized and modifications may be made without departing from the spirit or the scope of the subject matter presented herein. Aspects of the disclosure, as described and illustrated herein, can be arranged, combined, and designed in a variety of different configurations, all of which are explicitly contemplated and form part of this disclosure.

Unless otherwise defined, each technical or scientific term used herein has the same meaning as commonly understood by one of ordinary skill in the art to which this disclosure belongs. In accordance with the claims that follow and the disclosure provided herein, the following terms are defined with the following meanings, unless explicitly stated otherwise.

The term "about" or "approximately," when used before a numerical designation or range (e.g., pressure or dimensions), indicates approximations which may vary by (+) or (−) 5%, 1% or 0.1%.

As used in the specification and claims, the singular form "a", "an" and "the" include both singular and plural references unless the context clearly dictates otherwise. For example, the term "a sensor" may include, and is contemplated to include, a plurality of sensors. At times, the claims and disclosure may include terms such as "a plurality," "one or more," or "at least one;" however, the absence of such terms is not intended to mean, and should not be interpreted to mean, that a plurality is not conceived.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a device or method consisting essentially of the elements as defined herein would not exclude other materials or steps that do not materially affect the basic and novel characteristic(s) of the claimed invention. "Consisting of" shall mean that the devices, systems, and methods include the recited elements and exclude anything more than a trivial or inconsequential element or step. Embodiments defined by each of these transitional terms are within the scope of this disclosure.

"Component," as used herein, may refer to an individual unit or structure, or it may refer to a portion, feature, or section of a larger structure.

"Asthma" shall refer to a chronic disorder characterized by one or more episodes of reversible airway constriction.

As used herein, the term "hyper-reactivity," in one aspect, refers to bronchial hyperresponsiveness or other airway hyper-reactivity. This is a state characterized by easily triggered bronchospasm. Hyper-reactivity may be a symptom of asthma, chronic obstructive pulmonary disease (COPD), infection, cystic fibrosis, or other respiratory condition.

An "acute attack" or "attack of symptoms" shall refer to an asthma attack or other acute escalation of respiratory-related symptoms such as coughing, wheezing, airway inflammation and/or narrowing, secretion of mucus in the airways, shortness of breath, and/or chest tightening.

An "inhaler" shall refer to a metered-dose inhaler, which is a medical drug delivery system. The metered-dose inhaler is a handheld mouthpiece coupled to a cartridge containing medicine and a pressurized gas. By pumping and/or pushing down on the cartridge, the medicine is expelled from the inhaler as an aerosol that can be inhaled. Such a device allows for targeted delivery of medicine to the lungs and airways.

A "fast-acting inhaler" shall refer to an inhaler containing one or more particular medicines intended for the treatment of acute respiratory symptoms.

A "spacer" shall refer to a medical drug delivery system that may be used in conjunction with an inhaler. A spacer is designed to securely couple to an inhaler and includes a mouthpiece and a chamber. The chamber is configured to hold aerosolized medicine that has been dispensed from the inhaler so that a patient may more easily and/or effectively breathe the medicine into his or her lungs.

A "cardiopulmonary biomarker" shall refer to any volatile chemical produced and/or released by the cardiopulmonary system in response to certain stimuli, disease states, or physical changes within the body. In particular, the cardiopulmonary biomarkers referred to herein are gaseous molecules produced by an individual in response to, or in connection with, changes in lung function, and which are expired by an individual during exhalation.

As used herein, "patient" shall mean any individual who receives treatment for a respiratory condition such as, but not limited to, asthma or COPD, regardless of whether the treatment is received regularly or on an intermittent basis. For ease of reference, "patient," as used herein, may additionally or alternatively refer to athletes or other individuals who track their lung function using the systems, devices, and methods described herein.

As used herein, a "user" shall refer to any individual who interacts with, or otherwise uses, any of the systems or devices disclosed herein. For example, a user may be a patient using the device, a parent or guardian assisting or monitoring the patient, or a healthcare provider or healthcare technician reviewing data generated by the system.

As used herein, "distal" and "proximal" are relational terms, wherein "proximal" refers to a portion of a medical device that is relatively closer to the patient and "distal" refers to a portion of a medical device that is relatively farther from the patient. For example, the proximal end of a spacer is the end configured to be inserted into a patient's mouth and the distal end is the end configured to be held out a distance from the patient's mouth.

Various embodiments disclosed herein are directed to a portable, handheld device for monitoring lung function and respiratory conditions. The device of some embodiments monitors, for example, the frequency and severity of asthma attacks and/or acute attacks of symptoms in patients with other respiratory conditions. Some embodiments of the device are particularly advantageous for monitoring and treating asthma in children, particularly children ages 5-12; however, the embodiments described herein are also contemplated, and intended, for use by individuals of all ages who: suffer from asthma or other respiratory conditions, are sensitive to poor air quality, and/or wish to track lung performance for fitness or wellness purposes. Various devices and systems disclosed herein are configured to provide information to clinicians, patients, and caregivers in order to improve the personalization of treatment and the predictability of respiratory symptom attacks. One of ordinary skill in the art of pulmonary medicine will appreciate that while some embodiments disclosed herein are directed to the monitoring and treatment of asthma for the sake of simplicity of the description, all such embodiments may also be used to monitor and treat chronic obstructive pulmonary disease (COPD) or other respiratory conditions and may also be used to monitor lung function more generally.

The device of some embodiments is in the form of: an improved inhaler or spacer; an attachment to an inhaler, spacer, smartphone, or other portable device; or a separate, stand-alone portable device, having components that allow it to acquire meaningful data for lung function monitoring. In various embodiments, such a device forms a component of a system configured to display lung function monitoring information in a manner that is meaningful to a lay user, such information being based, at least in part, on the data acquired from the device. With such information, a user may be able to take actionable steps to avoid or minimize the severity of a future or current attack of symptoms. The portability and simplicity of the devices provided herein, as well as the meaningful and easy-to-interpret nature of the results generated by such devices, are at least some of the features that make the provided devices suitable for everyday use—including use outside of a clinic.

The current gold standard metrics for assessing lung function and the severity of asthma and other respiratory conditions within the clinical setting are flow rate and lung volume readings, which are largely obtained from spirometers. The output generated by clinical spirometers is typically in the form of a graphical volume-time curve or a graphical flow-volume loop that charts the rate of airflow versus the total volume expired. The graphical output is generally difficult to read, requiring interpretation by a clinician or technician. Moreover, spirometers are generally bulky, non-portable, and configured for placement within a clinic.

In addition to spirometry readings, growing research indicates that certain cardiopulmonary biomarkers, such as, for example, nitric oxide, may be useful in monitoring and evaluating respiratory conditions. Some cardiopulmonary biomarkers, such as nitric oxide, fluctuate significantly based on the level of inflammation of the airways. It is believed that nitric oxide testing may be a valuable predictor of an acute attack of respiratory symptoms when used in tandem with spirometry. Healthy people have nitric oxide levels in their breath in the low twenties parts per billion, while asthma patients, as an example, typically have values over thirty parts per billion after suffering from an asthma attack. When values of nitric oxide levels are coupled with spirometry readings, more accurate information may be deduced regarding the severity of an acute attack. Such values would provide beneficial information, if tracked over time.

Accordingly, some embodiments described herein integrate a plurality of components into a portable medicine delivery system in order to achieve, effectively, a miniaturized spirometer, and optionally, a miniaturized nitric oxide detection unit or other biomarker detection unit in one easy-to-use device. In various embodiments, such components and functionality are integrated into, or attach to, an inhaler or spacer, each of which is an object that is already well-known, owned, and used by many asthma sufferers. In some embodiments, spirometry, and optionally, nitric oxide detecting, components are integrated directly into a modified inhaler or housed in a device that attaches directly to an existing inhaler. In other embodiments, the components are integrated into a spacer or housed in a device that attaches directly to an existing spacer. Spacers are often coupled to, and used in conjunction with, an inhaler, particularly in pediatric asthmatic populations. A spacer allows for a more gradual flow and intake of asthma medication into the lungs of a patient. The integration of the measurement components into the spacer, rather than the inhaler, provides extra space for the installation of the desired measurement components. This may simplify the manufacturing process, yielding a lower-cost product. Additionally, the measurement components in the spacer may advantageously encourage more use of the spacer; use of the spacer is recommended because patients achieve greater delivery of asthma drugs to their lungs when using a spacer. Moreover, directing exhalation into the larger volume of the spacer versus direct exhalation into the inhaler may help minimize the concentration of condensation deposited on the measurement components, thereby preserving the accuracy of the components.

Other embodiments described herein integrate a plurality of components into a portable monitoring system in order to achieve, effectively, a miniaturized spirometer, and optionally, a miniaturized nitric oxide detection unit or other biomarker detection unit in one compact, easy-to-use device that is able to physically attach and/or wirelessly sync to a smartphone, tablet, laptop, or other portable computing device.

As shown in the functional block diagram of FIG. 1, in various embodiments, a measurement device 1 for monitoring lung function includes some of, all of, or at least, the following components: a mouth-engaging component 10, a spirometry component 20, a cardiopulmonary biomarker detection component 30, a medicine delivery component 40, a signal processing component 50, a calibration component 60, and a data storage component 70. These components are functional components rather than physical components, and as such, one structural element may perform a plurality of these functions and/or multiple structural elements may work together to perform a single function.

The mouth-engaging component 10 of various embodiments includes a mouthpiece. In some embodiments, the mouthpiece is shaped as a tube having an outer surface on which the lips of a patient can rest. In other embodiments, the mouthpiece is shaped as a mask configured to surround the nose and mouth of a patient. The mask is contoured to fit against a patient's face, and in some embodiments, offers a tight seal to the face of the wearer. In various embodiments, the mouthpiece includes and defines an opening through which air can flow from the mouth of the patient into the measurement device 1 and through which air and medicine can flow from the measurement device 1 into the mouth of the patient. In other embodiments, the mouth-engaging component 10 is simply an aperture into which an individual can inhale or exhale. In some embodiments, the mouth-engaging component 10 is removable and exchangeable; it can be removed for cleaning or replaced between uses. In other embodiments, the mouth-engaging component 10 is integrally (i.e., monolithically) formed with or bonded to other portions of the measurement device 1.

The spirometry component 20 of various embodiments includes sensors and/or other components that directly or indirectly sense the flow rate and volume of expired air expressed through the mouthpiece of the measurement device 1. One or more of the following metrics are able to be calculated based on data acquired by the spirometry component: Peak Expiratory Flow rate (PEFR), Forced Expiratory Flow (FEF) rate, Forced Expiratory Volume within a given time interval such as the first second (FEV1), Forced Vital Capacity (FVC), tidal volume, residual volume, breathing rate, and ventilation rate. In some embodiments, these one or more metrics are calculated by the signal processing component 50 or by a remote (i.e., separate, external) computing device, but such calculations are made possible by the signals generated or detected by the spirometry component 20. In some embodiments, the metric sensed by the spirometry component 20 is a differential pressure within the measurement device 1. In such embodiments, the differential pressure correlates to a flow rate and volume. In other embodiments, one or both of a flow rate and a volume may be detected directly by the spirometry component 20.

In one embodiment, the spirometry component 20 is formed of a pneumotachometer comprising a fine mesh (i.e., an air-permeable screen) and one or more pressure sensors. In such an embodiment, the mesh is positioned across an entire cross-sectional area of a lumen within the measurement device 1. When a patient moves air into the measurement device 1 by exhaling into the mouth-engaging component 10, the air flow encounters resistance at the location of the mesh, causing the air flow to lose energy in the form of pressure and velocity. As long as the airflow is laminar and the mesh is the only cause for changes to the flow, the resultant change in pressure is directly proportional to the flow rate. The scaling factor can be derived empirically through calibration, as described further below. Accordingly, in some embodiments, pressure sensors are provided on opposing sides of the mesh in order to detect the pressure differential across the mesh. The pressure signals from each pressure sensor may be transported to an amplification circuit and inboard processor for processing.

In another embodiment, the spirometry component 20 is formed of a portion of a measurement device 1 having a change in lumen size from a first diameter to a second diameter and one or more pressure sensors. In one embodiment, a first pressure sensor is positioned at a site within the measurement device 1 having the first diameter and a second pressure sensor is positioned at a site within the measurement device 1 having the second diameter. In such an embodiment, as airflow moves from a region with the first diameter to a region with the second diameter, the airflow encounters resistance, suffering a loss of energy and a pressure drop. Such resistance to the airflow can be expressed as:

$$C_c = 1,6 \sin\frac{\theta}{2}; \text{ for } \theta \leq 45°$$

$$C_c = \sqrt{\sin\frac{\theta}{2}}; \text{ for } 45 \leq \theta \leq 180°$$

$$K_1 = C_c \cdot 0.5 \cdot (1-\beta^2)^2 = 0.8 \sin\frac{\theta}{2}(1-\beta^2)^2; \text{ for } \theta \leq 45°$$

$$K_1 = C_c \cdot 0.5 \cdot (1-\beta^2)^2 = 0.5\sqrt{\sin\frac{\theta}{2}}(1-\beta^2)^2; \text{ for } 45° \leq \theta \leq 180°,$$

where K1 is the resistance factor, $\beta$ is the diameter ratio $d_1/d_2$, and $\theta$ is the angle at which the two diameters ($d_1$ and $d_2$) connect together. As with the pneumotachometer embodiment described above, the pressure differential detected between the first and second pressure sensors is proportional to the flow rate through the measurement device 1, and thus, detection of the pressure differential allows the flow rate and volume to be determined.

In another embodiment, the spirometry component 20 is formed of an ultrasonic transducer, which indirectly measures airflow by detecting differences in the amount of time it takes for a pulse of ultrasound to travel in opposite directions across a path of airflow. The velocity of sound in a medium is relative to the flow of the medium, as described by the following Galilean transformation of the Cartesian coordinates and time: $x'=x-vt$, $y'=y$, $z'=z$, and $t'=t$, where the airflow is moving in the x direction at speed v. Thus, when a sound wave is traveling in the direction of the flow, it will reach the sensor faster than when it is traveling against the flow. The difference in time that it takes for the sound to travel in opposing directions correlates to the flow rate of the exhaled air. Signals received by a processor from the ultrasonic transducer can thus be used to quantify airflow rate and volume.

In yet another embodiment, the spirometry component 20 is formed of a turbine. In such an embodiment, as air flows through the measurement device 1, it pushes against the turbine blades. The number of rotations of the turbine is proportional to the volume of air passing through, and the frequency of rotation is proportional to the flow rate. The turbine's rotation can be measured mechanically or by measuring the passage of an infrared light through the blade. A processor can then use this data to calculate the airflow rate and volume.

The cardiopulmonary biomarker detection component 30 is present in some, but not all embodiments. The cardiopulmonary biomarker detection component 30 of some embodiments includes one or more sensors calibrated to sense levels of one or more cardiopulmonary biomarkers present within the measurement device 1 during and/or immediately following a patient's expiration of air into the mouth-engaging component 10 of the device 1.

As explained above, levels of exhaled nitric oxide have been found to fluctuate significantly based on the level of inflammation in an individual's airways; consequently, exhaled nitric oxide levels may provide valuable information about the severity of an asthma attack or other acute attack. Additionally, exhaled nitric oxide levels have been found to fluctuate significantly based on air quality, as described in Zhang J et al., "Cardiorespiratory Biomarker Responses in Healthy Young Adults to Drastic Air Quality Changes Surrounding the 2008 Beijing Olympics," 2013 *Health Effects Institute Research Report*, No. 174: 5-154, the disclosure of which is herein incorporated by reference in its entirety. Thus, in some embodiments, the cardiopulmonary biomarker sensor is a nitric oxide sensor. The inclusion of a nitric oxide sensor may provide valuable, personalized information about the severity of acute attacks and/or an individual's sensitivity to indoor and outdoor air pollution. Such a sensor may help individuals track the frequency and severity of asthma attacks or other acute respiratory attacks and also track how their bodies are personally affected by their local air quality.

In some such embodiments, the nitric oxide sensor is a Clark electrode. In other embodiments, the nitric oxide sensor is a graphene oxide-electrically-contacted sensor or other suitable sensor. In some embodiments, a solid state nitric oxide sensor is used, such as the sensor described in Hunter G W et al., "Smart sensor systems for human health breath monitoring applications", 2011 *J. of Breath Res.*, 5: 1-11, the disclosure of which is herein incorporated by reference in its entirety.

In other embodiments, the cardiopulmonary biomarker detection component 30 is formed of a different volatile biomarker sensing apparatus. Volatile biomarkers known to be associated with respiratory conditions such as asthma include, for example: nitric oxide, pentane, ethane, 8-isoprostane, cysteinylleukotrienes, prostaglandin E2, hydrogen peroxide, aldehydes, nitrotyrosine, cytokines, and Leukotriene B4. With an appropriate sensing apparatus, one or more of these biomarkers may be detected in human breath in order to monitor for adverse effects caused by poor air quality and/or to diagnose or monitor the severity of asthma or other respiratory condition. In some embodiments, the volatile sensing apparatus is an electronic nose, such as for example, a Metal Oxide Semiconductor (MOS), a metal oxide semiconducting field effect transistors (MOSFET), or optical sensors, or any other electronic nose described in Chen, et al., "Applications and Technology of Electronic Nose for Clinical Diagnosis," *Open Journal of Applied Biosensor*, 2013, 2: 39-50, which disclosure is herein incorporated by reference in its entirety. In a preferred embodiment, the volatile sensing apparatus is a conducting polymer sensor (CP). In some embodiments, the nitric oxide detection component itself is an electronic nose, for example, a CP sensor, configured to detect the level of nitric oxide in the measurement device.

The medicine delivery component 40, present in some embodiments, includes a coupling feature, such as a valve and/or a receiving space. The coupling feature connects the measurement device 1 directly or indirectly to a drug-filled canister and enables the release of the drug into the measurement device 1. In some embodiments, the medicine delivery component 40 includes a metering valve designed to couple directly to the canister. In other embodiments, the medicine delivery component 40 includes a receiving space configured to receive an inhaler comprising an actuator body, metering valve, and the canister.

The signal processing component 50 receives inputs in the form of signals from the sensors of the spirometry component 20 and/or the cardiopulmonary biomarker detection component 30 and converts them into formatted signals, processed signals, and/or useful data. In some embodiments, the signal processing component 50 includes a circuit which filters, amplifies, and/or digitizes the sensor signals. In some such embodiments, the circuit includes, for example, a band pass, low pass, and/or high pass filter to remove noise present at frequencies outside of the expected frequency range of the sensor signals. In some embodiments, the circuit additionally or alternatively includes an amplifier such as an operational amplifier or other differential amplifier to increase the power of the sensor signals. In some embodiments, the circuit additionally or alternatively includes an analog-to-digital converter (ADC), which converts analog signals from the sensors into digital signals for transmission to a processor.

In some embodiments, the signal processing component 50 includes an inboard processor in direct or indirect wired connection with the one or more sensors. In some embodiments of the signal processing component 50, the inboard processor calculates one or more spirometry measurements from the digital data received from the circuit.

Alternatively, in other embodiments, the processor is configured to convert the digital data from the circuit into a text file or other transmittable file format to facilitate transmission of the data to a remote computing device. In some embodiments, the signal processing component 50 stores each record of sensor readings with a time stamp indicating when the reading took place. The inboard processor may generate the time stamp. In some embodiments, the signal processing component 50 stores each record of sensor readings with corresponding location data indicating where the reading took place. In such embodiments, the inboard processor is electrically coupled to a GPS sensor. In some embodiments, the signal processing component 50 also includes a radiofrequency (RF) transmitter such as, for example, a Bluetooth transmitter, for wireless transmission of data to a remote computing device. In at least some such embodiments, the remote computing device performs the spirometry calculations.

The calibration component 60 of various embodiments, is provided to ensure spirometry readings generated from the measurement device 1 are accurate. Conventionally, readings generated by spirometers become inaccurate over time. For example, with repeated use, the device's processor may heat up, increasing the temperature within the spirometer and/or humidity from the breaths of patients may build up within the device. Accordingly, conventional clinical spirometers need to be recalibrated periodically. Generally, a calibration syringe of know volume, for example, a 3 L calibration syringe, is used at least daily to recalibrate. The known volume (e.g., 3 L) is expelled into the spirometer, and the processor identifies what, if any, adjustment factor (i.e., scaling factor) is needed to make the reading equal 3 L. The adjustment factor may then be applied to all readings generated by the processor until the next time the spirometer is recalibrated.

In some embodiments provided herein, the calibration component 60 includes an inboard processor configured to perform a calibration procedure, which identifies an adjustment factor upon coupling to a calibration syringe. In other embodiments, the processor is configured to automatically zero out (i.e., generate a new baseline) before each use, such that environmental changes do not influence the readings. In still other embodiments, an atmospheric pressure sensor, humidity sensor, and/or temperature sensor are provided in the measurement device 1, and the processor is configured to automatically recalibrate its adjustment factors according to known relationships based on detected environmental changes.

The measurement device 1 of various embodiments further includes a data storage component 70. The data storage component 70 of some embodiments is formed of external or internal memory, for example, memory forming part of, or coupled to, an inboard processor. The data storage component 70 of various embodiments stores instructions, for example, instructions for converting received sensor signals into a text file or other transmittable file format. The memory may also store instructions that cause the inboard processor to collect and add accompanying date, time, and/or location information to each recording of sensor signals. In some embodiments, the data storage component 70 stores collected sensor signals, and optionally, any accompanying date, time, and/or location information, at least until the measurement device 1 is able to communicatively couple, and transmit data, to a remote computing device. In some embodiments, the data storage component 70 stores baseline calibration data and a calibration algorithm for use by the calibration component 60.

Figure 2:
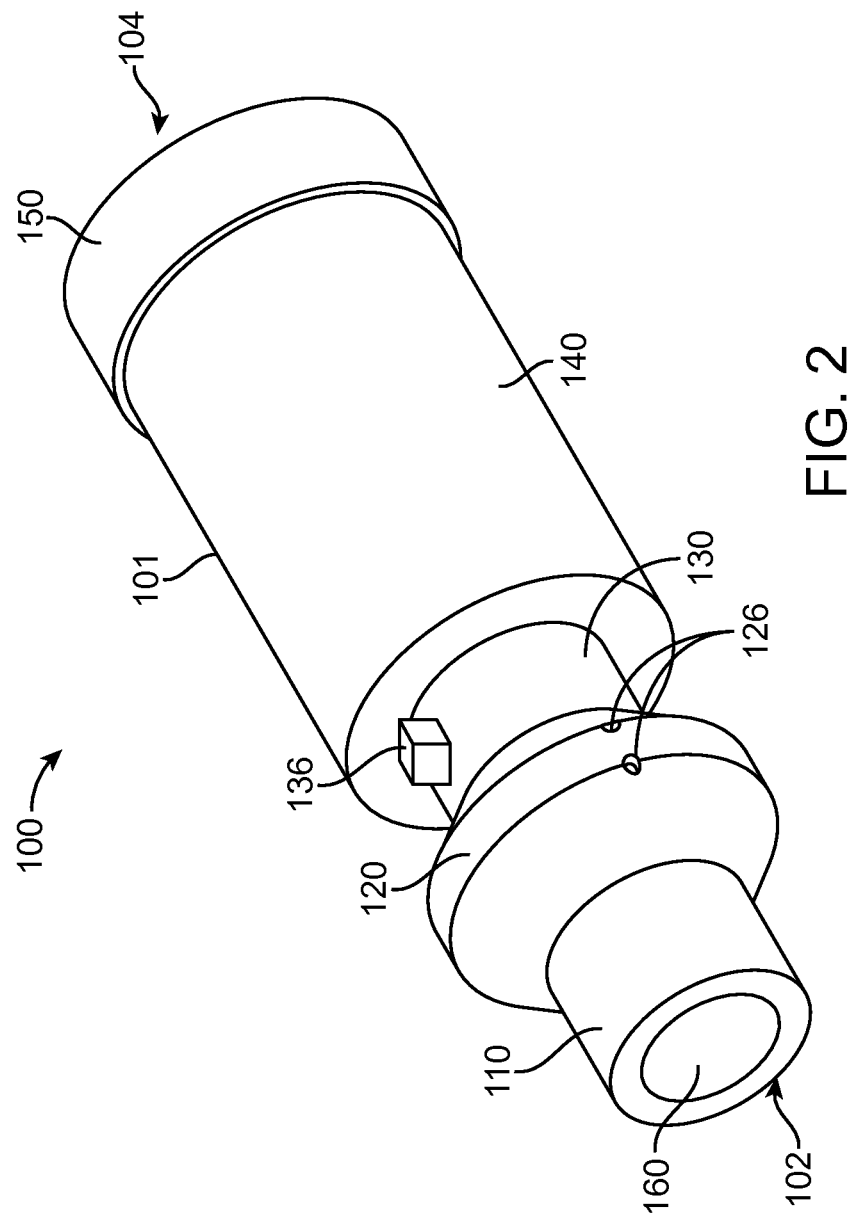
FIG. 2 depicts a schematic perspective view of one embodiment of a handheld measurement device, including a mouthpiece, a flow head, a sensor housing, a holding chamber, and a cover.

An exemplary embodiment of a measurement device is provided in FIG. 2. In the depicted embodiment, the measurement device 100 is in the form of an improved spacer having a proximal end 102 and a distal end 104. The measurement device 100 has a hollow or substantially hollow body 101 defined by a plurality of sections or features, including a mouthpiece 110, a flow head 120, a sensor housing 130, and an aerosol holding chamber 140. In some embodiments, each of these features has an open distal end, an open proximal end, and a lumen extending therethrough. Moreover, these features are all directly or indirectly coupled together and share a common lumen 160. In some embodiments, these features of the body 101 form a singular molded structure. In other embodiments, one or more of the features are molded separately then fixedly fused, welded, adhered, or otherwise secured together. In other embodiments, the mouthpiece 110, flow head 120, and sensor housing 130 are formed separately from the holding chamber 140 and can later be securely, but removably, coupled to the holding chamber 140. In other embodiments, any or all components may be separably coupled together, for example, by a friction fit or complementary threaded fit. In some embodiments, a first portion of the flow head 120 may be separably and reversibly coupled to a second portion of the flow head 120 such that, when detached, a mesh component within the flow head 120 is accessible for replacement. In some embodiments, a distal end of the mouthpiece 110 directly couples to a proximal end of the flow head 120, a distal end of the flow head 120 directly couples to a proximal end of the sensor housing 130, and a distal end of the sensor housing 130 directly couples to a proximal end of the holding chamber 140. In other embodiments, the sensor housing 130 may be proximal to the flow head 120, distal to the holding chamber 140, or integrated into or otherwise attached to the flow head 120.

The depicted measurement device 100 of FIG. 2 also includes a distal cover 150, coupled to the distal end of the holding chamber 140. In some embodiments, the cover 150 is integrally molded (i.e., monolithically formed) with the distal end of the holding chamber 140, such that the entrance to the lumen 160 at the distal end 104 of the body 101 is fully or substantially closed. In other embodiments, such as the embodiment depicted in FIG. 2, the cover 150 is a separately formed element, which may be fixedly fused, welded, or adhered to the holding chamber 140 or removably coupled to the holding chamber 140 to increase ease of cleaning the device 100. The connection between the cover 150 and the holding chamber 140 is air-tight. The cover 150 includes a hole, slot, or other coupling feature for securely receiving a portion of an inhaler.

In various embodiments, the body 101 is formed of a polymer, such as, for example, a hard plastic, that is safe for medical use and able to withstand the chemicals found within asthma medicines. In some embodiments, the body 101, or portions of the body, such as, for example, the holding chamber 140, has anti-static properties to minimize the deposition of aerosolized droplets of medicine on the inner surface of the body 101 or body portion. For example, in one embodiment, all or portions of the body 101 are formed of anti-static acrylonitrile butadiene styrene. In various embodiments, all or a portion of the cover 150 is formed of a soft, flexible, and/or resilient polymer, for example, rubber. In some embodiments, all or portions of the mouthpiece 110, flow head 120, and/or sensor housing 130 are formed of a relatively soft, resilient polymer.

In FIG. 2, the tubular mouthpiece 110 is sized to allow for comfortable positioning within a patient's mouth. In some embodiments, the mouthpiece 110 is particularly sized to fit within a child's mouth; in other embodiments, the mouthpiece 110 is sized for an adult or sized such that one size fits into all mouths. In some embodiments, the mouthpiece is removable for cleaning and/or replacement. In some such embodiments, the mouthpiece is interchangeable so that a single measurement device can be safely and hygienically used by a plurality of patients. The mouthpiece 110 is formed of a wall having an outer surface on which a patient's lips can rest and an inner surface defining a lumen 160 through which the patient can exhale air and inhale air and aerosolized medicine. A cross-section of the mouthpiece lumen 160 may be an oval or any other suitable shape.

Figure 3:
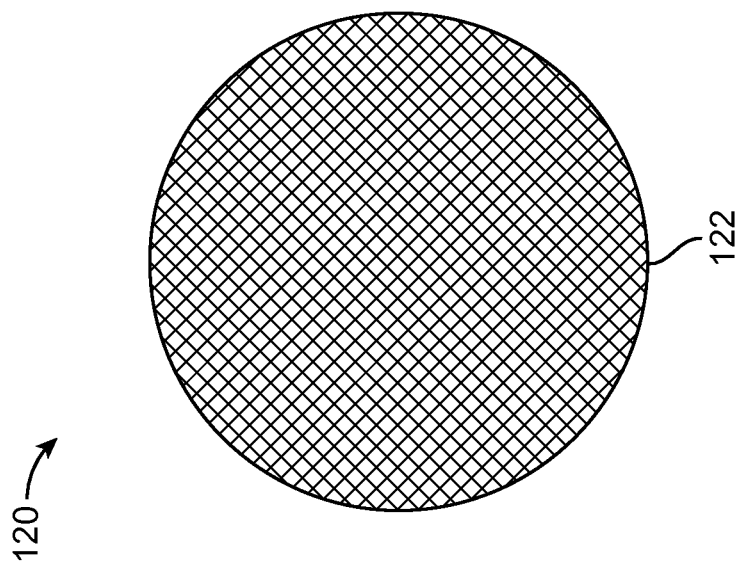
FIG. 3 depicts a schematic cross-sectional view of the flow head embodiment of FIG. 2.
Figure 16:
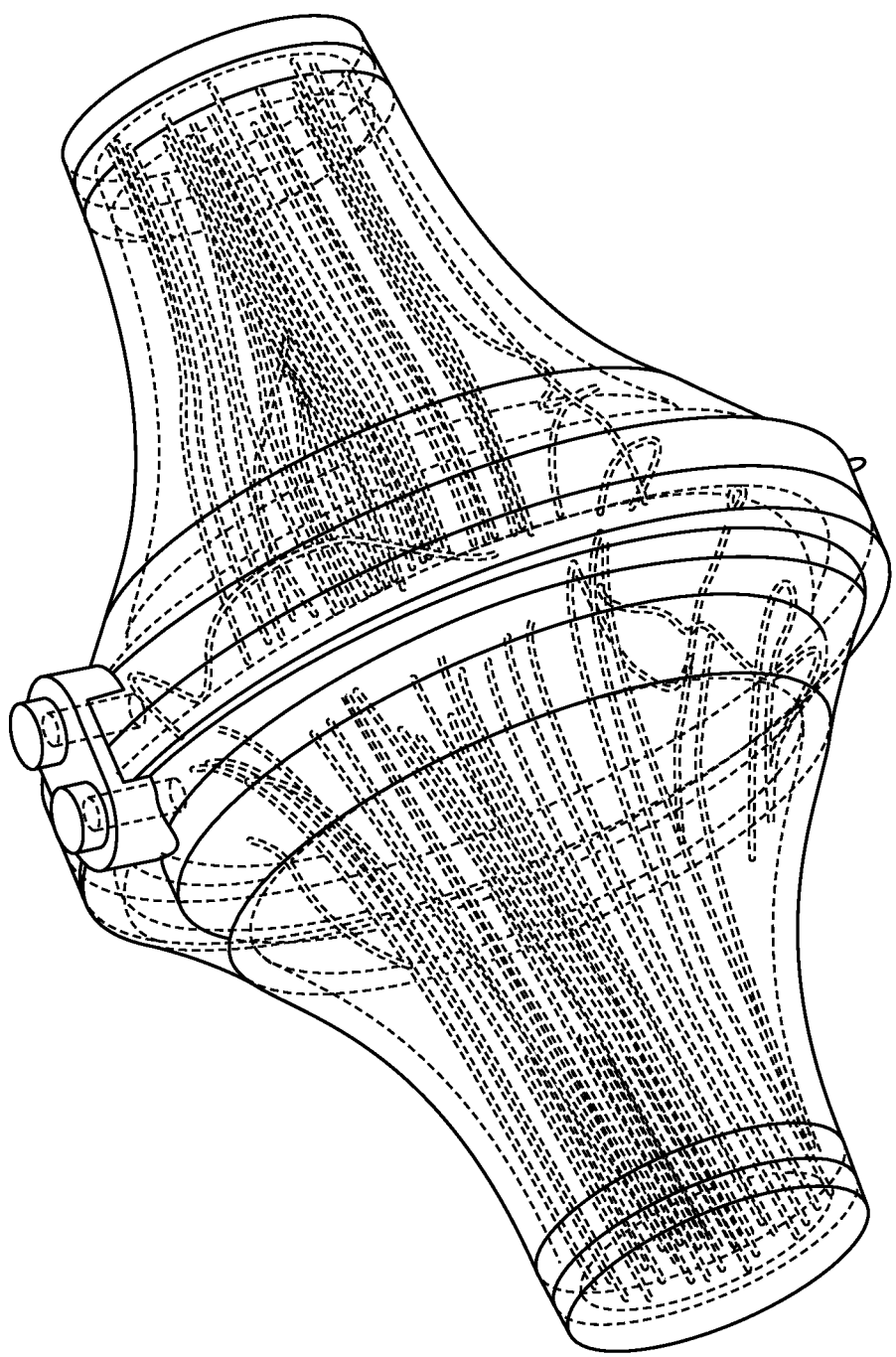
FIG. 16 depicts a perspective view of another embodiment of a handheld measurement device for monitoring lung function, wherein the walls of the device are depicted transparently and airflow through the measurement device is modeled with a plurality of airflow path lines.

The flow head 120 of FIG. 2 houses components configured to provide spirometry metrics. In particular, in the depicted embodiment, the flow head 120 houses a mesh, such as a stainless steel mesh. As shown in the cross-section of FIG. 3, the mesh 122 is disposed across an entire cross-section of the flow head 120 such that a distal end of the flow head 120 is separated from the proximal end of the flow head 120 by the mesh 122. With the mesh 122 secured, when a patient blows into the device 100, there is an influx of air through the lumen 160 into the flow head 120 of the measurement device 100. This air entering the flow head 120 experiences a change in velocity and pressure when it crosses the mesh 122 due to resistance created by the mesh 122. If the flow within the flow head 120 is laminar and there are no other significant variables changing within the flow head 120 (such as changes in temperature or diameter), the change in pressure is directly proportional to the flow rate of the expired air. In various embodiments provided herein, the measurement devices are configured such that the diameters of the lumen 160 on each side of the mesh 122 are equal and air flow within the flow head 120 is laminar or substantially laminar. One example of substantially laminar flow through a measurement device embodiment constructed in accordance with the principles of the present disclosure is provided in FIG. 16.

Figure 5:
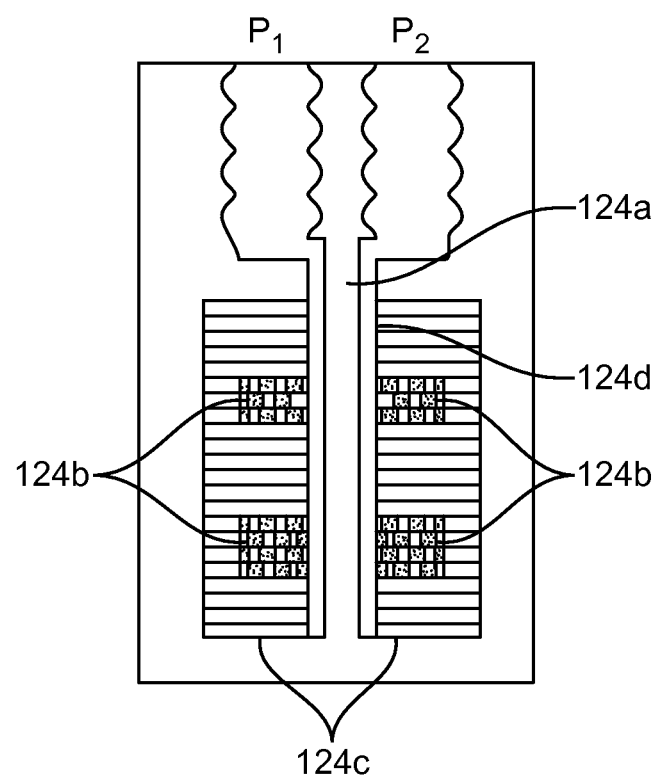
FIG. 5 depicts a schematic cross-sectional view of one embodiment of a pressure sensor.

In some embodiments, holes 126 located on the body 101 on opposing sides of the mesh 122 serve to relay baseline pressure sensor inputs to a signal transducer (i.e., a sensor). The pressure sensor 124 may be, for example, a strain-based variable reluctance sensor configured to form a magnetic circuit. One embodiment of a strain-based variable reluctance sensor 124 is shown in FIG. 5. As shown, the strain-based variable reluctance sensor 124 includes a spring member 124a, a plurality of coils 124b, a plurality of coil forms 124c, and media interface barriers 124d made, for example, of stainless steel.

Figure 4:
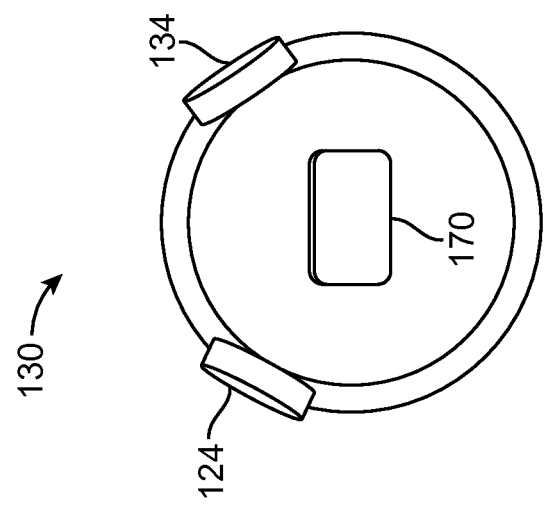
FIG. 4 depicts a schematic cross-sectional view of the sensor housing embodiment of FIG. 2.

The reluctance sensor 124 may be positioned within the flow head 120 on either side of the mesh 122. The sensor 124 may be positioned, for example, on or adjacent to the mesh 122. In other embodiments, such as shown in FIG. 4, the reluctance sensor 124 is positioned in the sensor housing 130. Regardless of the location of the sensor 124, when a patient blows into the device 100, the differential pressure causes a deflection of the spring member 124a in the sensor 124 towards the magnetic pole piece on the low-pressure side of the spring member 124a. This distortion of the spring 124a prompts a change in a modulation of inductance of the two coils 124b, which is then read by an electric circuit. The variation in the magnetic reluctance produces the effective inductance modulation as a function of the parameter input such that a certain spring deflection can be calibrated to a certain pressure measurement.

The resulting pressure measurements can then be converted to corresponding flow rates (for example, meters³/second) by calculating flow (i.e., velocity) (for example, meters/second) using Bernoulli's equation and multiplying the corresponding flow by the cross-sectional area (meters²) through which the flow occurs.

For example:

Bernoulli's Equation: $\frac{1}{2}*\rho *v^2+\rho *g*z+P=\text{constant}$ where $\rho$=air density (kg/m³)
v=velocity (m/s)
g=acceleration due to gravity (m/s²)
z=height (m)
P=pressure (Pa)

Flow equation: $Q=v*A$ where Q=flow rate (L/s)
v=velocity (m/s)
A=cross-sectional area (m²)

For the integrated device, Bernoulli's equation can be simplified as there is no change in height for the airflow (z=0). Solving for v in this simplified equation yields:

$v=(2*P/\rho)^{0.5}$

Flow rate is then calculated by:

$Q=v*A$ $=(2*P/\rho)^{0.5}*(\pi*(d/2)^2$

As will be described in more detail below, such calculations may be performed by a processor located on or in the device 100 or a processor in communication with the device 100.

The optional sensor housing 130 of FIG. 2 is a tubular component which houses, at least, components configured to sense and/or measure cardiopulmonary biomarker levels, if present within the measurement device 100. A schematic cross-section of the tubular sensor housing 130 is shown in FIG. 4. As shown, the sensor housing 130 houses one or more nitric oxide sensors 134 and the reluctance sensor 124 described above. Also visible in the cross-section of FIG. 4 is a tip of an inhaler 170, which may be coupled to the cover 150 at the distal end of the holding chamber 140. Because the various sections of the device 100 are connected and share a lumen 160, the inhaler 170 may be visible from a position inside the sensor housing 130. In one embodiment, both the pressure sensor 124 and nitric oxide sensor 134 are housed in the sensor housing 130 and are concealed from the outside with a cover that fits to the outer diameter of the casing (not depicted). The sensors and/or any accompanying circuitry may be isolated in an electronics compartment to protect the components from damage, for example from cleaning and liquids.

Figure 6A:
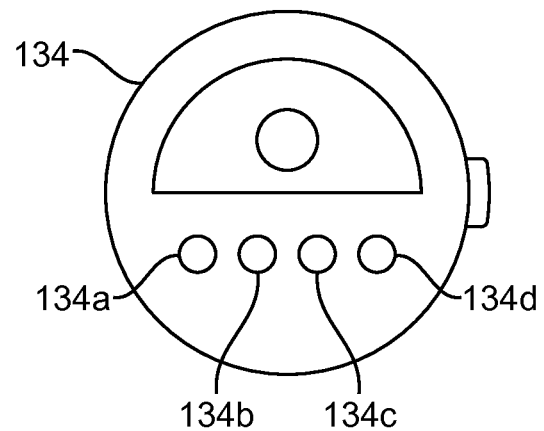
FIG. 6A depicts a schematic top view of one embodiment of a nitric oxide sensor.
Figure 6B:
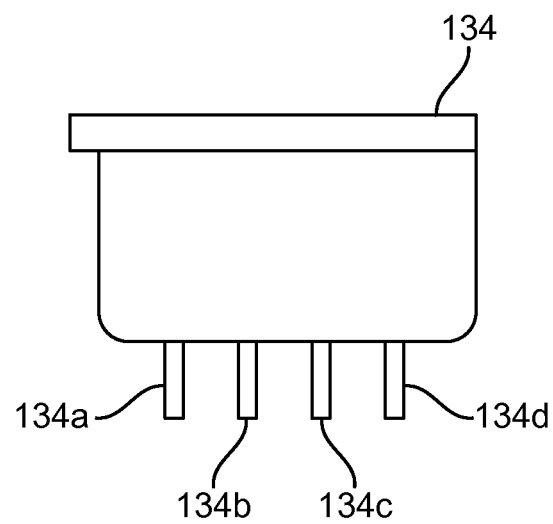
FIG. 6B depicts a schematic side view of the nitric oxide sensor embodiment of FIG. 6A.

In one example, the nitric oxide sensor 134 present in the sensor housing 130 is a Clark electrode device, such as the electrode of FIGS. 6A and 6B. The Clark electrode device has three relevant electrodes: a counter 134a, a working 134b, and a reference 134d. In some embodiments, the other electrode 134c is not used and may not be provided. In one embodiment, based on the diffusion rate of nitric oxide in the device 100, the electrodes 134 are calibrated to quantify nitric oxide levels using a redox reaction on a catalytic platinum surface. In other embodiments, a different nitric oxide sensor, such as a graphene oxide electrically contacted sensor is used. Such a sensor is described in Li, et al., "Reduced Graphene Oxide Electrically Contacted Graphene Sensor for Highly Sensitive Nitric Oxide Detection," 2011 *ACS Nano*, which is herein incorporated by reference in its entirety. In still other embodiments, a different cardiopulmonary biomarker sensor is used.

As depicted in FIG. 2, in some embodiments, a protective compartment 136, housing a sensor circuit, a processor, and optionally, a GPS system, is present on or in the device 100. While the protective compartment 136 is visible in the schematic of FIG. 2, in preferred embodiments, the protective compartment 136 is disposed within the body 101 where it is not readily visible.

Figure 17:
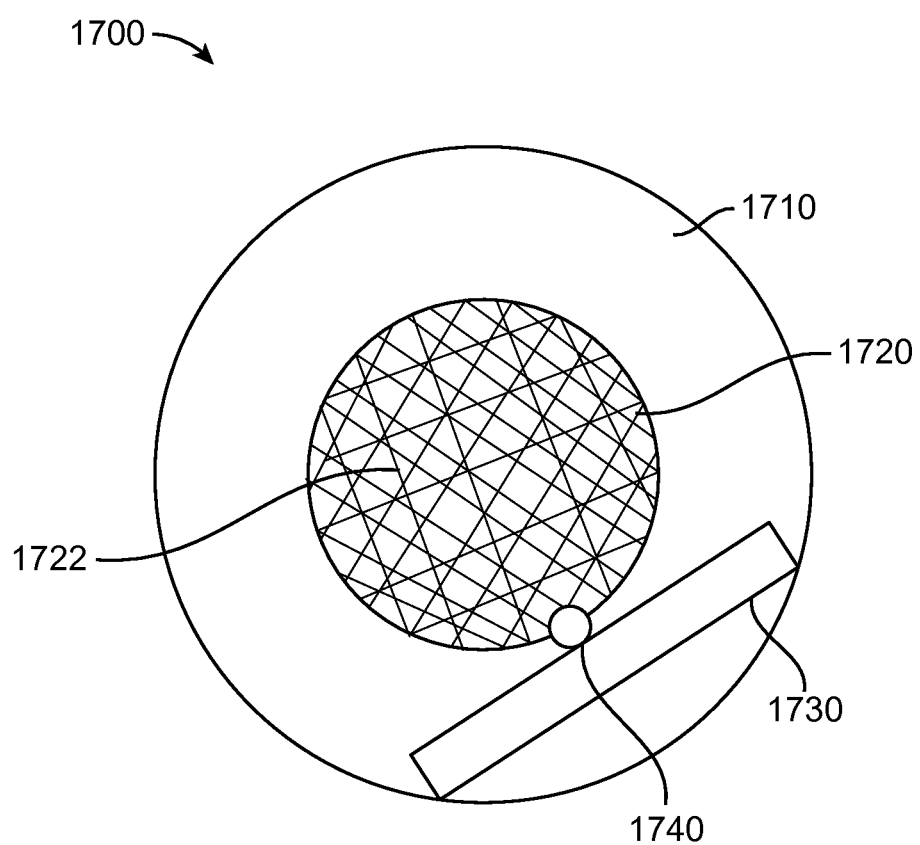
FIG. 17 depicts a cross-sectional view of another embodiment of a handheld measurement device for monitoring lung function.

One non-limiting example of a measurement device having the protective compartment and sensor circuit disposed within the sensor housing is shown in the cross-sectional view of a flow head provided in FIG. 17. As shown, the flow head of the measurement device 1700 includes: an inner lumen 1720 defined by an inner tubular wall, and an outer annular lumen 1710 defined by the inner tubular wall and an outer tubular wall. In such embodiments, the inner lumen 1720 is fluidly connected (directly or indirectly) to the mouthpiece aperture and is configured to transport airflow. A mesh 1722 may be disposed within the inner lumen 1720 to create air flow resistance. In such embodiments, the outer annular lumen 1710 is protected and fluidly separated from both the outer environment and the inner lumen 1720. The outer annular lumen 1710 acts as the protective compartment, and in some such embodiments, all or substantially all the circuitry and electrical components of the measurement device 1700 are housed within the outer annular lumen 1710. As shown, a printed circuit board 1730, which includes a sensor circuit, a processor, and optionally, a GPS sensor, is located within the protected space of the outer annular lumen 1710. In some embodiments, one or more sensors 1740 are disposed on the periphery of the inner lumen 1720 such that the one or more sensors 1740 are able to sense a pressure differential across opposing sides of the mesh 1722 in the inner lumen 1720. In such embodiments, the sensors 1740 are electrically coupled to the circuit of the circuit board 1730. The one or more sensors 1740 may be positioned such that one end of the sensor 1740 is exposed within the inner lumen 1720 and another end of the sensor 1740 is disposed within the outer lumen 1720; in such embodiments, an airtight seal may surround a circumference of the sensor 1740, holding the sensor 1740 in place and preventing moisture or other contaminants of the inner lumen 1720 from entering the protected space of the outer lumen 1710.

The circuit of various measurement devices (for example, the circuit on the circuit board 1730 of FIG. 17 and the circuit in the protective housing 136 of FIG. 2) is in wired connection with the pressure sensor and, if present, the cardiopulmonary biomarker sensor (e.g., a nitric oxide sensor), and receives signals from each. In some embodiments, the sensor signals are analog signals, generally in the form of voltage. In some such embodiments, the circuit includes an analog-to-digital converter to digitize the signals. The circuit of various embodiments further includes a power source, such as a battery and/or a connector for receiving power from an external AC or DC power supply. In some embodiments, the circuit includes one or more signal processing components, which may act to amplify the signal, reduce the signal-to-noise ratio, and the like. Some embodiments also include a radiofrequency (RF) transmitter or other wireless transmitter in the circuit for transmitting digital signals wirelessly to a remote computing device.

In some embodiments, the circuit is an integrated circuit constructed using complementary metal-oxide-semiconductor (CMOS) technology. This design directly converts the analog input signal to serial data using a current-based modulator on the transmission side. Examples of suitable circuits are provided in Roham, et al., "Diamond microelectrodes and CMOS microelectronics for wireless transmission of fast-scan cyclic voltammetry," 2007 *IEEE Eng. Med. Biol. Soc.*, which is herein incorporated by reference in its entirety.

Additionally or alternatively, as part of the sensor circuit (e.g., the sensor circuit within the protective housing 136), the device 100 may include an onboard processor and memory configured with instructions to convert raw digital signals into processed signals and/or useful data. In some such embodiments, the instructions include instructions to convert the signal from the pressure sensor 124 into a flow rate, and optionally, instructions to compare the flow rate to a stored threshold flow rate. In some embodiments, the onboard processor and memory are configured with instructions to calculate Forced Expiratory Flow during the range when 25-75% remains of the forced vital capacity (FEF 25-75%) from the digital pressure signals. FEF 25-75% data is particularly relevant to children and captures information from the smaller airway tracts. In other embodiments, the instructions include instructions to save the raw digital signals in a text file or other file formatted for transmission to a remote computing device. In such embodiments, various spirometry calculations are performed by the remote computing device based on the signals received. In some embodiments, the onboard processor and memory are configured to store the signals and/or the useful data on the device, at least until a point in time in which they can be transmitted or relayed to a remote computing device.

Figure 18:
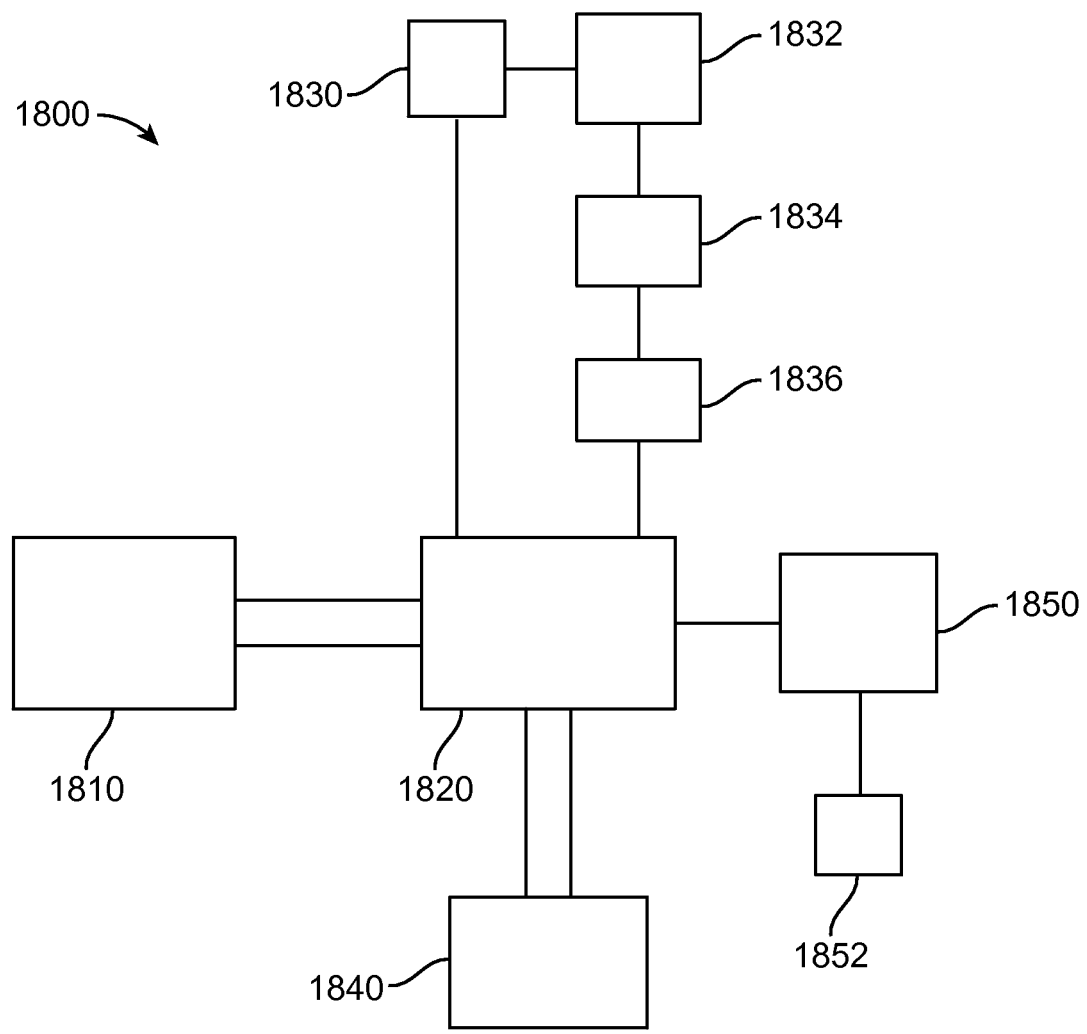
FIG. 18 depicts a functional block diagram of one embodiment of a circuit provided within various embodiments of a handheld measurement device.

A non-limiting example of a measurement device circuit (for example, the circuit on the printed circuit board 1740 of FIG. 17 or the circuit in the protective housing 136 of FIG. 2) is provided in FIG. 18. The circuit 1800 includes: a power supply such as a battery 1832, a processor 1810, an input/output device 1840 such as a radiofrequency (RF) antenna, a sensor 1852, and an amplification circuit 1850. Any suitable battery, processor, RF antenna, and circuitry components may be used. In some embodiments, the processor is a Cortex-M ARM® processor. In some embodiments, the RF antenna is a Bluetooth® antenna. In some embodiments, the battery is a lithium ion battery. In some embodiments, one or more of the components, such as the processor 1810, the RF antenna 1840, and the amplification circuit 1850, each have relatively heavy current draws and should be connected directly to the battery 1832. Accordingly, in such embodiments, an optional power junction 1820 may be provided to couple each of said components to the battery 1832. In other embodiments, no power junction 1820 is needed.

In some embodiments, the sensor 1852 includes one or more pressure sensors, biomarker sensors, or any other sensors described elsewhere herein. In some embodiments, the amplification circuit 1850 is configured to amplify the sensor signals and may also be configured to filter and/or digitize the sensor signals. The circuit 1850 may include, for example, an amplifier such as an operational amplifier or other differential amplifier. The circuit 1850 may also include one or more filters, such as a band pass, low pass, and/or high pass filter. In some embodiments, the circuit 1850 additionally includes an analog-to-digital converter (ADC).

The battery 1832 of some embodiments is rechargeable and connected, at times, to a battery charging component 1830. The battery charging component 1830 of some embodiments is an AC or DC source coupled to the battery 1832, for example, via a wall outlet, electrical plug, and cable. When coupled to the battery charging component 1830, the circuit 1800 of some embodiments draws power for the various circuit components directly from the battery charging component 1830. In such embodiments, a switch (e.g., an on/off switch) 1834 is connected to the battery 1832 to control voltage flow. If no battery charging component 1830 is connected, the switch 1834 will be in an on state, and the battery will serve as the voltage source. If a battery charging component 1830 is connected, the switch 1834 will be in an off state, and the battery charging component 1830 will serve as the voltage source. In some embodiments, the battery 1832 supplies a voltage below 5V (for example, in the range of 3.0-4.5V), while the processor 1810 and RF antenna 1840 require a voltage of 5V to function properly. In such embodiments, a voltage boost converter is provided within the circuit 1800 and electrically connected between the battery 1832 and the power junction 1820. The boost converter boosts the voltage coming from the battery to 5V. In other embodiments, all components are configured to operate with a 3.3V power supply. For example, in embodiments using a Cortex-M ARM® processor, all components can function at 3.3V. In such embodiments, no boost converter is needed. Rather, in some such embodiments, an optional regulator 1836 is provided to ensure a voltage of 3.3V is consistently delivered to the various circuitry components. Any embodiment of the circuit described here may be present in any one or more of the measurement device embodiments described elsewhere herein.

Figure 7:
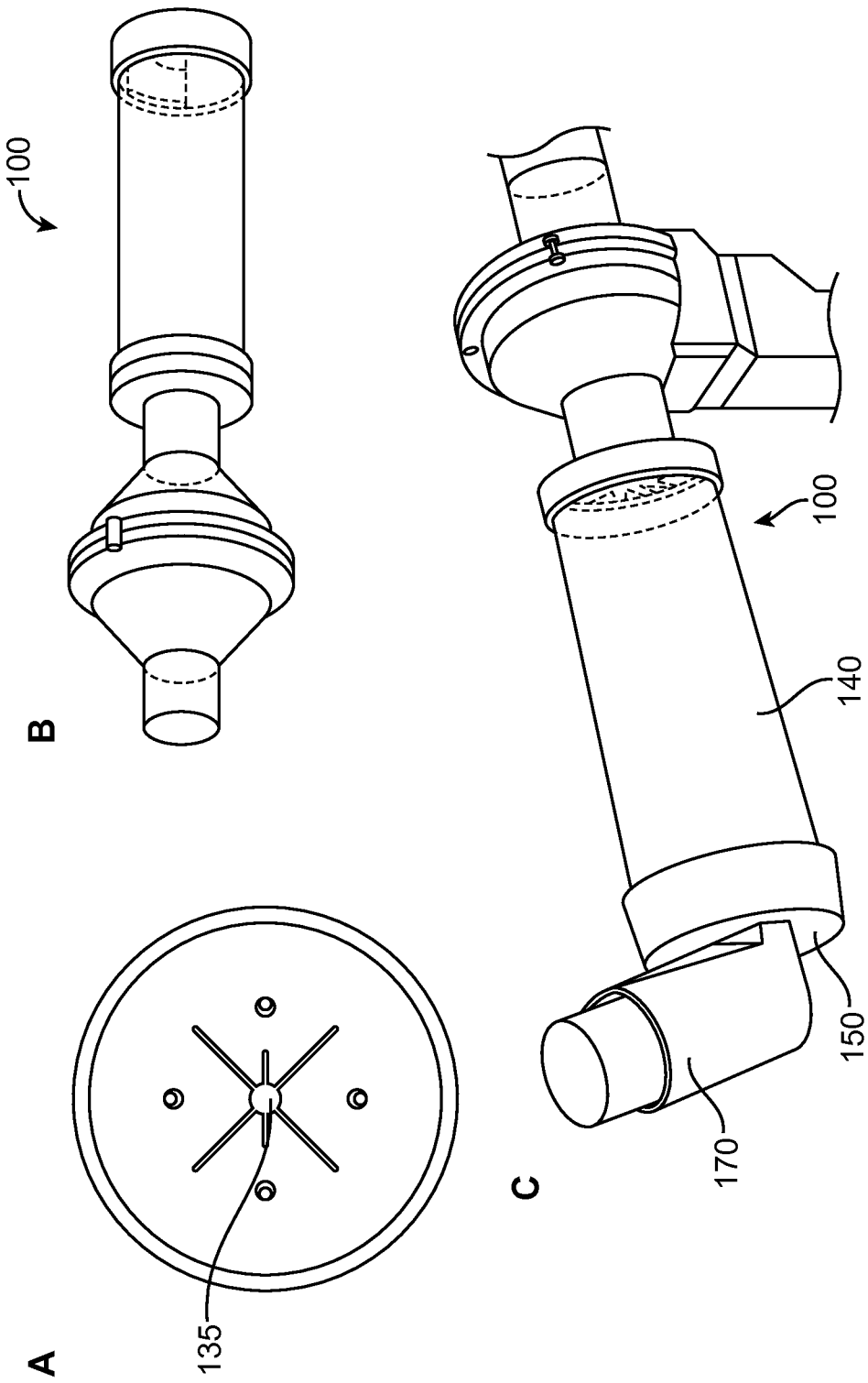
FIGS. 7A-7C are photographs of various views of another embodiment of a handheld measurement device for monitoring lung function.

Returning to FIG. 2, the measurement device 100 of some embodiments includes a chamber 140. The chamber 140, if present, is configured to hold aerosolized medicine after it has been expelled from an inhaler into the chamber 140. In some embodiments, the chamber 140 is separably connected to the first portion of the device 100, which includes the mouthpiece 110, flow head 120, and optional sensor housing 130. In some such embodiments, the two portions securely connect and lock into place via complementary threading, a friction fit, or a snap fit. In some such embodiments, the chamber 140 is substantially similar to, or is formed of, a spacer. Spacers, such as the spacer forming the chamber 140 in FIGS. 7A-7C, themselves have four sections: a main chamber that holds the medicine, a removable one-way valve 135 (see FIG. 7A) that holds the medicine until voluntarily inhaled, a mouthpiece where the patient can inhale the medicine, and a cover 150 on the opposite side of the mouthpiece, which includes a hole that conforms to the outside shape of the inhaler mouthpiece, allowing the inhaler 170 to attach to the chamber 140. In one embodiment, the first portion of the device 100, which includes the flow head 120, twists into locked engagement with the existing mouthpiece of the spacer. In such a configuration, the sensor housing 130 may be fully or partially disposed within, or attached to the proximal end of, the spacer mouthpiece. In some embodiments, the chamber is 17 cm long and 5.1 cm in diameter. In other embodiments, the chamber is 12 cm long, 20 cm long, or any value therebetween, and the diameter is 4 cm, 5.5 cm, or any value therebetween.

In some non-limiting examples, the device 100 as described conforms to one or more of the target benchmarks listed in Table 1. In some embodiments, one or more components of the device 100 conform to the range of marginal values, and in some embodiments, one or more components of the device 100 conform to the range of ideal values. In some embodiments, one or more of the components conform to a particular subrange or individual value therebetween.

TABLE 1

Target specifications for device based on relevant benchmarks.

|  | Units | Marginal Value | Ideal Value |
|---|---|---|---|
| Chamber Length | cm | 12-20 | 13-17 |
| Chamber Diameter | cm | 4-5.5 | 4-5.3 |
| Weight | g | 80-110 | <100 |
| Pressure Sensitivity | psi | 1 | $10^{-1}$ |
| Volume Sensitivity | L | $10^{-3}$ | $10^{-3}$ |
| Flow Rate Sensitivity | L/s | $10^{-2}$ | $10^{-2}$ |
| Sampling Rate | samples/s | 50-100 | 100-150 |
| Frequency of Monitoring | #/day | 5-15 | >10 |
| Flow Rate Threshold | L/s | (+/−) 10-25 | (+/−) 18-25 |
| Chemical Sensitivity | ppb | 1-10 | 1-5 |

Figure 10:
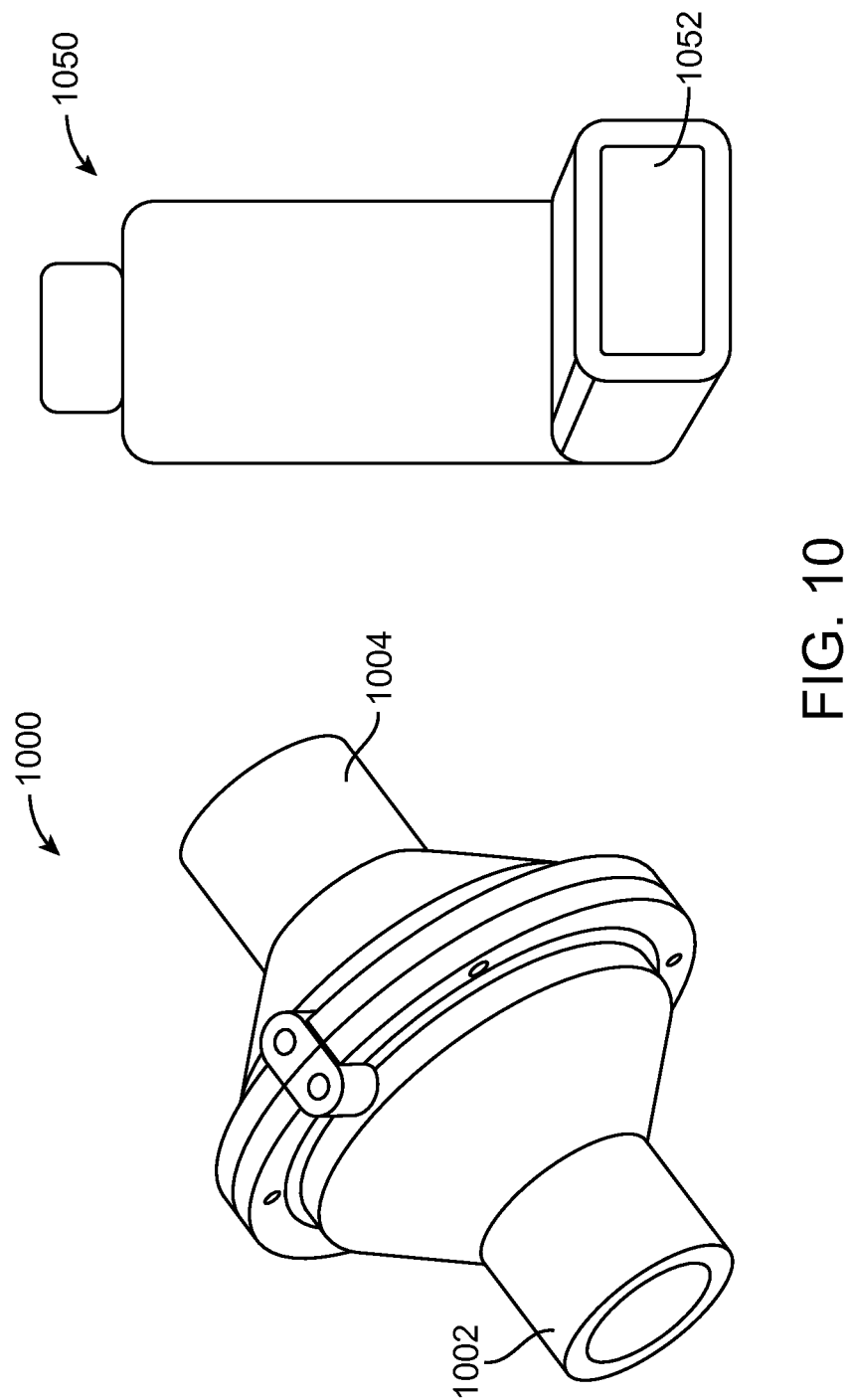
FIG. 10 depicts a schematic perspective view of another embodiment of a portable measurement device for monitoring lung function. In some embodiments, the measurement device is configured for attachment to an inhaler, such as the inhaler also shown in FIG. 10.

In some embodiments, the measurement device consists of or substantially consists of the mouthpiece and flow head with sensors and circuitry disposed therein. Such a device 1000 is shown in FIG. 10. In various embodiments, the device 1000 is a separate portable device that can be used on its own to obtain lung function metrics such as spirometry and cardiopulmonary biomarker readings; it may also be capable of coupling to a medication delivery apparatus in order to record, for example, a count of inhaler use and/or the amount of medication dispensed over time. In some embodiments, the distal end of the measurement device 1000 couples securely but removably to a spacer, such as via a connection with the mouthpiece of the spacer. In other embodiments, such as the embodiments shown in FIG. 10, the distal end 1004 of the measurement device 1000 is sized and shaped to couple securely but removably to a proximal end 1052 of an inhaler 1050. In some embodiments, the distal end 1004 of the measurement device 1000 securely connects to the medication dispensing apparatus via an appropriate connection, such as, for example, complementary threading, a friction fit, or a snap fit. In some embodiments, the measurement device 1000 includes an attachment feature sized and shaped to connect securely and interchangeably to at least one model of an inhaler and at least one model of a spacer. In some embodiments, the attachment feature is molded to the distal end of the device 1000 or otherwise permanently affixed to the measurement device 1000. In other embodiments, the measurement device 1000 includes a plurality of interchangeable attachment features, which connect to the measurement device 1000 via a removable but secure connection, such as, for example, complementary threading, a friction fit, or a snap fit. In such embodiments, the interchangeable attachment features enable the measurement device 1000 to couple to both spacers and inhalers. In some embodiments, the interchangeable attachment features enable the measurement device 1000 to couple to a plurality of brands and models of medication delivery apparatuses.

Another embodiment of a measurement device in the form of an improved spacer is provided in FIGS. 12A-12F. In the depicted embodiment, the measurement device 1200 has a proximal end 1202 and a distal end 1204. The measurement device 1200 has a substantially hollow body 1201 defined by a plurality of sections or features, including a spirometry component 1210, an aerosol holding chamber 1220, and a biomarker detection component 1230. These sections are all directly or indirectly coupled together, permanently or separably, and all share a common lumen 1260. In various embodiments, the body 1201 is formed of one or more materials, such as one or more polymers, having one or more of the physical properties described in the descriptions of other embodiments provided herein.

The spirometry component 1210 of various embodiments includes a mouthpiece 1212 and a flow head 1214. The flow head 1214 of various embodiments includes a mesh stretched across the entirety of the lumen 1260 at a position within the flow head 1214. Such a mesh at least partially restricts airflow so as to create a pressure differential on opposing sides of the mesh when air is exhaled into or inhaled from the lumen 1260 of the device 1200. In some embodiments, the spirometry component 1210 also includes a spirometry adaptor 1216 configured to create an airtight connection between the spirometry component 1210 and the aerosol holding chamber 1220. In other embodiments, the spirometry component 1210 is molded directly to the aerosol holding chamber 1220. The aerosol holding chamber 1220 acts as a spacer, helping to deliver aerosolized medication to the lungs of patients who use the device.

The biomarker detection component 1230 includes a biomarker sensor, such as, for example, a nitric oxide sensor and/or a pentane, ethane, 8-isoprostane, cysteinylleukotrienes, prostaglandin E2, hydrogen peroxide, aldehydes, nitrotyrosine, cytokines, and/or Leukotriene B4 sensing apparatus for detecting exhaled levels of one or more cardiopulmonary biomarkers. In various embodiments, a pressure sensor is disposed within the spirometry component 1210 or the biomarker detection component 1230. The biomarker detection component 1230 of some embodiments is formed within a distal cap 1240. The distal cap 1240 of such embodiments includes an inhaler receiving feature designed to securely couple to the mouthpiece of an inhaler. In some embodiments, the distal cap 1240 is permanently molded or otherwise permanently secured to a distal portion of the aerosol holding chamber 1220. In other embodiments, the distal cap 1240 is securely but removably coupled to the aerosol holding chamber 1220.

In various embodiments, the distal cap 1240 additionally or alternatively includes a power supply, a processor, and a non-transitory computer readable medium stored therein. The distal cap 1240 may also include an audible output component such as a speaker and/or a visual output component such as a display screen (e.g., an LCD screen) or one or more lights. For example, in the embodiment of FIG. 12A, the device 1200 includes an array 1232 of red, yellow, and green LED lights. In certain embodiments, the processor receives power from the power supply and is configured to execute software code stored within the non-transitory computer readable medium. Execution of the software code causes the processor to perform functions, such as, for example, one or more of the functions described below. In one non-limiting embodiment, when flow rate falls below a certain threshold or nitric oxide levels rise above a certain threshold, the processor may send signals to an output component such as a warning light, warning sound generator, or other warning indicator, causing the warning indicator to emit a warning.

In certain embodiments, the processor of the measurement device 1200 receives input signals from the pressure sensor and the biomarker sensor. The processor analyzes the signals received from the pressure sensor to determine whether a pressure differential exists within the lumen 1260 of the measurement device 1200. If a pressure differential is present, the processor evaluates, based on the differential, whether an individual inhaled from, or exhaled into, the device 1200. If an inhalation is detected, the processor may increment a counter, which tracks the number of times an inhaler is used. In some embodiments, the processor also records to memory the date and time of the inhaler use, and optionally, the dosage of the medicine dispensed. If an expiration is detected, the processor may calculate one or more of the following metrics based on data acquired by the spirometry component: Peak Expiratory Flow rate (PEF), a Forced Expiratory Flow (FEF) rate such as FEF25-75%, Forced Expiratory Volume within a given time interval such as the first second (FEV1), Forced Vital Capacity (FVC), tidal volume, residual volume, breathing rate, and/or ventilation rate. In some embodiments, one or more of these metrics are stored in memory, optionally, with the date and/or time of the recording. In some embodiments, the level of one or more cardiopulmonary biomarkers present in the expiration is also recorded, optionally, with the date and/or time of the recording. In some embodiments, when flow rate or other spirometry-related metric falls below a certain threshold or a biomarker level rise above a certain threshold, a warning indicator may be emitted from an output device. For example, as shown in FIGS. 12A-12F, in some embodiments, the device includes a green light, which illuminates when flow rate is above a first flow rate threshold and/or nitric oxide levels are below a first biomarker threshold. The device also includes a red alert light, which illuminates when the flow rate falls below a second, lower flow rate threshold or nitric oxide levels rise above a second, higher biomarker threshold. The device may further include a yellow warning light, which illuminates when the flow rate falls between the first and second flow rate thresholds or nitric oxide levels rise between the first and second biomarker thresholds.

In some embodiments, the sensor signals generated within the measurement device 1200 are converted from analog to digital signals and transmitted wirelessly or via a wired connection to a smartphone, tablet, laptop, or other remote personal computing device for analysis, display on a remote display screen, and/or storage. In other embodiments, the sensor signals are processed by the on-board processor and the processed data is transmitted wirelessly or via a wired connection to a remote personal computing device for further analysis, display on a remote display screen, and/or storage. In embodiments in which data is transmitted wireless to a remote personal computing device, the device 1200 also includes a wireless transmitter, such as, for example, a Bluetooth®, Wi-Fi®, or any other suitable wireless transmitter. In still other embodiments, digitized sensor signals and/or processed data are transmitted wirelessly from the measurement device 1200 to a server, for example, for analysis, transmission to other computing devices, and/or storage. In such embodiments, the device 1200 also includes a wireless transmitter, such as, for example, a Wi-Fi®, cellular, or any other suitable wireless transmitter.

Figure 14A:
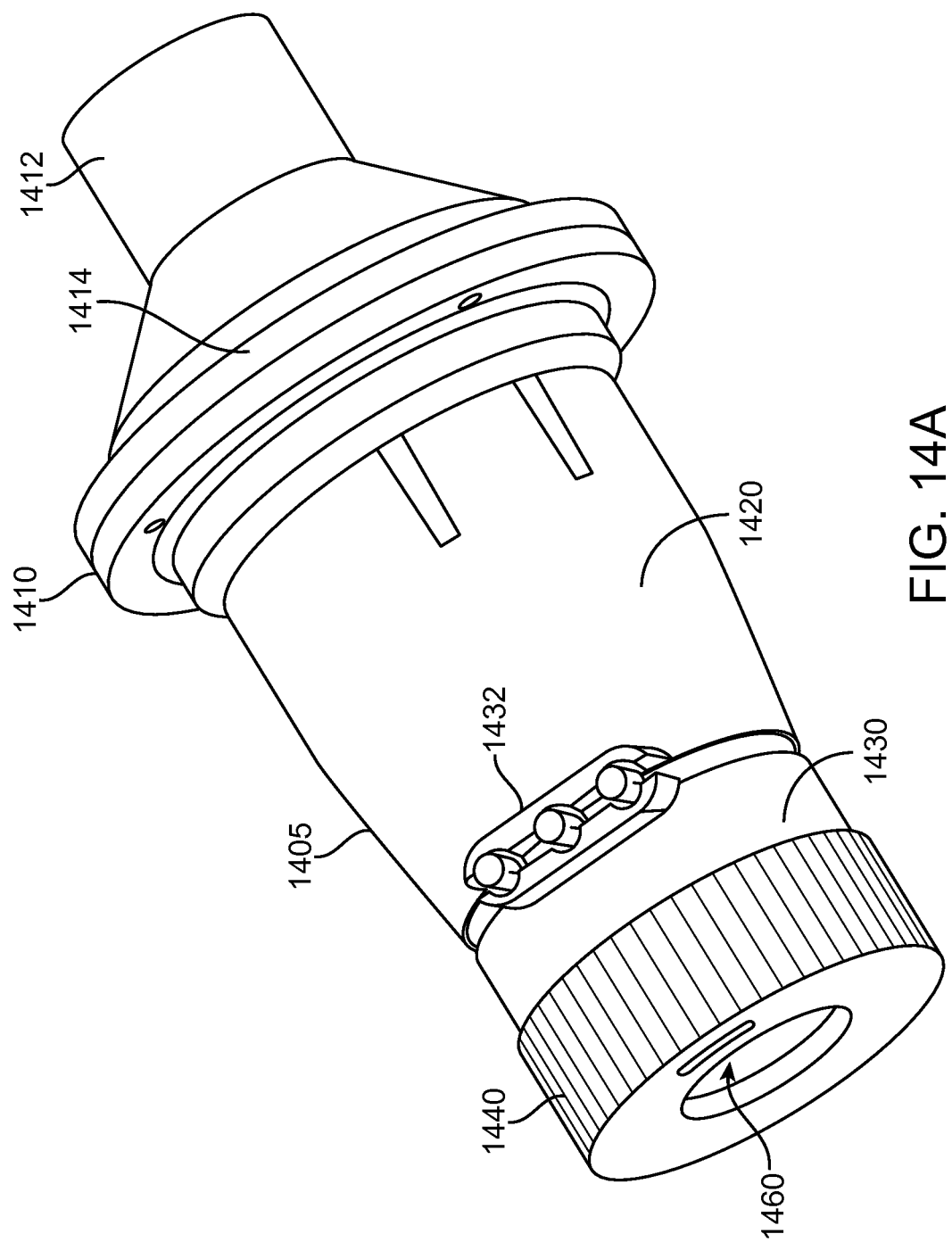
FIG. 14A depicts a schematic distal perspective view of another embodiment of a portable measurement device for monitoring lung function.
Figure 14B:
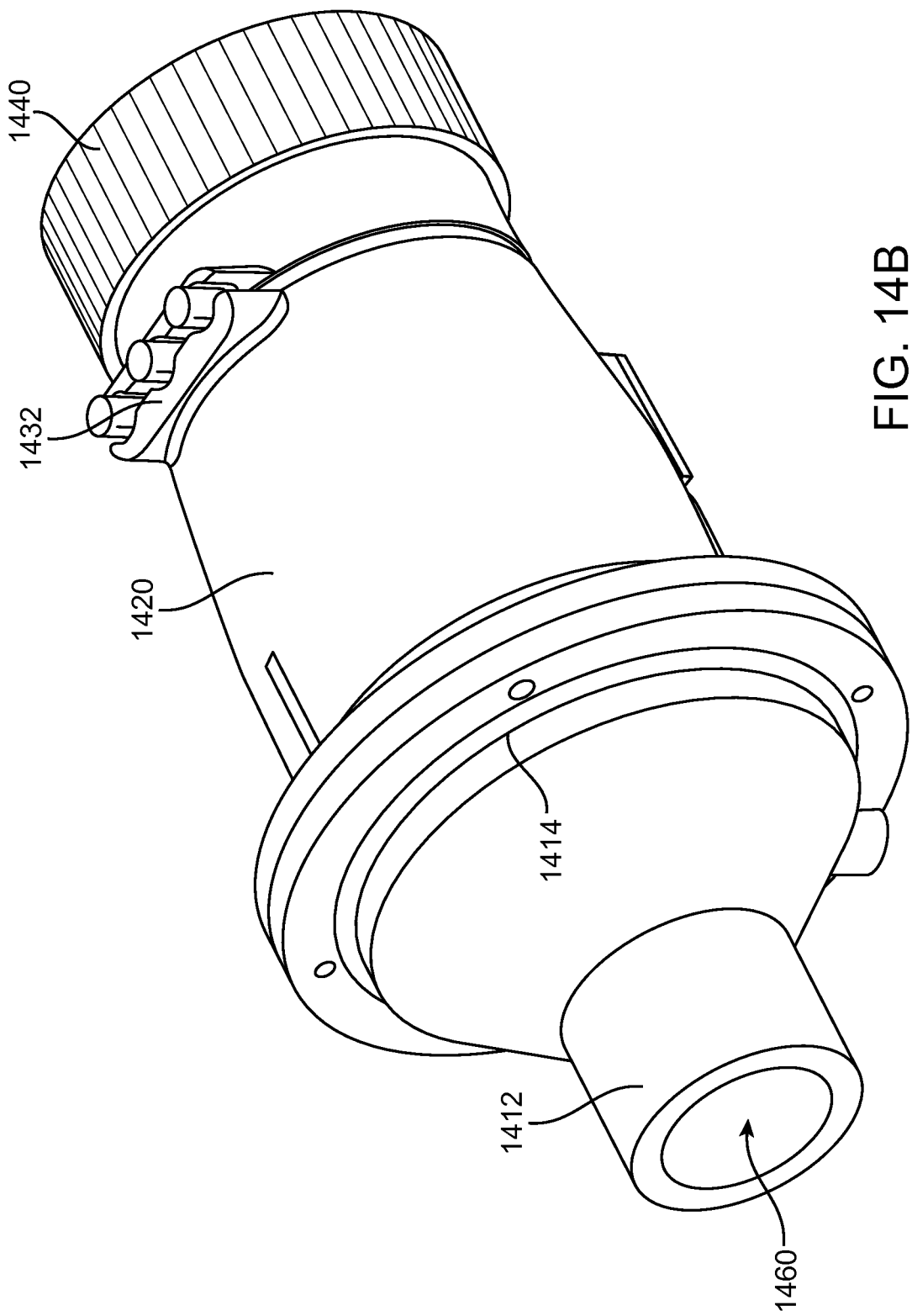
FIG. 14B depicts a schematic proximal perspective view of the measurement device of FIG. 14A.
Figure 14C:
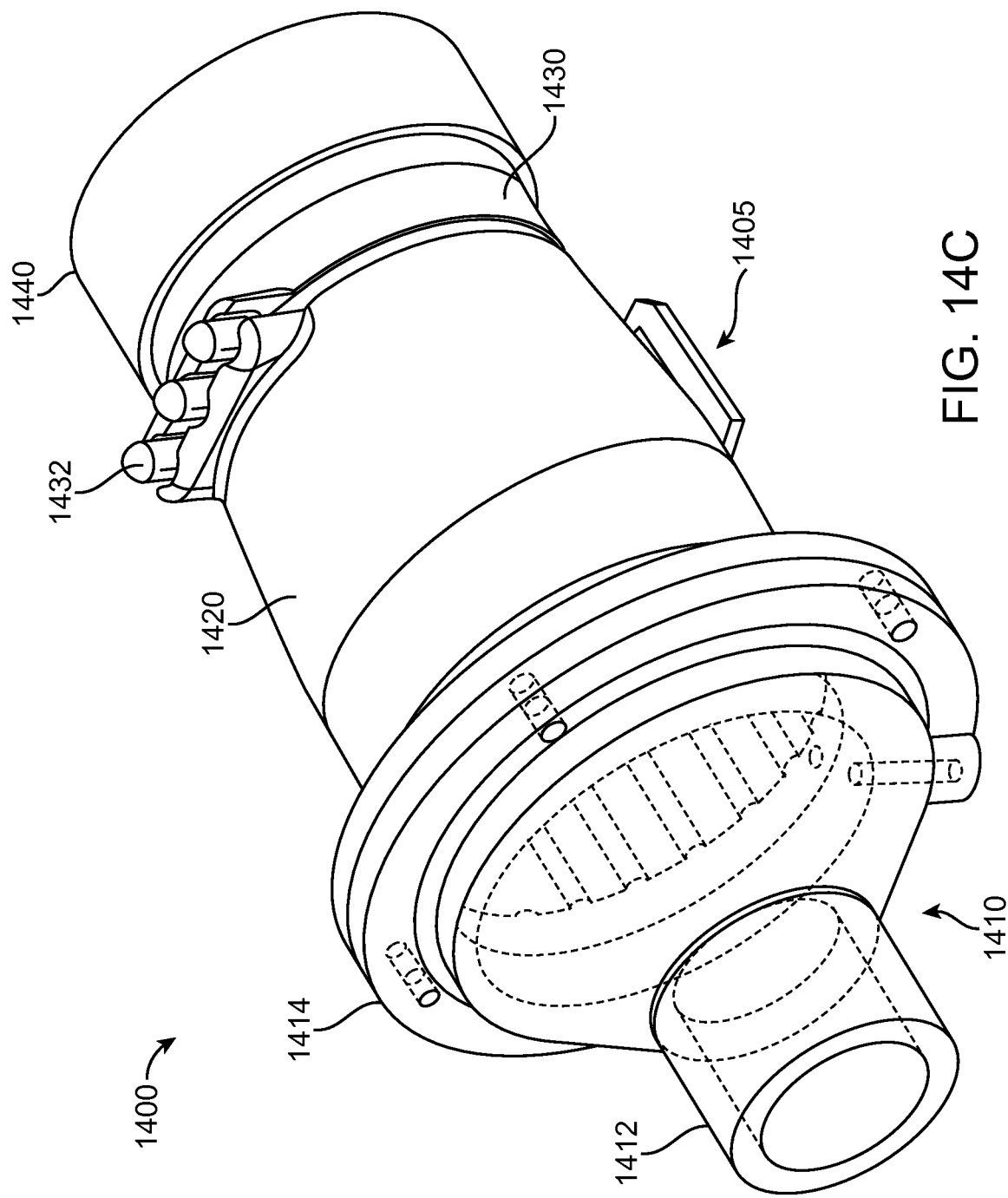
FIG. 14C depicts another schematic proximal perspective view of the measurement device of FIG. 14A.

Another embodiment of a measurement device is provided in FIGS. 14A-14C. The measurement device 1400 of the illustrated embodiment includes all the functionality of the measurement device 1200 of FIGS. 12A-12F provided in a more compact and portable structure. As shown in FIG. 14A, the measurement device 1400 of some embodiments has a body portion 1405 and a head portion 1410 with a lumen 1460 extending substantially or completely therethrough. The body portion 1405 includes a distal cap or end portion 1440 having a distal slot extending therethrough that is sized and shaped to couple to an inhaler. In other embodiments, the distal cap 1440 is closed or substantially closed and includes a connecting feature for coupling to a portable computing device. For example, the connecting feature may be a plug configured for connection with a headphone jack or charging port of a portable computing device. The body portion 1405 also includes an aerosol holding chamber 1420, and an output display 1432. The output display 1432 of FIGS. 14A-14C is an array of lights; in other embodiments, the output display 1432 is a display screen.

In some embodiments, no biomarker detection component is visible from the outer surface of the measurement device 1400; rather, the biomarker detection sensors, if present at all, are positioned within the aerosol holding chamber 1420. In other embodiments, to increase the compactness of the design, there is little to no aerosol holding chamber 1420. In such embodiments, all sensors and circuitry are disposed within the head portion 1410. The head portion 1410 of FIGS. 14A-14C includes a spirometry component 1414 and a mouthpiece 1412. In the depicted embodiment, the head portion 1410 is permanently affixed to the body portion 1405; in various embodiments, the connection between the head portion 1410 and body portion 1405 is airtight. In some embodiments, a first portion of the head portion 1410 may be separable from a second portion of the head portion 1410.

In some embodiments, such as the embodiments of FIGS. 13A, 13B, and 13C, the measurement device 1300 is configured for use independent of a medication delivery apparatus. Such a device may be used to monitor lung function in individuals with a respiratory condition and/or athletes or other individuals interested in tracking lung function and health. The device of some embodiments includes a housing unit 1302 having an optional display unit, such as, for example, an LCD display screen 1304, and an aperture 1310 through which an individual can forcefully expel air. Expired air traveling through the aperture enters an interior of the housing unit 1302 where spirometry components and/or cardiopulmonary biomarker detection components are stored. An appropriate processor and circuitry are also stored within the interior of the housing unit 1302. Any appropriate spirometry components, cardiopulmonary biomarker detection components, processor, and circuitry components may be used, for example, any components described herein in the discussion of other embodiments.

In some embodiments, such as, for example, the embodiment of FIG. 13A, the measurement device 1300 is an independent, stand-alone device configured to: display to a user calculated metrics related to lung function on an integrated display screen, wirelessly transmit unprocessed, semi-processed, and/or processed data to a remote personal computing device, and/or wirelessly transmit unprocessed, semi-processed, and/or processed data to a server. In some such embodiments, the measurement device 1300 is attached to a keychain, clip, lanyard, or chain or is otherwise configured to be worn around an individual's arm or neck or on an individual's clothes. In other embodiments, such as, for example, the embodiments of FIGS. 13B and 13C, the measurement device 1300 is configured to couple directly to a smartphone, tablet, laptop, or other portable computing device, such as, for example, via a connection 1312 into the headjack port or a connection 1314 into the electrical charging port. The portable computing device may be used to analyze, display, and/or transmit data. In some such embodiments, display outputs may be presented on a display screen of the portable computing device and no display screen may be present on the measurement device.

Figure 19:
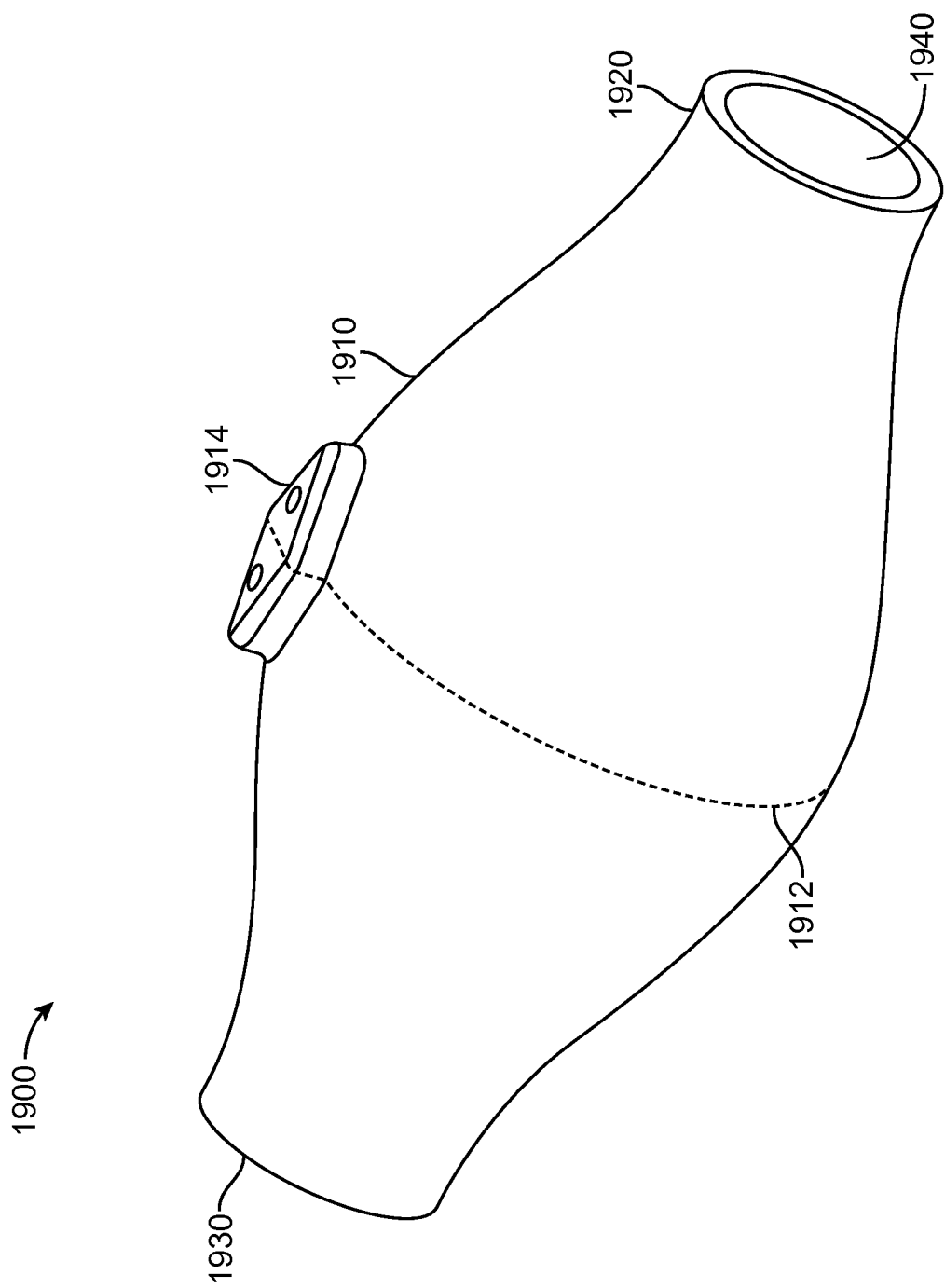
FIG. 19 depicts a front (proximal) perspective view of another embodiment of a handheld measurement device for monitoring lung function.

Yet another embodiment of a measurement device is provided in FIG. 19. As shown, the measurement device 1900 is substantially formed of a flow head 1910. The flow head 1910 may taper at a proximal end to form a mouthpiece 1920. In some embodiments, the flow head 1910 tapers at a distal end to form a coupling feature 1930 configured to couple to a spacer or an inhaler either directly or with the addition of a connector. In various embodiments, a lumen 1940 extends through the measurement device 1900 from the proximal end to the distal end. In some embodiments, a mesh (not visible) is disposed within the lumen 1940, extending across the entire cross-section of the lumen 1940 at a discrete location. In some locations, the mesh extends across the lumen 1940 at the widest portion of the measurement device 1900 (i.e., at the location of the greatest diameter). In some embodiments, the diameter of the lumen 1940 on the proximal and distal sides of the mesh is equal. In some embodiments, a first portion of the flow head 1910 is separable from a second portion of the flow head 1910, for example, at a connection 1912. The first portion and the second portion of the flow head 1910 may be securely but separably connected via a friction fit, complementary threading, or any other suitable connection feature. When separated, the mesh may be accessible for cleaning and/or replacement. In some embodiments, when the two sides are separated, an internal view of the measurement device 1900 looks substantially like the cross-sectional view of FIG. 17 with the processor and circuitry stored in a protective compartment within the flow head 1910. Additionally, as with other embodiments described above, in some embodiments, a pressure sensor is provided within the measurement device 1900 to sense any pressure differential that may be present within the device between the proximal and distal sides of the mesh. Two holes 1914 may extend through a wall of the flow head 1910 on opposing sides of the mesh to relay baseline pressure sensor inputs to the pressure sensor.

Figure 21:
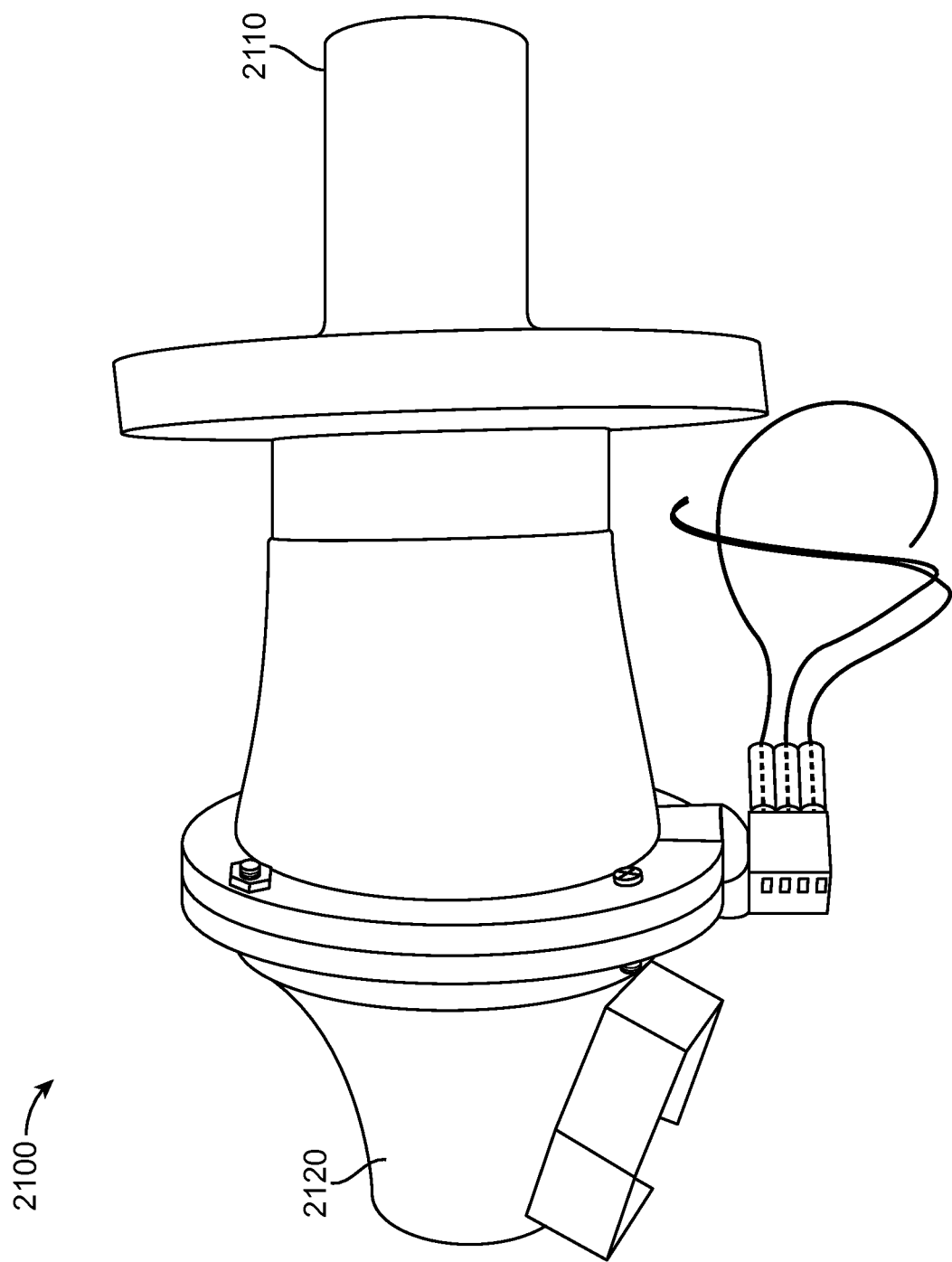
FIG. 21 depicts an embodiment of a handheld measurement device having a removable mouthpiece.

One non-limiting embodiment of a portable, handheld measurement device having a removable mouthpiece is shown in FIG. 21. The device 2100 is formed of a mouthpiece 2110 and a flow head 2120. As with other embodiments provided herein, the interior of the flow head includes: a protective compartment housing circuitry and a processor, and a lumen through which a patient can breathe air. The lumen includes a mesh screen designed to create a pressure differential on opposing sides of the mesh when air is expressed through the lumen. In some embodiments, the interior of the flow head 2120 has the same or substantially the same configuration as the flow head interior shown in FIG. 17. The mouthpiece 2110 of the device 2100 is removable so that it may be cleaned or replaced between uses. Such an embodiment may allow the same measurement device to be used with a plurality of patients, for example, in a clinical setting. In some embodiments, a bacteria filter is disposed within the lumen of the mouthpiece 2110, for example, across an entire cross-sectional area of the mouthpiece lumen. In some embodiments, the filter is placed across the portion of the mouthpiece lumen having the largest diameter. In various embodiments, the bacteria filter is formed of an extremely low resistance material. In one non-limiting example, the bacteria filter is formed of a cloth mesh.

Figure 8:
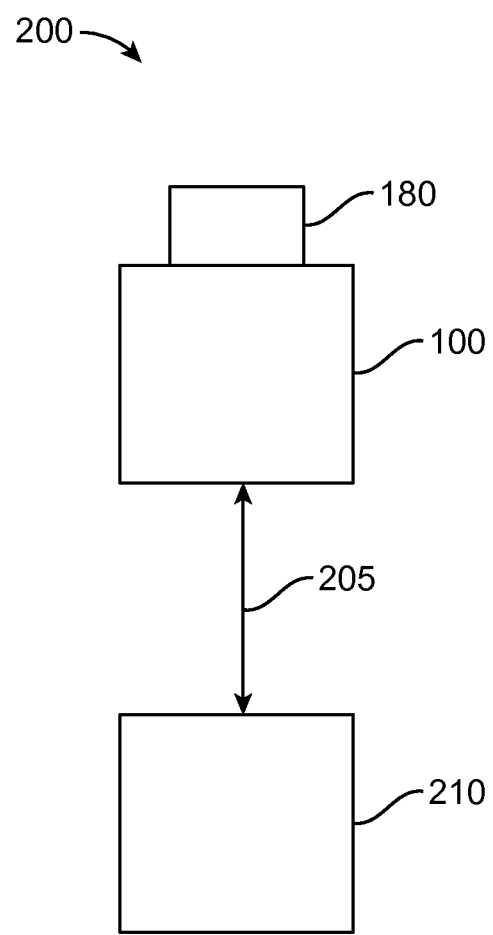
FIG. 8 depicts a schematic block diagram of one embodiment of a system for monitoring lung function.
Figure 9:
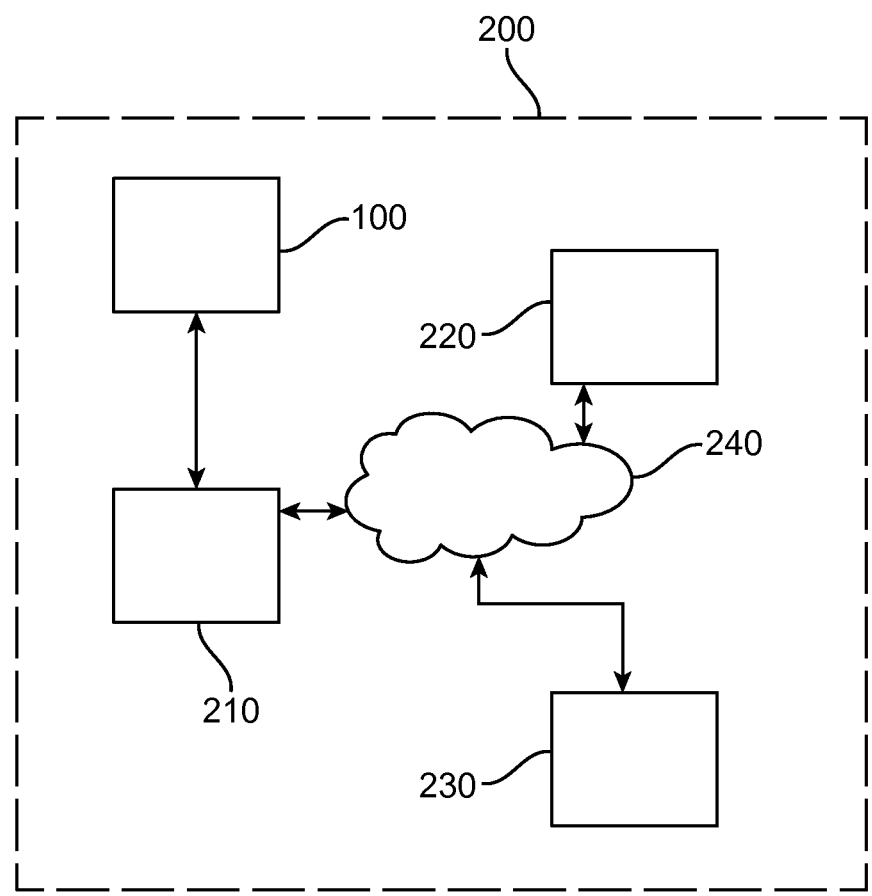
FIG. 9 depicts a schematic block diagram of another embodiment of a system for monitoring lung function.

As shown in the block diagrams of FIGS. 8 and 9, some embodiments described herein are directed to a system for monitoring and treating asthma or other chronic respiratory conditions. In the simple system of FIG. 8, the measurement device 100, which is coupled to an aerosol medicine canister 180, is in communication via communication link 205 with a remote computing device 210. While the measurement device is shown to be device 100, this is done for ease of reference only and one of skill in the art will appreciate that any embodiment of a measurement device described herein (e.g., measurement device 1000, 1200, 1300, 1400, 1700, 1800, or 1900) may form part of the described system for monitoring and treating asthma or other chronic respiratory conditions. The remote computing device 210 may be a user's mobile computing device such as a smartphone or tablet or a user's laptop or desktop computer. The communication link 205 may be a wired or wireless connection. In each embodiment, the communication link 205 is a forward communication link sending data from the measurement device 100 to the remote computing device 210. In some embodiments, the communication link 205 also includes a backwards communication link, which sends data or requests for data from the remote computing device 210 to the measurement device 100. In some embodiments, the remote computing device 210 is in wireless communication with the handheld measurement device 100. In such embodiments, the communication link 205 may include radiofrequency technology, for example, Bluetooth® or near field communication technology. In other embodiments, the remote computing device 210 can be temporarily connected physically to the handheld measurement device 100 to transfer data. In such embodiments, the communication link 205 may include one or more cables and/or a TRS plug, USB, micro-USB, mini-USB, or other port, plug, or other I/O hardware connection. In some embodiments, the remote computing device 210 includes, or is connected to, memory storing instructions related to signal processing; in some such embodiments, data processing and calculations such as FEV calculations are performed by the remote computing device 210.

In the system of FIG. 9, the system further includes a server 220, such as a database server, application server, and/or a web server, and optionally, an additional user's computer 230. The remote computing device 210, server 220, and optional additional user's computer 230 are each connected to a communication network 240. In various embodiments, communication between the remote computing device 210, the server 220, and the additional user's computer 230 occurs over a wireless communication network to which each computing device is connected, such as, for example, over a mobile WiMAX network, LTE network, Wi-Fi network, or other wireless network. In other embodiments, the communication between the computing devices occurs over the internet via a wired network, such as a DSL cable connection, or over Ethernet or an intranet.

In a preferred embodiment, the measurement device 100 and remote computing device 210 are in wireless communication, and data is sent from the measurement device 100 periodically or each time a sensor or sensor circuit within the device 100 is activated. The transmitted data includes digital signals providing pressure and/or cardiopulmonary biomarker measurements from the pressure sensor and/or cardiopulmonary biomarker sensor, respectively. In one embodiment, the remote computing device 210 is a user's mobile phone or other mobile computing device. Upon receiving the signal data, for example, via wireless transmission of signals, the remote computing device 210, optionally performs some signal processing or analysis, and transmits the raw data and/or more refined data to the server 220 for further processing and/or storage. Processing may include assessing the pressure reading to determine if the patient was inhaling or exhaling into the measurement device 100. If inhaling, a medication dosage counter may increment. If exhaling, calculations are performed to convert the pressure signals into useful spirometry measures, for example, any of the spirometry measures described above. The cardiopulmonary biomarker readings, if present, are also stored. By storing and accumulating data about medication usage and lung function over time, trends will become apparent. Users of the system will be able to track the severity levels of a patient's acute respiratory attacks and determine if medication was administered at appropriate times and in appropriate doses. Moreover, overtime, baseline values will be identifiable to users, and preferably, to the system.

In some embodiments, a patient uses the measurement device 100 multiple times a day. For example, in one embodiment, the patient takes preventative, maintenance asthma medicine twice daily. Preferably, before or after inhaling the asthma medicine from the device 100, the patient exhales forcefully into the device 100, generating pressure readings, and optionally, cardiopulmonary biomarker readings, for the system 200. Additionally, the measurement device 100 is used to administer fast-acting drugs when the patient is experiencing an attack. Preferably, at the first sign of acute asthma symptoms, the patient will exhale forcefully into the device 100 to monitor current pressure readings, and cardiopulmonary biomarker readings if available.

Data stored in the server 220 is accessible to the patient via the patient's remote computing device 210 and may also be accessible to other users with proper authentication credentials. For example, the data may be accessible to any computing device 230 that has installed the appropriate system software, for example, by downloading the system's mobile application, upon entering an authorized password and/or a unique identifier. In this manner, a patient may grant access to his or her physician, family member, or caregiver to help monitor and track the patient's lung function.

In various embodiments, the server 220 may include a database, which stores user profile information for each patient and each additional user of the system. The stored user profile information may include information that is accessible and editable by a user such as a user name, password, a list of other users to which the particular user is connected (i.e., has granted or received permission to access stored lung function data), and basic biographical information, such as the birthdate and gender of the user. The editable biographical information may also include health-related information such as the height, weight, and health conditions of the user. In some embodiments, the database also stores information that is not editable by a user. For example, non-editable lung function data acquired from a measurement device may be linked to a particular patient and stored within the server.

In various embodiments, the data is presented in an easy-to-understand manner. For example, in one embodiment, following every forced expiration, spirometry measures are calculated and the data is compared to stored baseline data or threshold values. This step may be performed by the server in accordance with instructions stored in the server memory. Information regarding the spirometry metrics or comparisons may then be returned over a communication link to the remote computing device 210 or to another computing device 230 for graphical display. In other embodiments, at least some spirometry calculations are performed directly by the remote computing device 210 in accordance with instructions stored in memory. In various embodiments, the remote computing device 210 and other computing devices 230 are each in wired connection with an output display, such as a touchscreen or monitor, allowing it to display a graphical user interface (GUI).

Figure 11A:
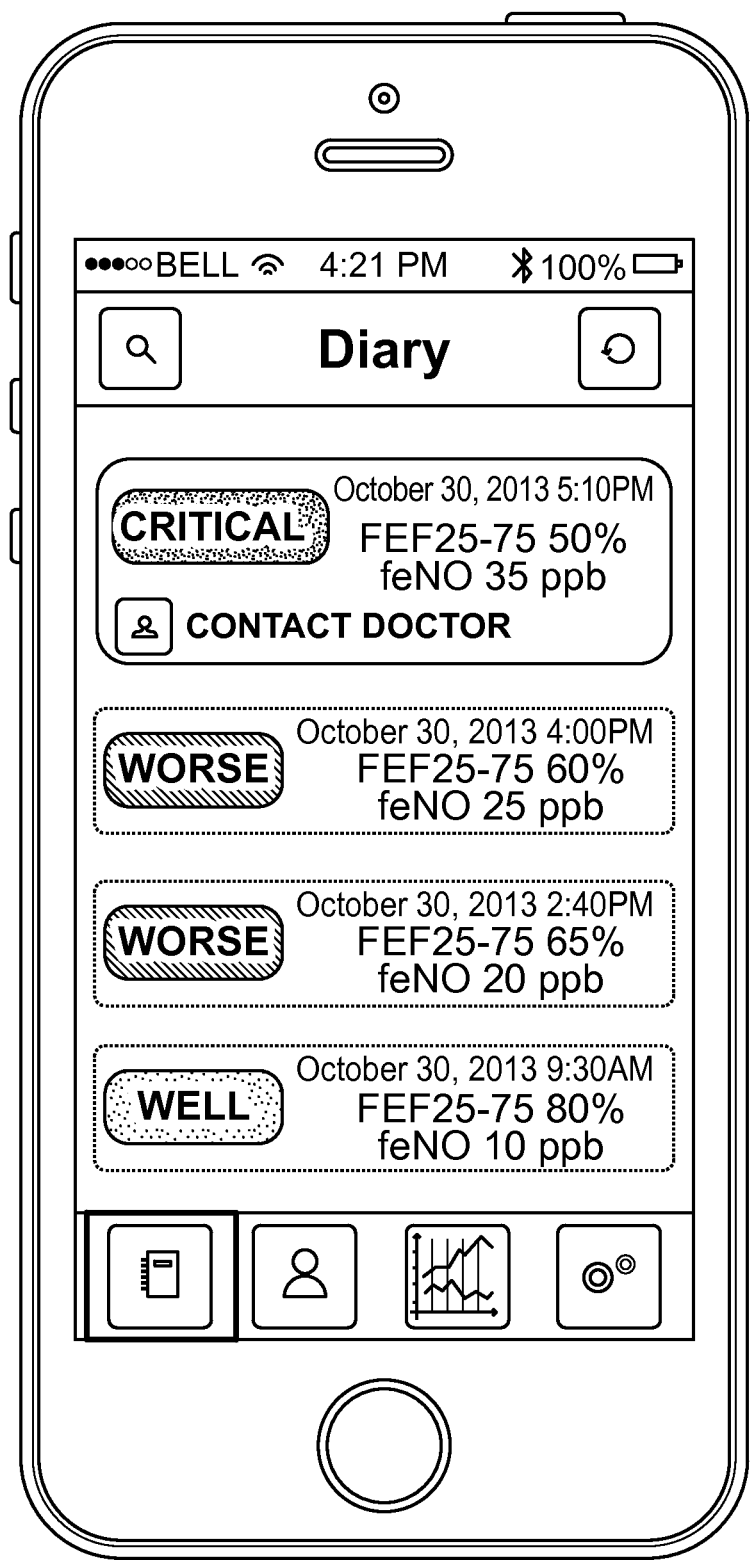
FIGS. 11A-11C depict various embodiments of user interfaces displayed on a remote computing device in accordance with principles of the present disclosure.
Figure 11B:
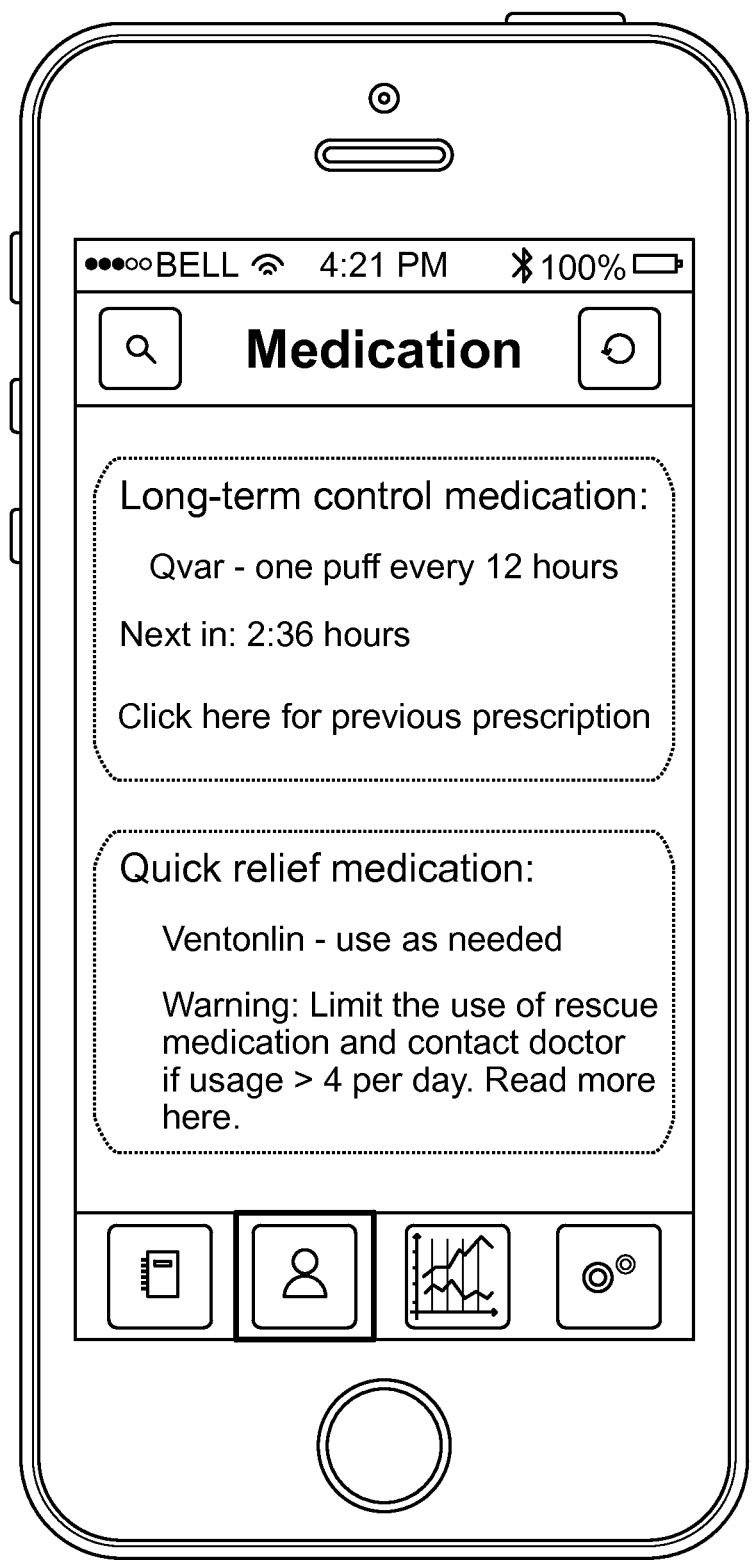
Figure 11C:
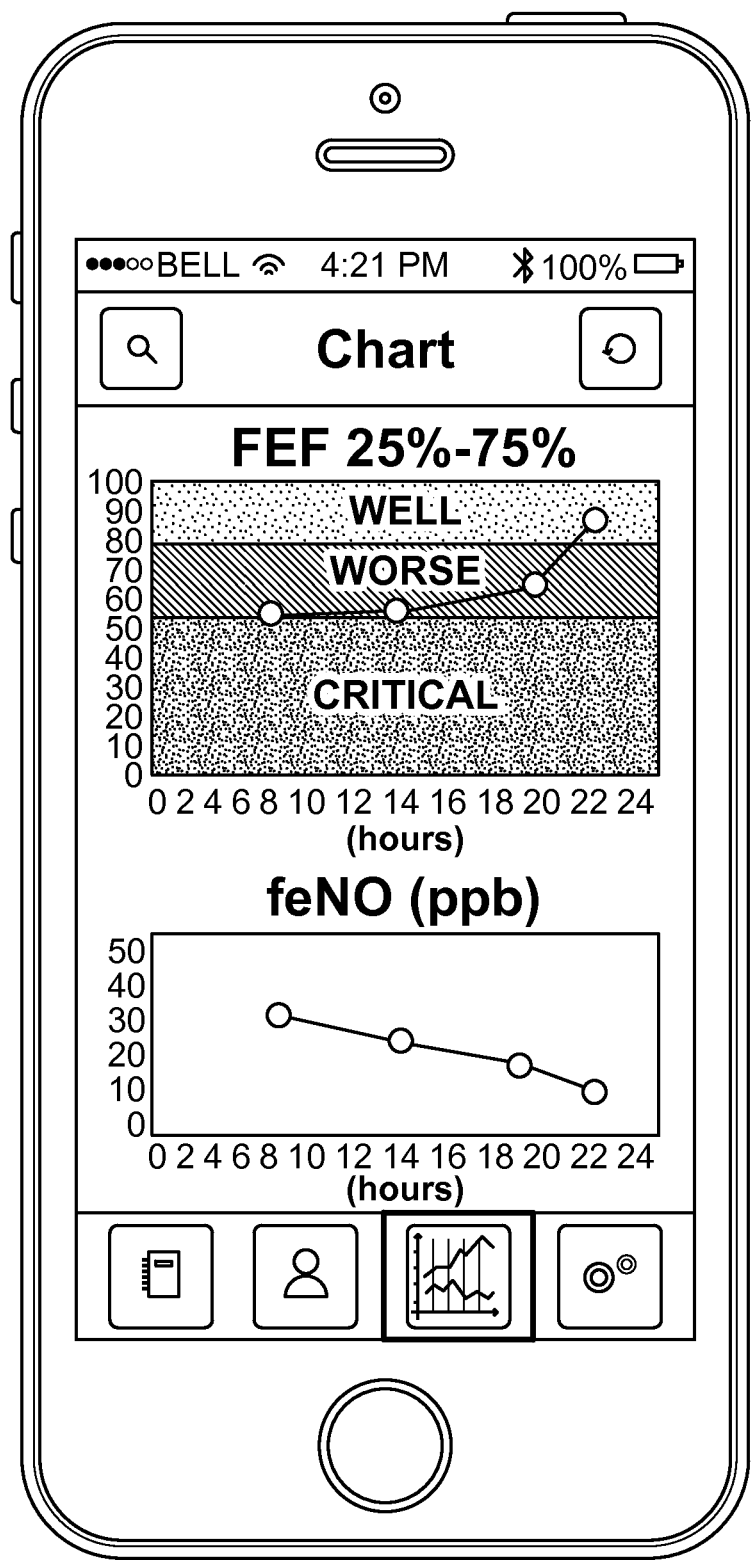
Figure 12A:
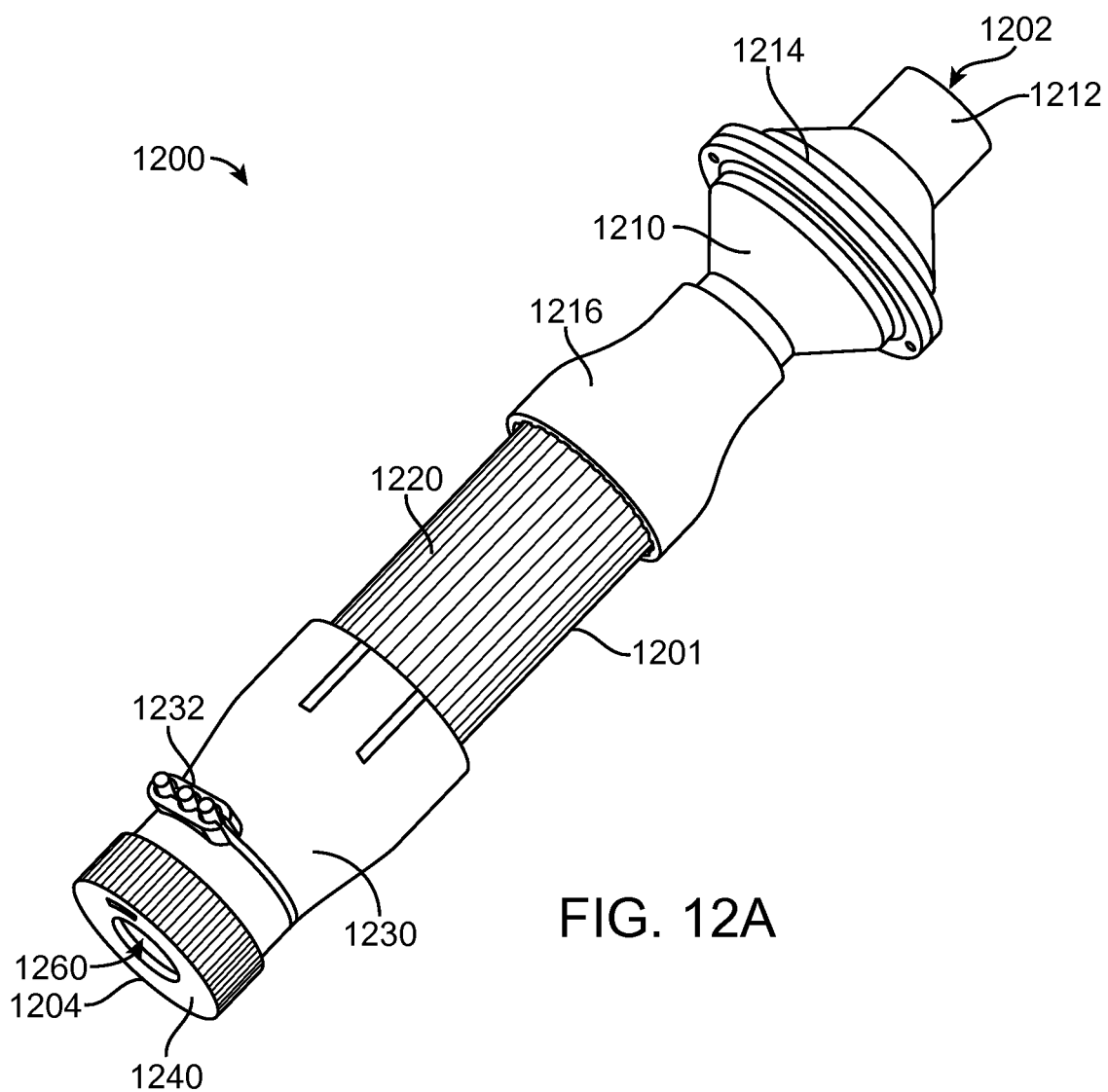
FIG. 12A depicts a schematic distal perspective view of another embodiment of a portable measurement device for monitoring lung function.
Figure 12B:
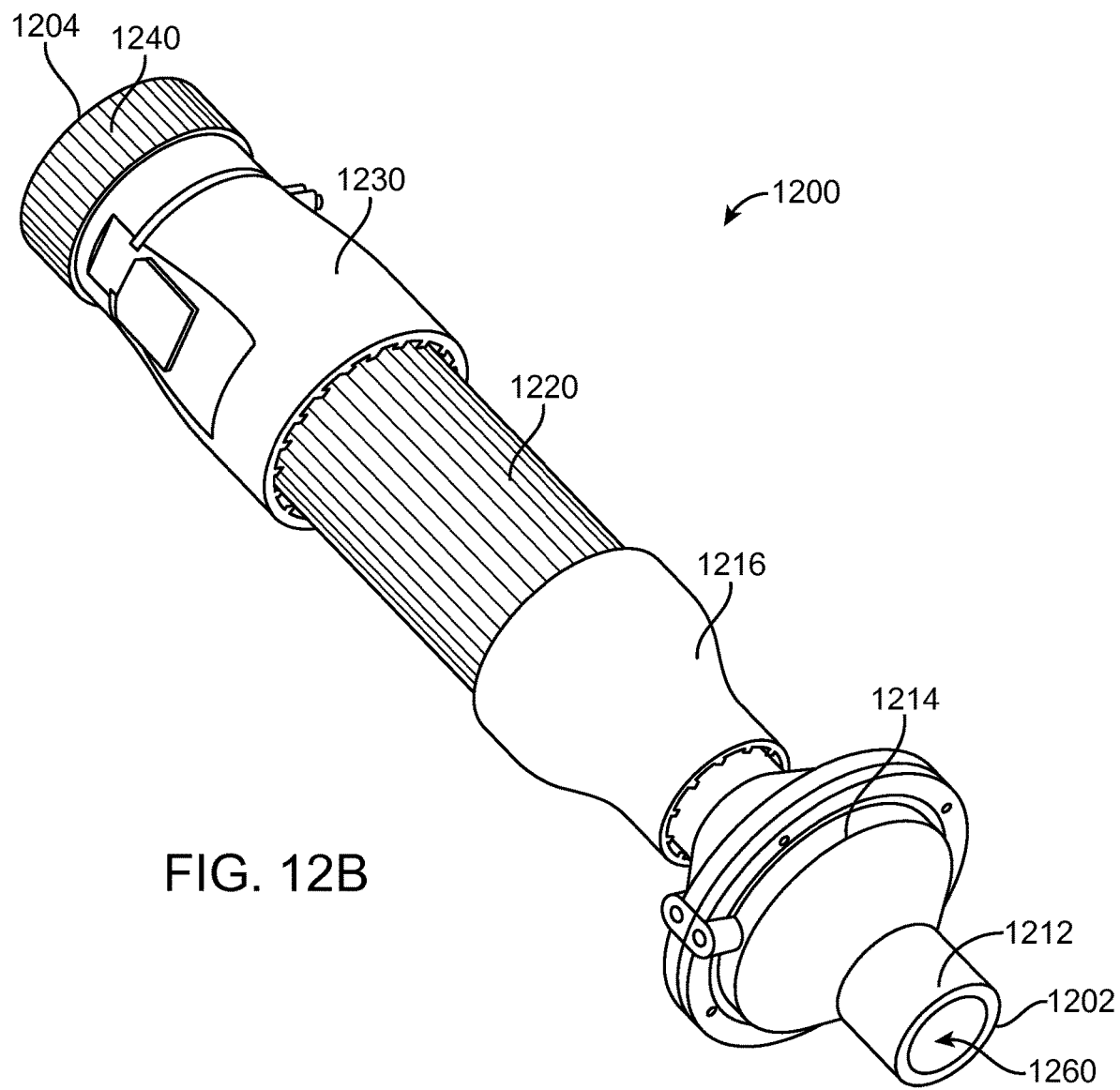
FIG. 12B depicts a schematic proximal perspective view of the measurement device of FIG. 12A.
Figure 12C:
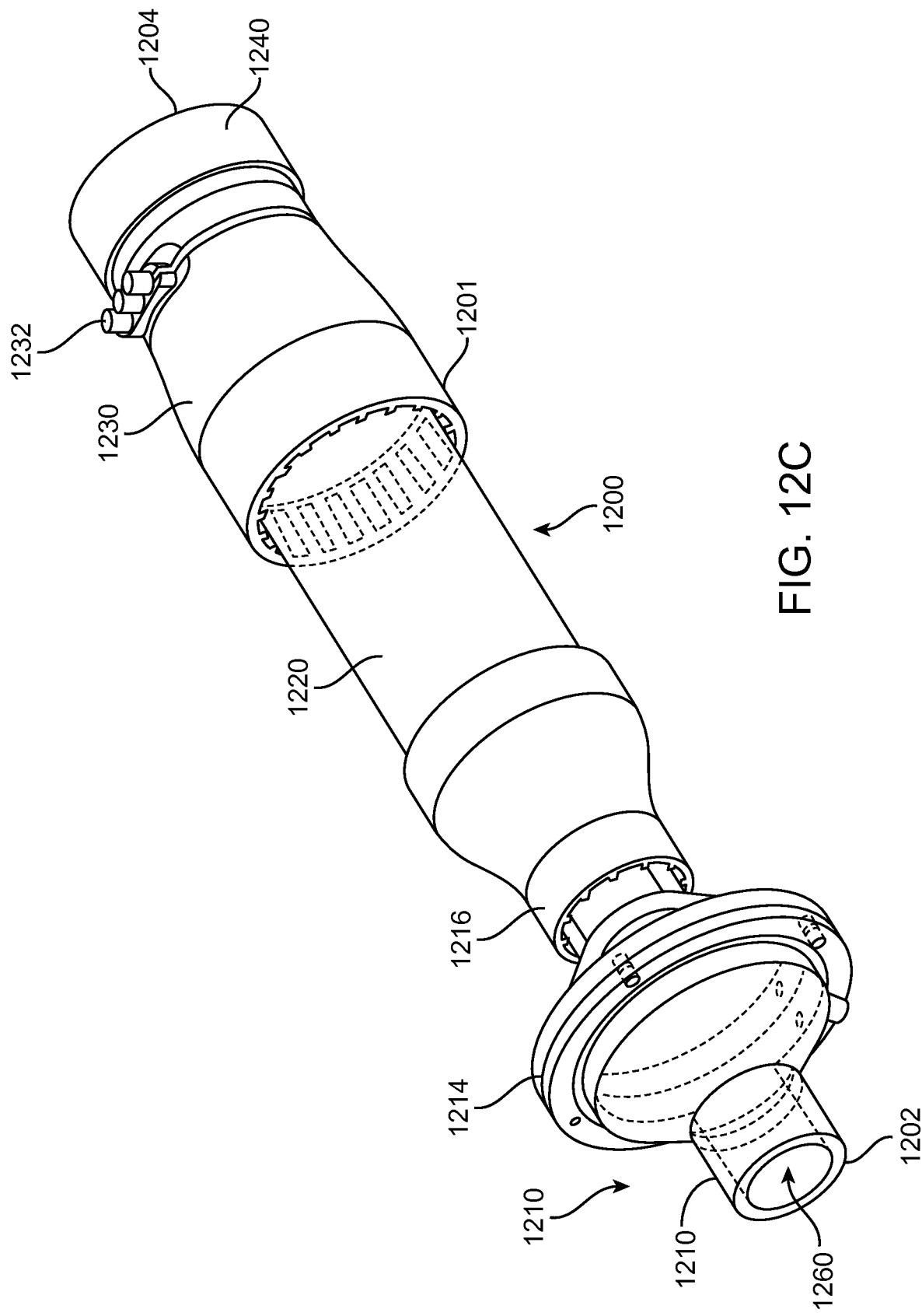
FIG. 12C depicts another schematic proximal perspective view of the measurement device of FIG. 12A.
Figure 12D:
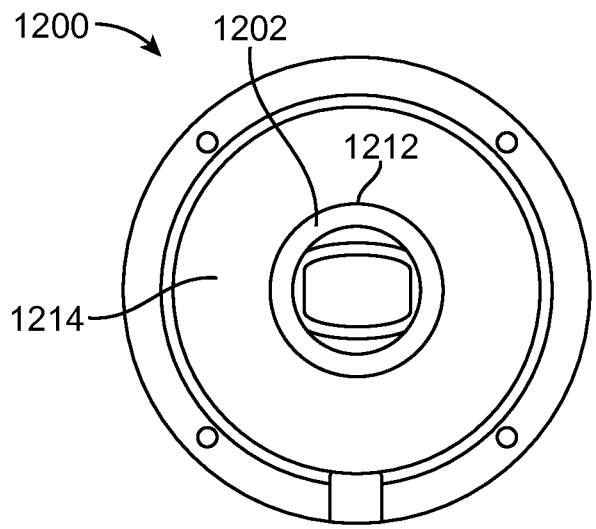
FIG. 12D depicts a schematic front (proximal) view of the measurement device of FIG. 12A.
Figure 12E:
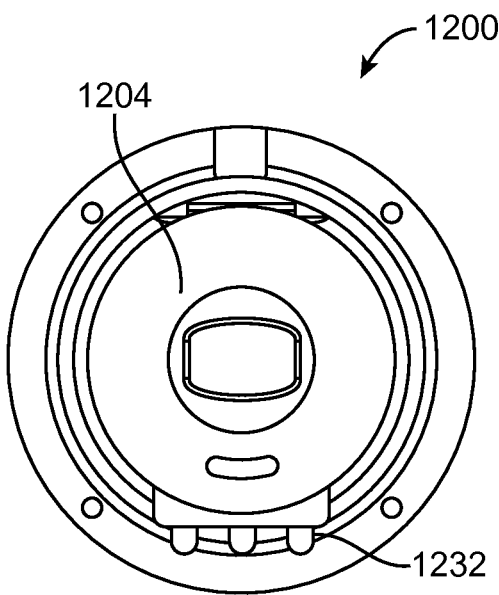
FIG. 12E depicts a schematic back (distal) view of the measurement device of FIG. 12A.
Figure 12F:
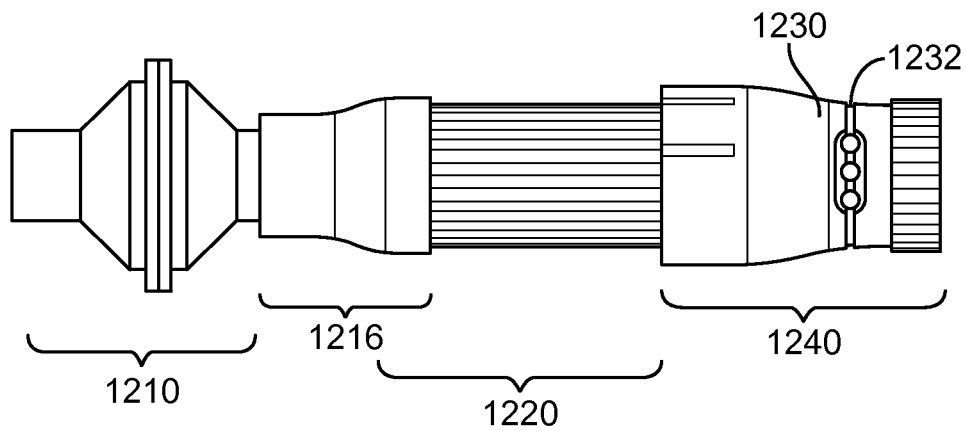
FIG. 12F depicts a schematic side view of the measurement device of FIG. 12A.

Examples of the GUI are provided in FIGS. 11A-11C. By interacting with the GUI, a user, such as a patient, patient's caregiver, or physician, can interact with the current data and stored data, requesting information from the server 220, as needed, viewing data transmitted from the server 220, and adding data to memory in the server 220. In one example, if the recorded measurements deviate from the healthy baseline values by more than a certain percent, instructions may be sent from the server 220 back to the patient's remote computing device 210 instructing the remote processor 210 to present a warning. Upon receiving said instructions, the remote computing device 210 may be configured to send data signals to the output display such that a warning appears on the GUI on the screen of the patient's remote computing device. The warning may include the relevant numerical values of the reading or simply a warning indication such as a yellow or red light or a warning sound. It may present an alert asking the patient if a call, text message, email, or other alert should be made or sent to an emergency contact or emergency responders.

In some embodiments, the GUI also helps users track historical data. For example, as shown in FIG. 11A, a log of important metrics, such as, for example, FEF 25-75% and nitric oxide levels, may be stored by the server 220, transmitted to the remote computing device 210, and displayed via the GUI. In certain embodiments, a user may select the specificity of data and the time frame of historical data to display. For example, a user may opt to display: all readings within a single day, all readings within a week, the average reading each day of a week, the average reading within each day of a month, etc. A user can review data from the current day, week, month, etc. and/or review data from a different specified period of time in the past. As shown in FIG. 11A, in some embodiments, the log or diary includes the date and time of each recording, along with important metrics, and a symbol indicating whether the patient is "well," "worse," or "critical." In order to assign such categories to each recording, the remote computing device 210 or server 220 of various embodiments compares the recorded levels to stored threshold values or historical patient-specific values. As shown in FIG. 11C, in some embodiments, the historical data can additionally or alternatively be displayed to a user via a GUI in a graphical format (e.g., in a line graph or bar graph).

As shown in FIG. 11B, in some embodiments, the GUI also displays reminders and alerts to a patient, such as, for example, to indicate when it is time to take another dose of medication. In some embodiments, after the remote processor 210 or server 220 identifies that a patient inhaled air and medicine from the measurement device 100, the patient is prompted in the GUI to select whether the dispensed medication was a fast-acting drug or a long-term control medication. The user input received by the remote processor 210 then allows the remote processor 210 or the server 220 to increment an appropriate medication counter.

Figures 22A, 22B:
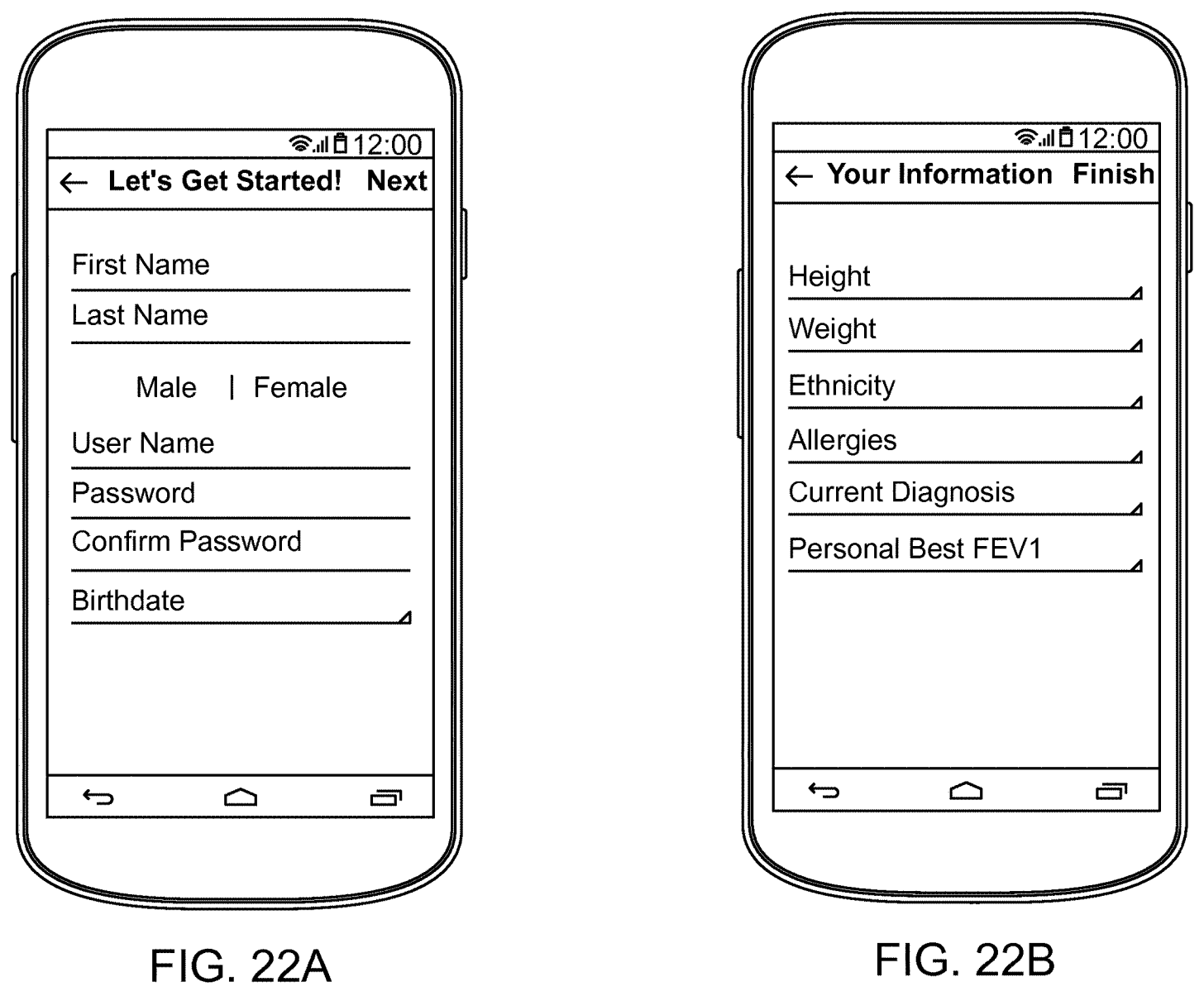
Figure 22E:
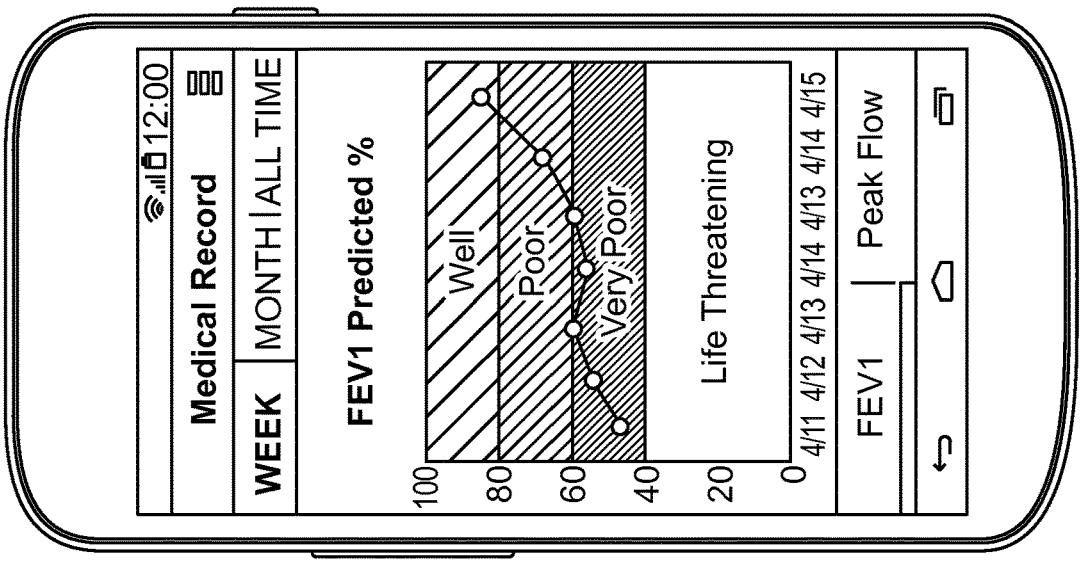

Additional embodiments of the GUI are displayed in FIGS. 22A-H. As shown in FIGS. 22A-B, once a patient downloads the software application onto their remote computing device, in some embodiments, the patient is prompted to create an account. This may require the patient to enter their name, a unique user name, and password. It may also require biographical information; for example, in some embodiments, the patient is prompted to provide one or more of the patient's: gender, birthdate, height, weight, ethnicity, allergies, current diagnosed illnesses (respiratory or otherwise), and one or more personal best spirometry readings, if known. In some embodiments, an account will be created for a patient upon entering this information and selecting the finish icon. In some embodiments, this information is entered using a keyboard; in other embodiments, it may be entered using a touchscreen or voice recognition technology.

Figure 22D:
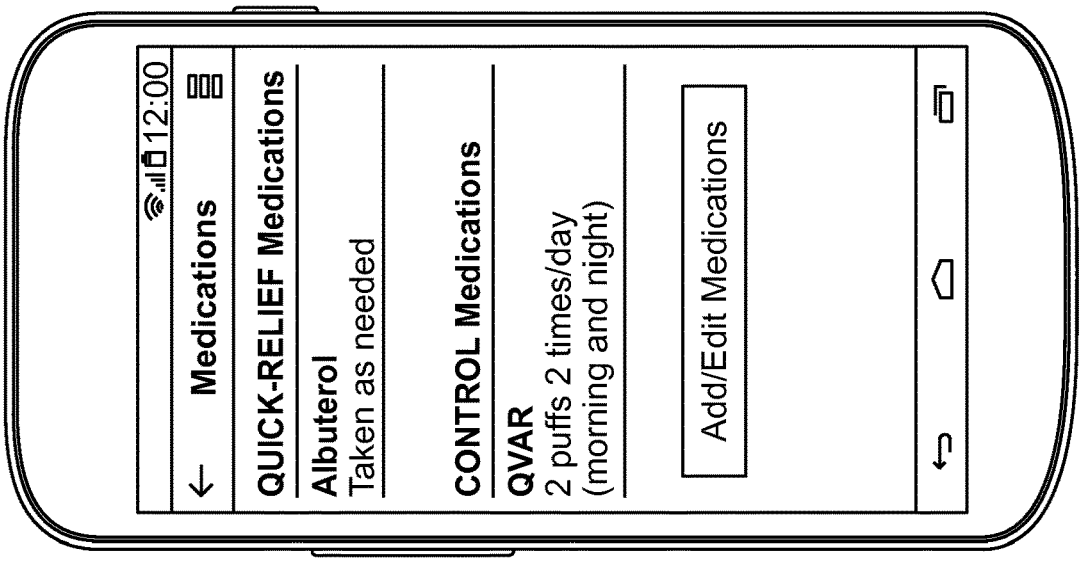
Figure 22C:
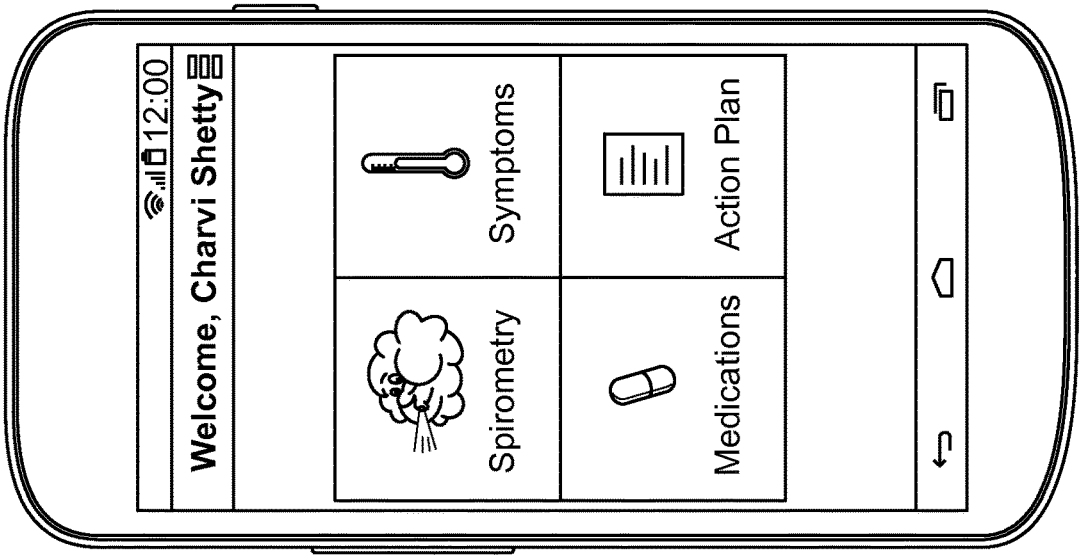

Once a patient is provided access, the patient may be directed to a home screen of the patient GUI. A non-limiting example of the home screen is shown in FIG. 22C. As shown, a patient may be presented with a plurality of options displayed as selectable icons. For example, selection of a "spirometry" icon may put the device in spirometry measurement collecting mode. Selection of a "medications" icon may route a patient to a screen where the patient can enter new medications or review prescribed medications and administration instructions. An example of the medication screen is shown in FIG. 22D. Returning to FIG. 22C, in some embodiments, a patient may be able to maintain a log of symptoms upon selecting the "symptoms" icon. Additionally or alternatively, a patient may be able to maintain a log of perceived triggers and/or a log of general health and fitness status. The patient may be able to enter information such as how much they slept or exercised and/or what they ate within their general health log. Patients and/or physicians may be able to create and edit action plans indicating what a patient should do in various scenarios, based for example, on lung function measurements. A patient may be able to easily access their patient-specific action plan at any time through the patient GUI if they need a reminder of the plan.

Using the patient GUI, a patient may be able to graphically track spirometry readings over time. One non-limiting example of FEV1 tracked over a week is shown in FIG. 22E. As also shown, a patient may be able to switch through different readings, for example, FEV1, PEFR, FVC, FEF 25-75, etc. A patient may additionally or alternatively be able to switch through various time intervals for display, for example, viewing a graph of spirometry readings taken over the course of a day, week, month, year, or the lifetime of using the device. With such a GUI, a patient may be able to easily identify trends in the patient's data.

Figure 22H:
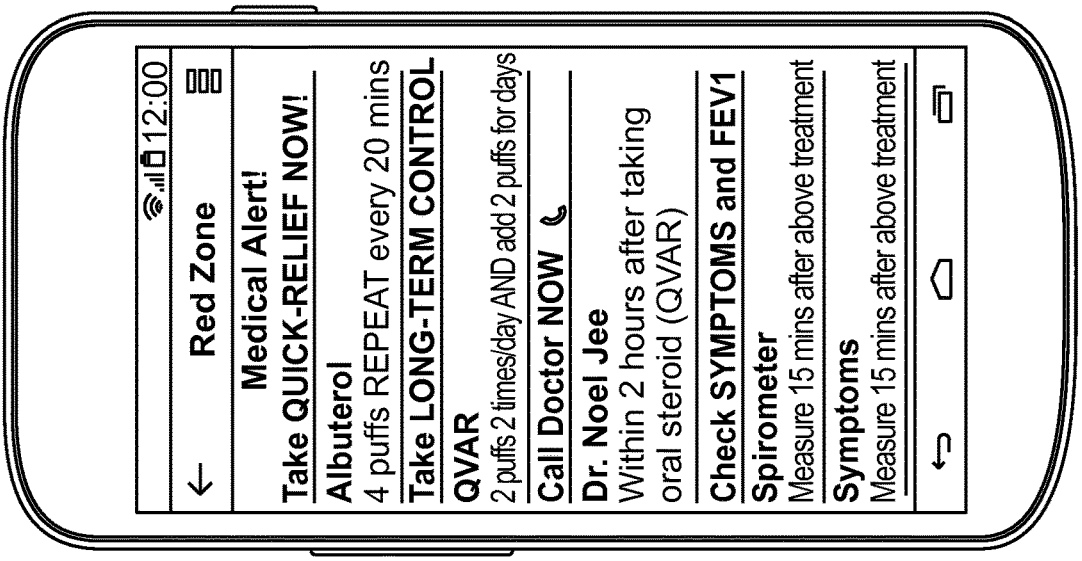
Figure 22G:
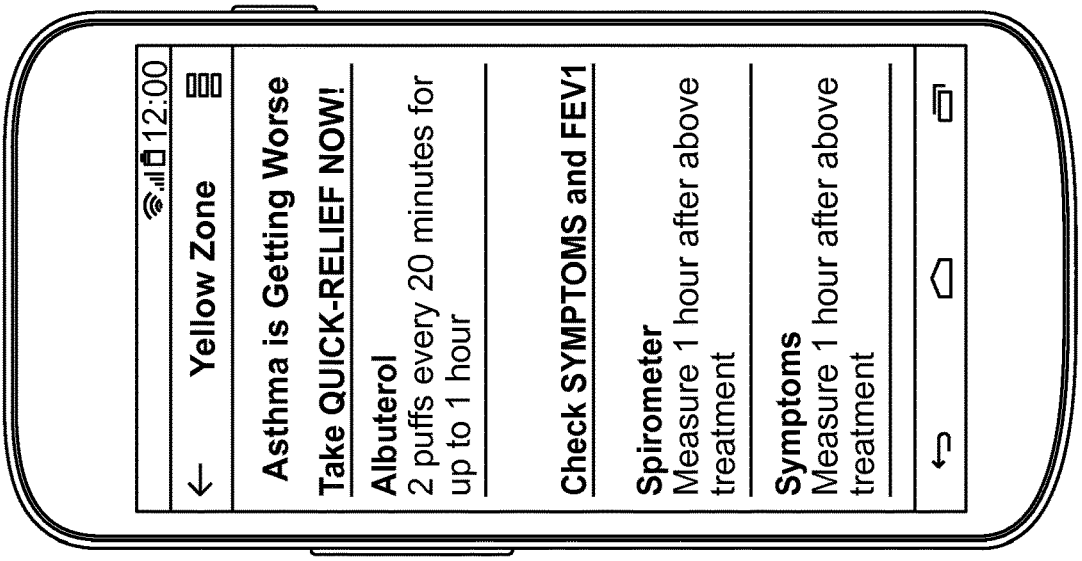
Figure 22F:
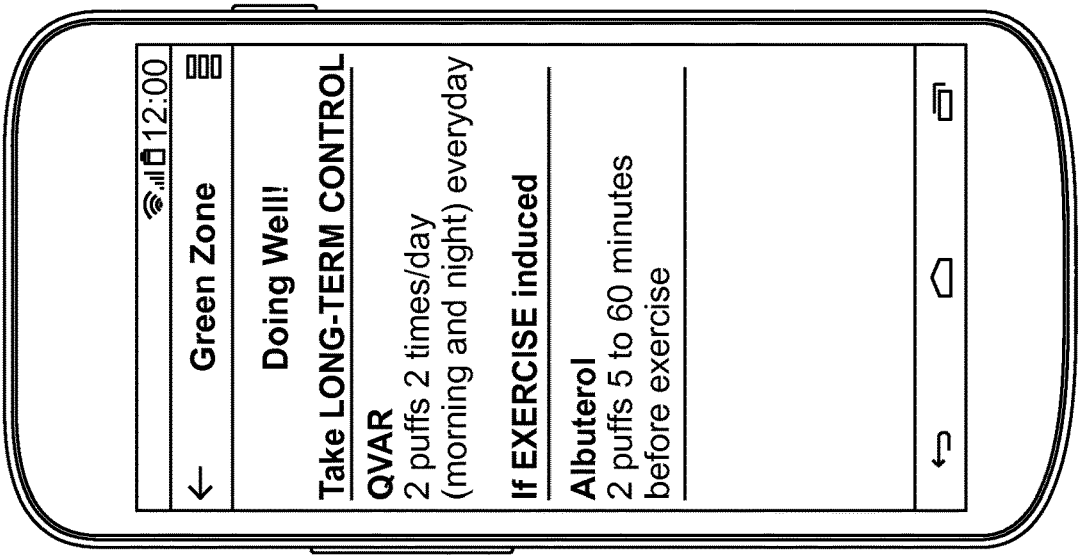

As shown in FIGS. 22F-22H, in some embodiments, following a patient's exhalation into the handheld measurement device and transmission of the data to the patient's remote computing device, the GUI onboard the remote computing device may provide feedback to the patient in the form of easy-to-interpret results and recommendations. For example, in some embodiments, if a spirometry reading is identified to be within a healthy range (e.g., by comparing it to known threshold values, known health values, and/or a patient-specific healthy baseline value), a display such as the one provided in FIG. 22F may be presented to the patient, indicating the patient is doing well and providing recommendations to maintain success. A portion of the GUI may appear green. In some embodiments, if a spirometry reading is identified to be in an unhealthy and/or potentially dangerous range, a display such as the one provided in FIG. 22H may be presented to the patient, indicating the patient has a medical alert. A portion of the GUI may appear red. The display may present suggestions to the patient, such as medications to take immediately or a monitoring regime the patient should follow with the measurement device. The patient may also be presented with the option to call a doctor or caregiver stored within the patient's profile information. If a reading is between a healthy and dangerous range, a display such as the one provided in FIG. 22G may be presented to the patient, indicating the patient should be cautious; recommendations for improving the patient's current lung performance may be presented to the patient. A portion of the GUI may appear yellow.

Returning to FIG. 9, in some embodiments, when the remote computing device 210 sends pressure and/or cardiopulmonary biomarker sensor data to the server 220, it also sends additional data, such as a time stamp and/or location data. The location data may be obtained from a GPS unit in the remote computing device 210 or from a GPS unit built directly into the measurement device 100. Using the time and location data, the server 220 may also request relevant environmental data from other servers and computing devices corresponding to the time and location of the sensor reading. For example, with every pressure and/or cardiopulmonary biomarker reading, the server may also obtain and save information about the time of day, the location of the patient, and the weather conditions, pollen count, and pollution levels at or near the patient's location at that time. With this additional data, a user, such as a patient, a patient's parent, or a patient's healthcare provider may be able to identify common triggers of a patient's acute symptoms. With this knowledge, a patient may be able to make more informed decisions and take actionable steps to avoid his or her known triggers.

In some embodiments, to protect patient safety and confidentiality, if a user wishes to gain access to a patient's stored lung function data, they must be invited by the patient. In some such embodiments, the GUI on the remote computing device 210 of a patient includes an option to send invites. A patient may then enter into the GUI the name and email address and/or phone number of an individual to invite, and the system will send a text message or email to the individual with a link to join the system's network and/or connect to the inviting patient.

In other embodiments, in order for a physician to gain access to a patient's stored lung function data, a patient must provide consent during a visit to the physician within a physical or electronic consent form. The physician can then submit the consent form to a system administrator and be granted access to the patient's data. In some embodiments, the patient's data is then sent periodically or when requested to the patient's electronic medical record (EMR). In some embodiments, the patient's data is pushed to the patient's EMR in an interactive format, for example, in a format that is compatible and/or native to the EMR system. In other embodiments, the patient's data is made available as a pdf document, which can be uploaded and saved as an attachment to the patient's EMR.

In some embodiments, a separate GUI is provided to physicians. The GUI, referred to as a physician portal, may be accessible to physicians who have been verified to be physicians by the system or a system administrator. Upon entering a recognized username and password, a physician may be able to view an interactive list of all patients to which the physician has connected. By selecting any one of the patients, the physician may be able to view detailed information about the patient's lung function. A log of readings from the patient's measurement device may be viewable. Additionally or alternatively, easy to read graphs may be provided, each of which plot, over time, a spirometry metric calculated from readings received from a patient's measurement device. Additionally, in some embodiments, if any connected patient of the physician has experienced a bad attack of symptoms, as recorded by a patient's measurement device, an alert may be emailed or texted to the patient's physician or may appear as a pop up or as a flagged or highlighted entry within the physician's portal.

Figure 23A:
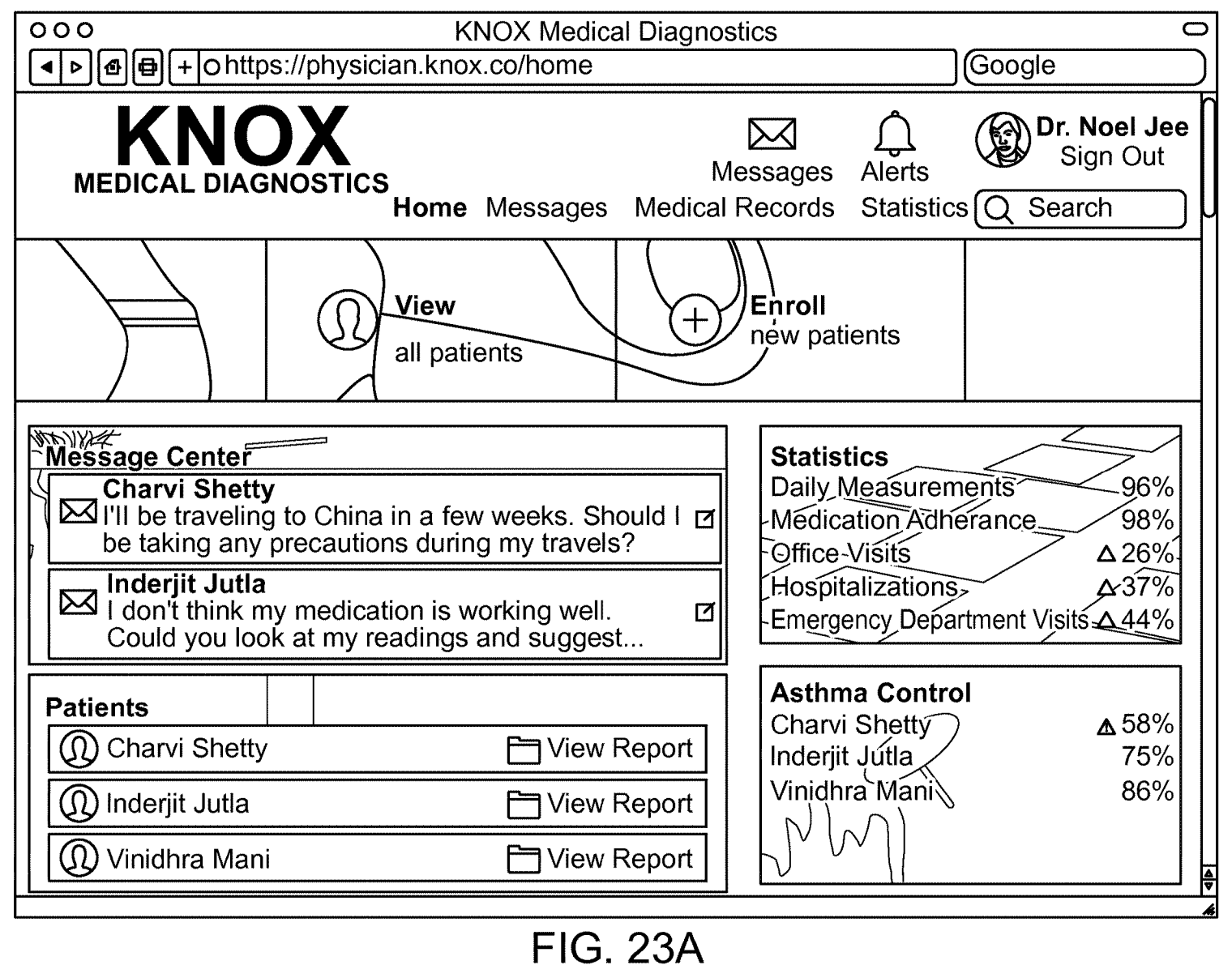
Figure 23B:
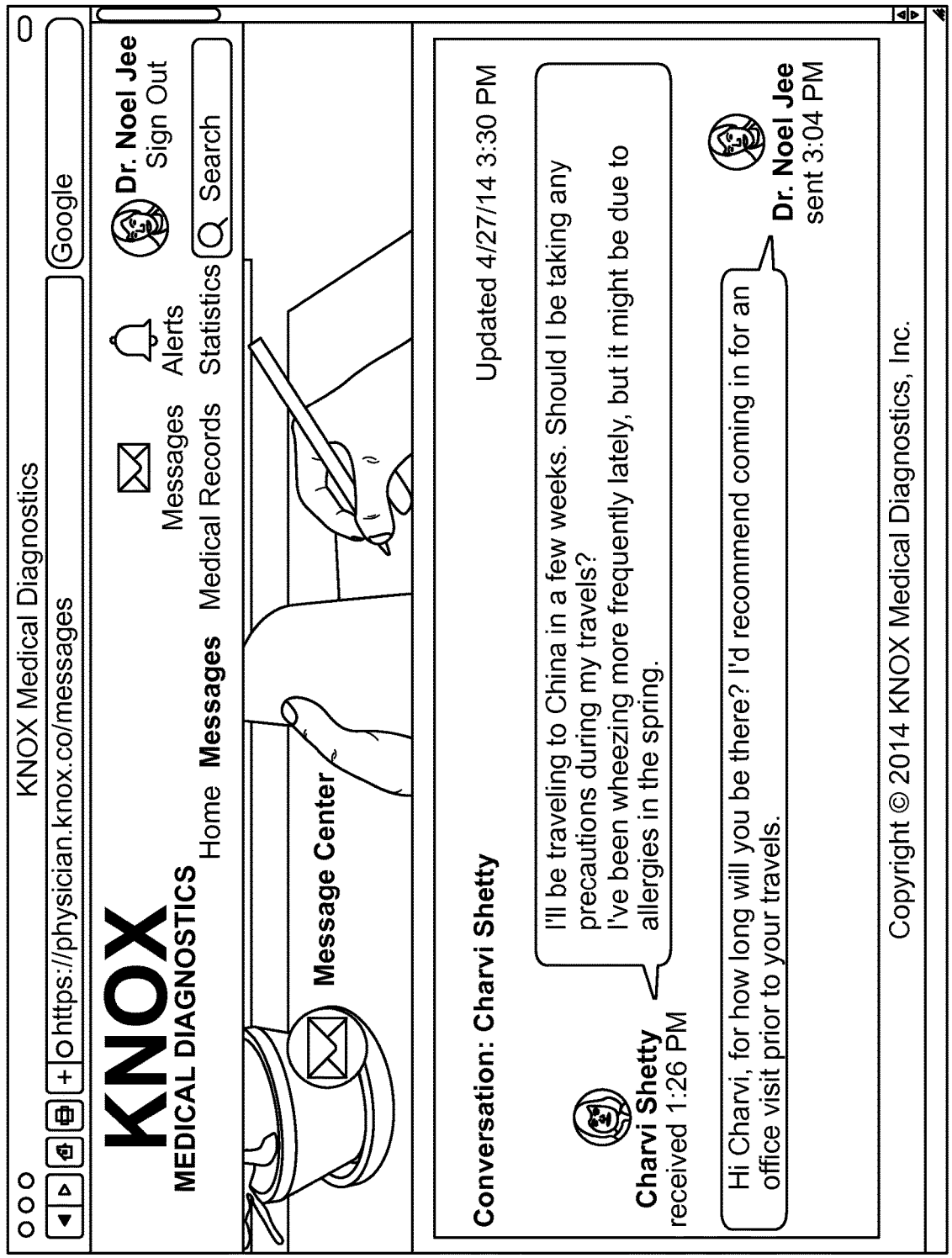
Figure 23C:
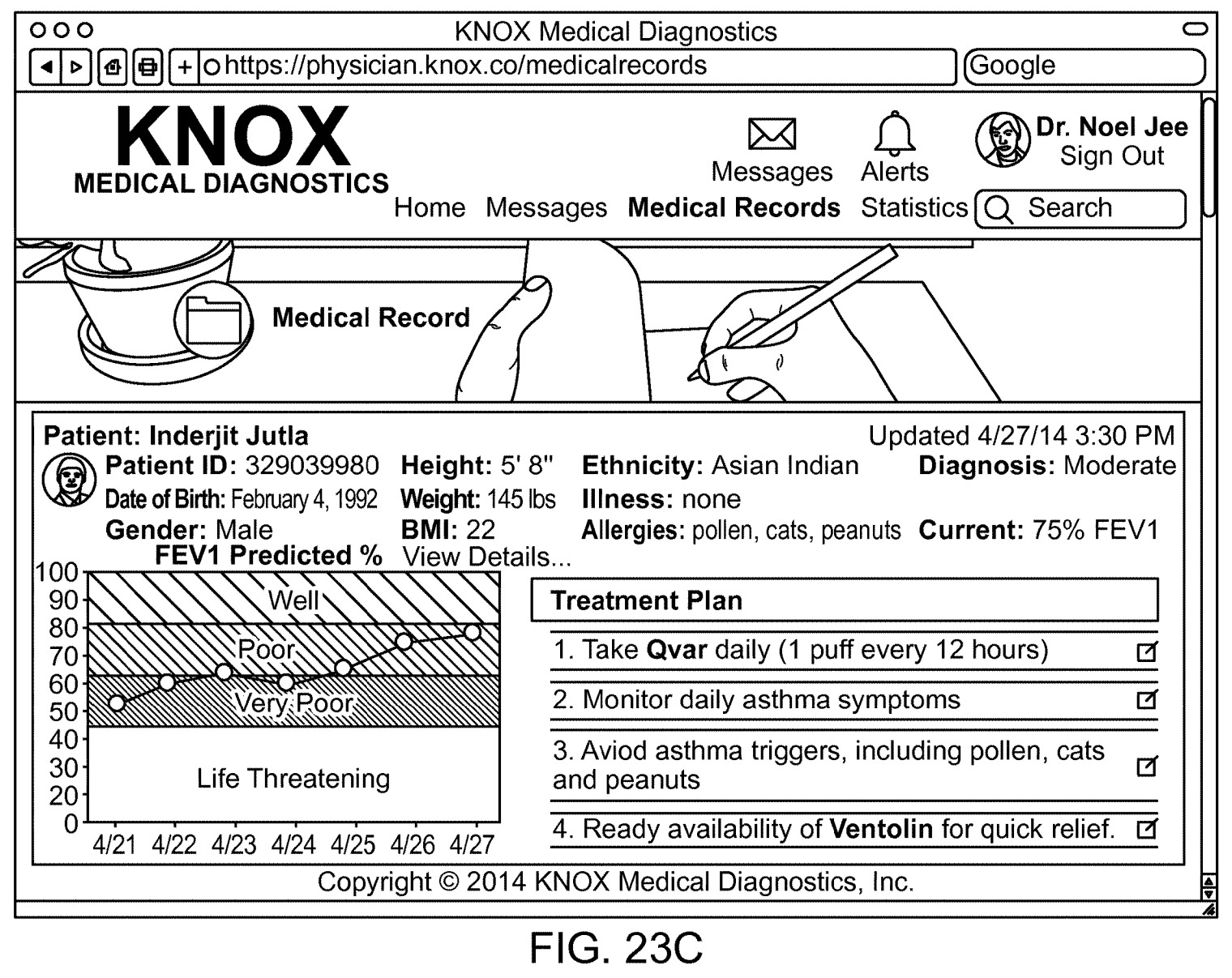

One non-limiting example of the physician portal GUI is provided in FIGS. 23A-C. Specifically, a non-limiting example of a home screen is shown in FIG. 23A. The home screen may be accessible once a physician logs in, and the home screen may provide the physician with a summary view of information available within the system, such as a summary of: new messages, patients with new reports, overall practice-wide statistics, and patient-specific statistics. From the home screen, the patient may be able to enroll new patients or view the results of currently-connected patients. In the depicted embodiment, by selecting the Messages icon or Message Center icon, the physician is directed to a screen that presents messages submitted by patients. One such message screen is shown in FIG. 23B. The portal of some embodiments allows patients to ask their physicians questions as they arise to improve patient adherence and outcomes.

Returning to FIG. 23A, in some embodiments, the home screen may present a display indicating how controlled each patient's respiratory condition is. The physician may also be provided with an option, on the home screen, to review any patient's spirometry readings. If such an option is selected, the system of some embodiments will direct the physician's remote computing device to a patient-specific medical records screen, such as the screen displayed in FIG. 23C. In some embodiments, the patient's biographical information is displayed alongside a chart showing trends in the patient's readings and the patient's prescribed treatment plan. The portal of some embodiments allows a physician to make modifications to a patient's treatment plan directly from the physician's computing device upon reviewing the patient's stored spirometry readings. Changes made to the patient's treatment plan are viewable by the patient within the patient GUI described above.

In various embodiments, the server 220 includes a processor and memory, and software code is stored in the memory, which when executed by the processor, causes the server 220 to perform some or all of the server functions described above. In some embodiments, the server 220 includes an application server. In some such embodiments, some software code is stored in the server 220, while additional software code is stored on each other network-connected device (e.g., 210, 230) in the form of a program application. In some such embodiments, "back end" functions such as storing information sets in databases, calculations, analyses, and information retrieval is largely performed by, and coded for, within the server 220, while "front end" functions, such as the display of information on a graphical user interface (GUI), is performed by, and coded for, within the other network-connected devices 210, 230. Additionally or alternatively, in some embodiments, the server 220 includes a web server and various features and functionality are made possible by the software code stored within the server 220. In some such embodiments, each of the other network-connected devices 210, 230 may include an internet browser, through which users can access, and interact with, the system for monitoring and treating asthma or other chronic respiratory condition 200. In various embodiments, the server 220 also includes a database server on which information sets such as historical patient data (e.g., past spirometry and biomarker recordings) are stored. It will be appreciated to one skilled in the art that the server 220 may be formed of any suitable number of servers. For example, in some embodiments, the server 220 includes one or a plurality of application servers, one or a plurality of web servers, and/or one or a plurality of database servers.

Figure 20:
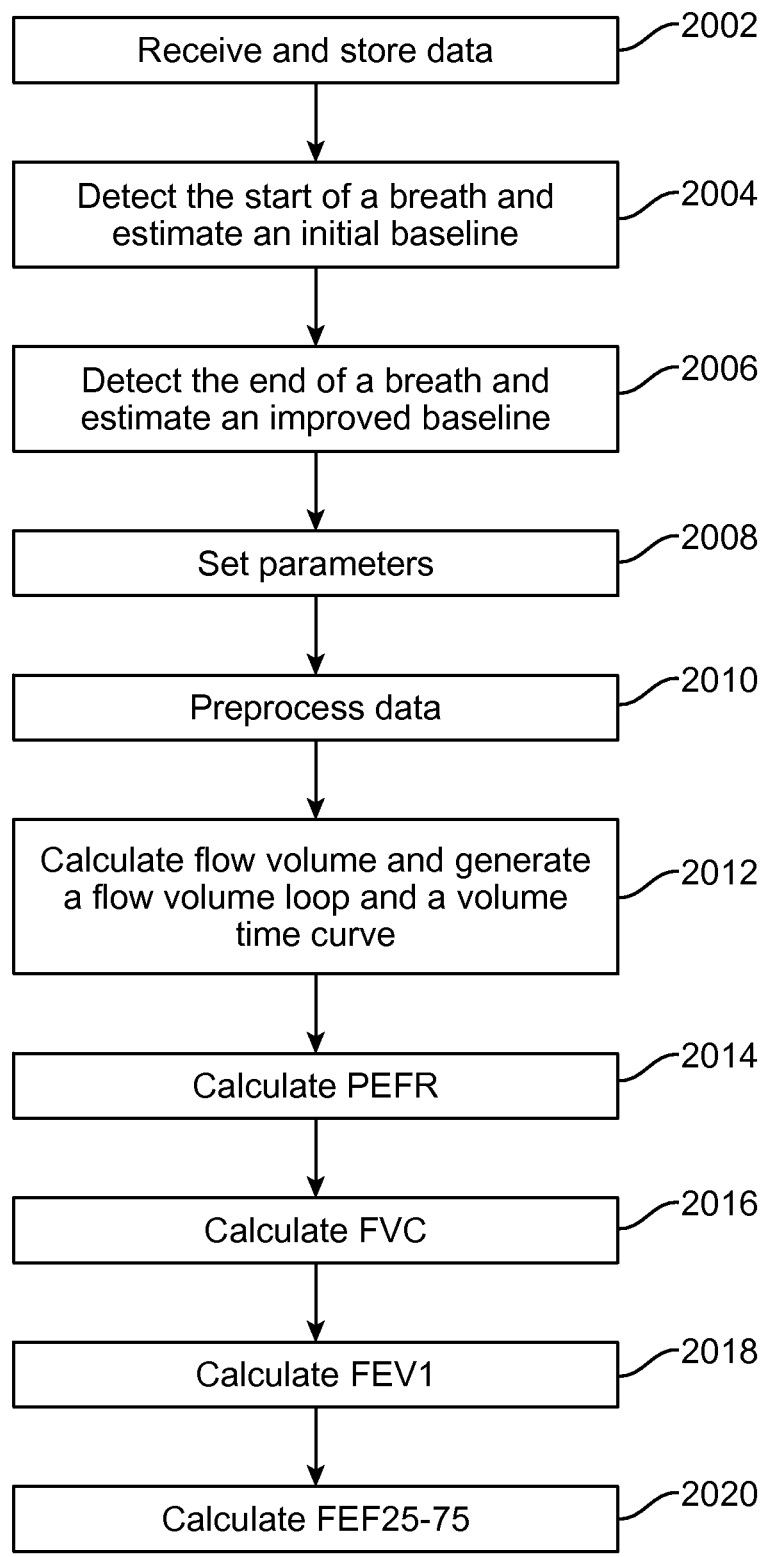
FIG. 20 depicts a flow chart of one embodiment of a method for detection and calculation of airflow parameters from data received from a handheld measurement device.

As described above, in various embodiments, the measurement device, remote computing device, and/or the server of a lung function monitoring system calculate one or more spirometry metrics from flow rate or volume data obtained from a patient's measurement device. In one embodiment, at least one or more of: the forced vital capacity (FVC), Forced Expiratory Volume within the first second (FEV1), and the Forced Expiratory Flow range between 25-75% of the max (FEF25-75%) are calculated by the remote computing device in accordance with the method of FIG. 20.

As shown in the method 2000, at block 2002, the processor of the remote computing device reads in raw data received as binary data, a text file, or other readable file from a measurement device. The file may be received over a wired or wireless connection. In some embodiments, the raw data is in the form of flow and/or flow rate data. If, instead, the raw data is in the form of pressure data, the processor of the remote computing device first converts the pressure data into flow rate data, for example, by applying Bernoulli's equation to determine flow and multiplying the flow by the cross-sectional area through which the flow occurs (as described above). At block 2004, the remote computing device detects the start of a breath. In some embodiments, the remote computing device establishes an initial baseline by averaging the first flow rate data points received, for example, the first 200 data points. Following establishment of a baseline, all acquired data is compared to the baseline. The start of a breath is identified by a significant change in flow rate over the baseline. In some embodiments, a set of data points that is at least 20 units (or corresponding to 0.5 L/s) greater than the baseline is identified as the start of a breath. In some embodiments, the acquired data is also reviewed to identify when the breath ended (i.e., when the flow rate data points returned to a relatively constant number—a steady state). The device of some embodiments then determines an improved baseline, as shown at block 2006 by averaging a set of data points, for example 300 data points, following the end of a breath with the initial baseline.

As shown at block 2008, in some embodiments, the device also identifies parameters such as sample rate and a scaling factor based on hardware specifications and/or a calibration process. At block 2010, the data points between the start and the end of the breath are preprocessed to prepare the data for use in spirometry calculations. For example, in some embodiments, the baseline flow rate value is subtracted from the breath data points, the data points are smoothed using a Gaussian function (for example, with sigma equaling one-tenth of the sample rate), and the resulting data is divided by the scaling factor. The preprocessed data may then be used to calculate various spirometry metrics.

At block 2012, a flow volume is calculated. In some embodiments, the preprocessed flow rate data is integrated from 0 to t, where t is each point in time between the start and end of the breath. The integrated data may be plotted against corresponding flow at corresponding times, or flow may be plotted against volume, to generate a flow volume loop. In some embodiments, different time parameters for integration are used to recalculate volume at each desired time frame, and the resulting integrated data is plotted against time to generate one or more volume time curves. At optional block 2014, the peak expiratory flow rate, PEFR (measured, for example, in L/s), is identified. PEFR is the maximum flow rate generated during a forceful exhalation and may be identified as the peak of the flow-volume loop. In some embodiments, as shown at block 2016, the forced vital capacity, FVC (measured, for example, in liters), which is the total volume of air forcibly expelled in an exhale, is identified. In some embodiments, FVC is identified as the peak of the volume time curve between 0 and t. In other embodiments, FVC is identified as the x-intercept of the flow-volume loop. At block 2018, FEV1 (measured, for example, in liters) is optionally calculated. In some embodiments, calculating FEV1 involves identifying the start of the volume time curve, which may be identified as the point on the curve located 50 ms before the first occurrence of a slope greater than 3. FEV1 is then identified as the volume one second after the start of the volume time curve. At block 2020, FEF25-75% (measured, for example, in L/s) is calculated. In some embodiments, FEF25-75 is the average slope of the flow volume loop between 25% maximum volume and 75% maximum volume.

In some embodiments, one or more of these spirometry metrics are presented to a user within an output display on a remote computing device. In various embodiments, one or more of these spirometry metrics are transmitted over a mobile or internet network via a wired or wireless connection to a server for storage and possible further analysis.

In an additional embodiment, a method is provided that utilizes the lung function and capacity measurements generated from a portable lung function measurement device to deliver objective measurements and personalized recommendations to athletes for optimal training regimens. It may also be used by non-athletes to track their lung health and level of exertion during physically demanding activities. In one example, a computing device in wired or wireless communication with the portable lung function monitoring device can identify and calculate metrics associated with a user's breathing and compare it to stored baseline data to determine the exertion level of the user. In some embodiments, the computing device calculates recommended or optimal lengths of rest during a workout, for example, in between sets. This recommended rest time may range from a few seconds to one or more minutes. The stored baseline data may be pre-programmed and based on a population average, for example, an average value for individuals within a certain age bracket and fitness level, or it may be based on a user-specific baseline calculated from previous recordings for the user. In some embodiments, the method enables athletes to determine if they are at their optimal lung health and/or determine the effectiveness of certain exercises. The method enables athletes to monitor how their bodies uniquely respond to various workouts, such as, for example, short burst exercises such as a 50 m sprint versus long, endurance type training such as medium-paced swimming for a mile without breaks. The method of some embodiments allows the athlete to avoid hazardous health situations like competing while physically exhausted, thereby reducing the risk of injury.

Figure 15:
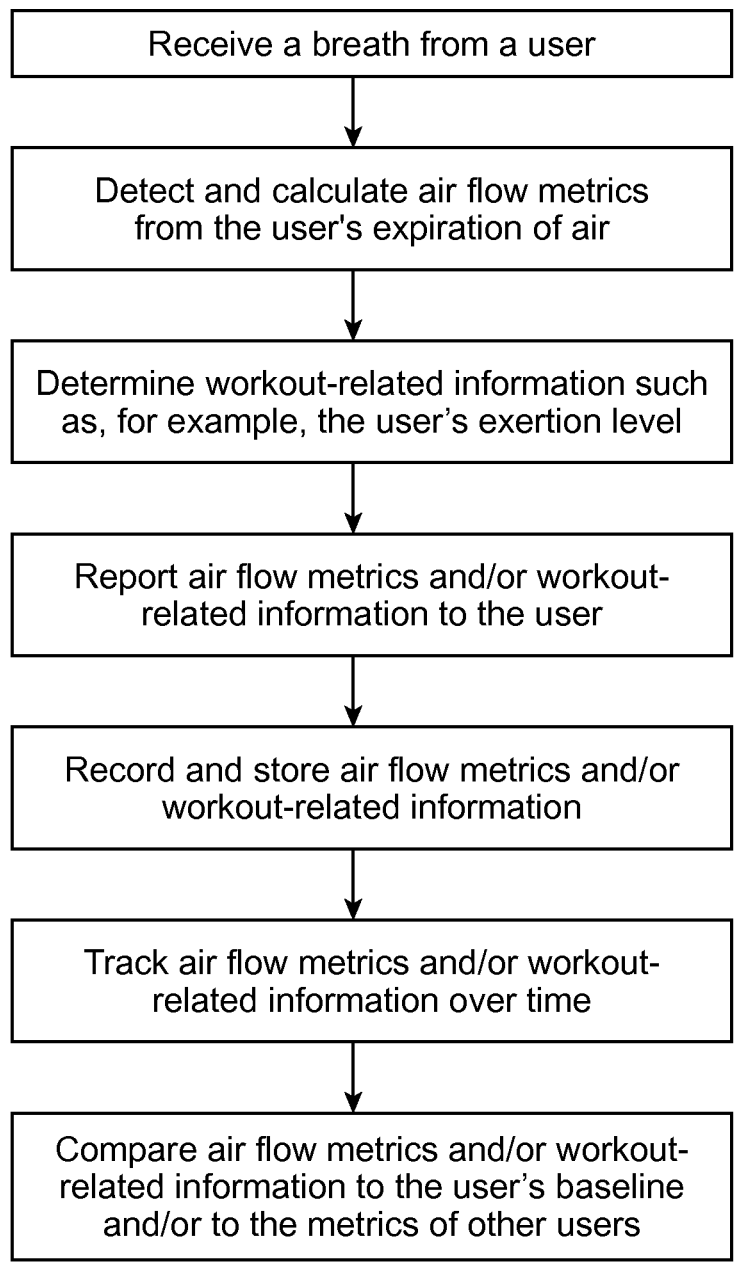
FIG. 15 depicts a flow chart of one embodiment of a method for tracking lung function during exercise or other physically demanding activity.

As shown in the flow chart of FIG. 15, in some embodiments, the method performed by a portable lung function monitoring system includes receiving a breath from a user, wherein the user exhales into a mouthpiece or aperture of a portable lung function measurement device. In various embodiments, the portable lung function measurement device includes at least the mouthpiece or aperture, a housing in which a spirometry detection unit is disposed, and a means of transmitting spirometry detection data from the device to a display. In some embodiments, the spirometry detection unit includes a pressure transducer and circuitry. In some embodiments, the means of transmitting includes a wireless transmitter configured to transmit data to a smartphone or other mobile computing device. The measurement device may be, for example, any measurement device described elsewhere herein. Continuing with FIG. 15, the method may further include detecting and calculating air flow metrics from the user's expiration of air. Such metrics may include velocity, flow rate, forced vital capacity, or any other metrics described elsewhere herein. The method of some embodiments also includes determining and providing workout-related information to a user, for example, via the display. The information may include, for example, how close the user is to achieving maximum exertion, whether the user's exertion level is within a healthy range, alerts, or messages of encouragement if the user is not providing enough exertion. In some embodiments, a user can select his or her target workout goals, and the portable lung function monitoring system can monitor whether the user is achieving them. In some embodiments, the user's air flow metrics are recorded and stored. Such metrics can be displayed to a user in a manner that allows the user to track his or her progress over time, for example throughout the course of a workout or over the course of days, weeks, months, or years.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

Those of skill in the art will appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

In one or more example embodiments, the functions described may be implemented in hardware, software, or firmware executed on a processor, or any combination thereof. For example, certain embodiments may comprise a computer program product for performing the operations presented herein. Such a computer program product may comprise a computer readable medium having instructions stored and/or encoded thereon, the instructions being executable by one or more processors to perform the operations described herein. When the functions described herein are implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), and Blu-ray disc where disks usually reproduce data magnetically, while discs reproduce data optically with lasers. Combinations of the above should also be included within the scope of computer-readable media.

Further, it should be appreciated that modules and/or other appropriate means for performing the methods and techniques described herein can be downloaded and/or otherwise obtained by a device as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or flash drive, etc.), such that a device can obtain the various methods upon coupling or providing the storage means to the device. Moreover, any other suitable technique for providing the methods and techniques described herein to a device can be utilized.

Throughout and within this specification, various technical publications are referenced to more fully describe the state of the art. The disclosures of these references are incorporated herein in their entireties.

Although the foregoing has included detailed descriptions of some embodiments by way of illustration and example, it will be readily apparent to those of ordinary skill in the art in light of the teachings of these embodiments that numerous changes and modifications may be made without departing from the spirit or scope of the appended claims.

What is claimed is:

1. A lung function measurement device, comprising:
 a flow head comprising a proximal end and a distal end, the flow head comprising:
  an inner tubular wall defining an inner lumen, and a mesh extending across an entire cross-section of the inner lumen at a discrete location, wherein the mesh is configured to generate resistance that causes a change in pressure within the inner lumen on opposing sides of the mesh upon airflow into the inner lumen;
  an outer tubular wall disposed circumferentially around the inner tubular wall such that an outer annular lumen is defined between the inner tubular wall and the outer tubular wall, the outer annular lumen forming a sensor-housing that is fluidly isolated from the inner lumen and an outside environment;
  a pressure sensor positioned within the sensor-housing, the pressure sensor to sense a pressure differential across the mesh and generate a pressure signal; and a processor disposed within the sensor-housing, the processor operatively coupled to the pressure sensor and configured to receive the pressure signal therefrom;

an aerosol holding chamber, a proximal end of the aerosol holding chamber removably coupled to the distal end of the flow head, and a distal end of the aerosol holding chamber configured to removably receive an inhaler containing a medication; and a distal cap removably coupled to the distal end of the aerosol holding chamber, the distal cap configured to receive the inhaler, wherein the proximal end of the flow head is configured to be engaged by a user so as to allow the user to exhale air into the flow head, or inhale the medication via the flow head.

2. The lung function measurement device of claim 1, wherein a diameter of the inner lumen on opposing sides of the mesh is equal.

3. The lung function measurement device of claim 1, wherein a first portion of the flow head is separable from a second portion of the flow head.

4. The lung function measurement device of claim 3, wherein the first portion and the second portion of the flow head are securely but separably connected via a friction fit or complementary threading.

5. The lung function measurement device of claim 3, wherein the mesh is accessible and removable when the first portion of the flow head and the second portion of the flow head are separated.

6. The lung function measurement device of claim 1, wherein the pressure sensor comprises a strain-based variable reluctance sensor comprising a spring member configured to deflect upon the airflow into the inner lumen, a plurality of coils, a plurality of coil forms, and media interface barriers, wherein a specific deflection of the spring member causes a specific change in modulation of inductance of the plurality of coils, which deflection is calibrated to a specific pressure measurement.

7. The lung function measurement device of claim 1, wherein the processor is configured to determine a flow rate of the airflow from the pressure signal.

8. The lung function measurement device of claim 1, further comprising a nitric oxide sensor disposed within the sensor-housing and configured to detect a concentration of nitric oxide in the airflow.

9. The lung function measurement device of claim 1, wherein one end of the pressure sensor is exposed within the inner lumen and a second end of the pressure sensor is disposed within the outer annular lumen.

10. The lung function measurement device of claim 1, further comprising a cardiopulmonary biomarker sensor, the cardiopulmonary biomarker sensor configured to sense pentane, ethane, 8-isoprostane, cysteinylleukotrienes, prostaglandin E2, hydrogen peroxide, aldehydes, nitrotyrosine, cytokines, and/or leukotriene B4.

11. The lung function measurement device of claim 10, wherein the cardiopulmonary biomarker sensor is disposed within the distal cap.

12. The lung function measurement device of claim 10, further comprising a warning indicator configured to generate a warning signal in response to an air flow of air exhaled by the user being less than an air flow threshold, or an amount of the cardiopulmonary biomarker in the exhaled air being greater than a biomarker threshold.

13. A lung function measurement device, comprising:
a flow head comprising a proximal end and a distal end, the flow head comprising:
an inner tubular wall defining an inner lumen, and a mesh extending across an entire cross-section of the inner lumen at a discrete location, wherein the mesh is configured to generate resistance that causes a change in pressure within the inner lumen on opposing sides of the mesh upon airflow into the inner lumen;
an outer tubular wall disposed circumferentially around the inner tubular wall such that an outer annular lumen is defined between the inner tubular wall and the outer tubular wall, the outer annular lumen forming a sensor-housing that is fluidly isolated from the inner lumen and an outside environment;
a pressure sensor positioned within the sensor-housing, the pressure sensor to sense a pressure differential across the mesh and generate a pressure signal; and
a processor disposed within the sensor-housing, the processor operatively coupled to the pressure sensor and configured to receive the pressure signal therefrom,
wherein:
the pressure sensor comprises a strain-based variable reluctance sensor comprising a spring member configured to deflect upon the airflow into the inner lumen, a plurality of coils, a plurality of coil forms, and media interface barriers, and
a specific deflection of the spring member causes a specific change in modulation of inductance of the plurality of coils, which deflection is calibrated to a specific pressure measurement.

* * * * *